(12) United States Patent
Halsall et al.

(10) Patent No.: US 8,735,410 B2
(45) Date of Patent: May 27, 2014

(54) QUINAZOLINE DERIVATIVES AS TYROSINE KINASE INHIBITORS

(75) Inventors: Christopher Thomas Halsall, Cheshire (GB); Laurent Francois Andre Hennequin, Cedex (FR); Alleyn Thomas Plowright, Cheshire (GB); Richard Storey, Cheshire (GB); Kieran Lennon, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 1320 days.

(21) Appl. No.: 11/884,923

(22) PCT Filed: Feb. 24, 2006

(86) PCT No.: PCT/GB2006/000656
§ 371 (c)(1),
(2), (4) Date: Sep. 19, 2008

(87) PCT Pub. No.: WO2006/090163
PCT Pub. Date: Aug. 31, 2006

(65) Prior Publication Data
US 2011/0152297 A1    Jun. 23, 2011

(30) Foreign Application Priority Data

Feb. 26, 2005  (GB) .................................. 0504018.3
Mar. 21, 2005  (GB) .................................. 0506657.6
Nov. 25, 2005  (GB) .................................. 0524001.5

(51) Int. Cl.
*A01N 43/54*    (2006.01)
*A61K 31/517*   (2006.01)

(52) U.S. Cl.
USPC ..................... 514/266.22; 544/293

(58) Field of Classification Search
USPC ..................... 514/266.22; 544/293
See application file for complete search history.

(56) References Cited

U.S. PATENT DOCUMENTS

| | | |
|---|---|---|
| 3,985,749 A | 10/1976 | Foster |
| 4,332,420 A | 6/1982 | Coski |
| 4,335,127 A | 6/1982 | Vandenberk et al. |
| 4,640,920 A | 2/1987 | Boyle et al. |
| 4,921,863 A | 5/1990 | Sugimoto et al. |
| 5,252,586 A | 10/1993 | Cain et al. |
| 5,405,843 A | 4/1995 | Fukazawa et al. |
| 5,457,105 A | 10/1995 | Barker |
| 5,616,582 A | 4/1997 | Barker |
| 5,721,237 A | 2/1998 | Myers et al. |
| 5,747,498 A | 5/1998 | Schnur et al. |
| 5,770,599 A | 6/1998 | Gibson |
| 5,770,603 A | 6/1998 | Gibson |
| 5,821,246 A | 10/1998 | Brown et al. |
| 5,866,572 A | 2/1999 | Barker et al. |
| 5,929,080 A | 7/1999 | Frost et al. |
| 5,962,458 A | 10/1999 | Lohmann et al. |
| 6,004,967 A | 12/1999 | McMahon et al. |
| 6,046,206 A | 4/2000 | Pamukcu et al. |
| 6,117,433 A | 9/2000 | Edens et al. |
| 6,126,917 A | 10/2000 | Mishani et al. |
| 6,177,433 B1 | 1/2001 | Uckum et al. |
| 6,225,318 B1 | 5/2001 | Sobolov-Jaynes et al. |
| 6,297,258 B1 | 10/2001 | Wissner et al. |
| 6,313,130 B1 | 11/2001 | Uckun et al. |
| 6,326,373 B1 | 12/2001 | Uckun et al. |
| 6,384,223 B1 | 5/2002 | Gletsos |
| 6,562,319 B2 | 5/2003 | Mishani et al. |
| 6,627,651 B1 | 9/2003 | Shirishi et al. |
| 6,653,305 B2 | 11/2003 | Himmelsbach et al. |
| 6,740,651 B2 | 5/2004 | Himmelsbach et al. |
| 6,924,285 B2 | 8/2005 | Himmelsbach et al. |
| 6,972,288 B1 | 12/2005 | Himmelsbach et al. |

(Continued)

FOREIGN PATENT DOCUMENTS

| CA | 2 375 259 A1 | 12/2000 |
|---|---|---|
| CA | 2 417 042 A1 | 3/2002 |

(Continued)

OTHER PUBLICATIONS

Pettit et al, Journal of Pharmaceutical Sciences, vol. 68, No. 12, Dec. 1979.*

Harris et al., poster presented at the XXII European Colloquium on Heterocyclic Chemistry (XXII ECHC-2006) in Bari, Italy, on Sep. 2-6, (2006).

Office Action in copending U.S. Appl. No. 10/572,048 mailed Oct. 31, 2008.

Ballard, Peter et al, "Inhibitors of epidermal growth factor receptor tyrosine kinase: Novel C-5 substituted anilinoquinazolines designed to target the ribose pocket," *Bioorganic & Medicinal Chemistry Letters* 16(6):1633-1637 (2006).

(Continued)

*Primary Examiner* — Wu-Cheng Winston Shen
*Assistant Examiner* — Jean Cornet

(57) ABSTRACT

The invention concerns quinazoline derivatives of the Formula I, or pharmaceutically acceptable salts thereof:

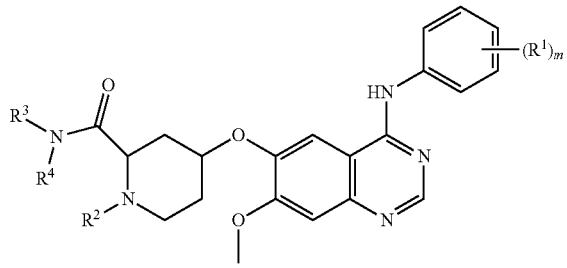

wherein each of $R^1$, $R^2$, $R^3$, $R^4$ and m are as defined in the description; processes for their preparation; pharmaceutical compositions containing them and their use in the manufacture of a medicament for providing an anti-proliferative effect. The quinazoline derivatives of Formula I are expected to be useful in the treatment of diseases such as certain cancers mediated by erbB receptor tyrosine kinases, and, for example, EGFR tyrosine kinase.

3 Claims, 2 Drawing Sheets

(56) References Cited

U.S. PATENT DOCUMENTS

| | | |
|---|---|---|
| 7,119,084 B2 | 10/2006 | Himmelsbach et al. |
| 7,148,230 B2 | 12/2006 | Bradbury et al. |
| 7,294,629 B2 | 11/2007 | Kitano et al. |
| 2002/0049197 A1 | 4/2002 | Himmelsbach et al. |
| 2002/0082270 A1 | 6/2002 | Himmelsbach et al. |
| 2002/0082271 A1 | 6/2002 | Himmelsbach et al. |
| 2002/0128553 A1 | 9/2002 | Mishani et al. |
| 2002/0169180 A1 | 11/2002 | Himmelsbach et al. |
| 2002/0173509 A1 | 11/2002 | Himmelsbach et al. |
| 2002/0173646 A1 | 11/2002 | Thomas et al. |
| 2002/0177601 A1 | 11/2002 | Himmelsbach et al. |
| 2003/0149062 A1 | 8/2003 | Jung et al. |
| 2003/0158196 A1 | 8/2003 | Jung et al. |
| 2004/0044014 A1 | 3/2004 | Himmelsbach et al. |
| 2004/0048880 A1 | 3/2004 | Himmelsbach et al. |
| 2004/0176361 A1 | 9/2004 | Fujio et al. |
| 2005/0165035 A1 | 7/2005 | Bradbury |
| 2005/0182043 A1 | 8/2005 | Himmelsbach et al. |
| 2005/0215574 A1 | 9/2005 | Bradbury et al. |
| 2006/0270672 A1 | 11/2006 | Himmelsbach et al. |
| 2007/0037837 A1 | 2/2007 | Hennequin et al. |
| 2007/0043010 A1 | 2/2007 | Bradbury et al. |
| 2007/0099943 A1 | 5/2007 | Bradbury et al. |
| 2008/0096881 A1 | 4/2008 | Hennequin et al. |

FOREIGN PATENT DOCUMENTS

| | | |
|---|---|---|
| CA | 2 417 050 A1 | 3/2002 |
| CA | 2 417 652 A1 | 1/2003 |
| CA | 2 417 897 A1 | 1/2003 |
| CA | 2 417 907 A1 | 1/2003 |
| EP | 0 288 563 | 11/1988 |
| EP | 0 326 330 | 8/1989 |
| EP | 0 566 226 | 10/1993 |
| EP | 0 607 439 | 7/1994 |
| EP | 0 602 851 | 10/1996 |
| EP | 0 520 722 | 12/1996 |
| EP | 0 787 722 | 8/1997 |
| EP | 0 837 063 | 4/1998 |
| EP | 0 635 507 | 9/1999 |
| EP | 1 230 919 | 8/2002 |
| EP | 1 283 039 | 2/2003 |
| EP | 1 369 418 | 12/2003 |
| GB | 2033894 | 5/1980 |
| GB | 2160201 | 12/1985 |
| GB | 2295387 | 5/1996 |
| JP | 11-189586 | 7/1999 |
| WO | WO 88/02365 | 4/1988 |
| WO | WO 92/14746 | 9/1992 |
| WO | WO 92/20642 | 11/1992 |
| WO | WO 93/08170 | 4/1993 |
| WO | WO 93/17682 | 9/1993 |
| WO | WO 94/27965 | 12/1994 |
| WO | WO 95/00146 | 1/1995 |
| WO | WO 95/03283 | 2/1995 |
| WO | WO 95/15758 | 6/1995 |
| WO | WO 95/24190 | 9/1995 |
| WO | WO 96/09294 | 3/1996 |
| WO | WO 96/15118 | 5/1996 |
| WO | WO 96/16960 | 6/1996 |
| WO | WO 96/30347 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 97/03069 | 1/1997 |
| WO | WO 97/11692 | 4/1997 |
| WO | WO 97/18813 | 5/1997 |
| WO | WO 97/22596 | 6/1997 |
| WO | WO 97/30034 | 8/1997 |
| WO | WO 97/30035 | 8/1997 |
| WO | WO 97/30044 | 8/1997 |
| WO | WO 97/32856 | 9/1997 |
| WO | WO 97/38983 | 10/1997 |
| WO | WO 97/38994 | 10/1997 |
| WO | WO 97/42187 | 11/1997 |
| WO | WO 98/02434 | 1/1998 |
| WO | WO 98/13354 | 4/1998 |
| WO | WO 98/38984 | 9/1998 |
| WO | WO 98/50038 | 11/1998 |
| WO | WO 98/50370 | 11/1998 |
| WO | WO 99/06378 | 2/1999 |
| WO | WO 99/09016 | 2/1999 |
| WO | WO 99/10349 | 3/1999 |
| WO | WO 99/24037 | 5/1999 |
| WO | WO 99/35132 | 7/1999 |
| WO | WO 99/61428 | 12/1999 |
| WO | WO 00/00202 | 1/2000 |
| WO | WO 00/06555 | 2/2000 |
| WO | WO 00/09481 | 2/2000 |
| WO | WO 00/10981 | 3/2000 |
| WO | WO 00/12497 | 3/2000 |
| WO | WO 00/18740 | 4/2000 |
| WO | WO 00/20402 | 4/2000 |
| WO | WO 00/24718 | 5/2000 |
| WO | WO 00/44728 | 8/2000 |
| WO | WO 00/47212 | 8/2000 |
| WO | WO 00/51587 | 9/2000 |
| WO | WO 00/51991 | 9/2000 |
| WO | WO 00/55141 | 9/2000 |
| WO | WO 00/55162 | 9/2000 |
| WO | WO 00/56338 | 9/2000 |
| WO | WO 00/56720 | 9/2000 |
| WO | WO 00/68203 | 11/2000 |
| WO | WO 00/73260 | 12/2000 |
| WO | WO 00/78735 | 12/2000 |
| WO | WO 01/04102 | 1/2001 |
| WO | WO 01/07432 | 2/2001 |
| WO | WO 01/12227 | 2/2001 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | WO 01/32632 | 5/2001 |
| WO | WO 01/32651 | 5/2001 |
| WO | WO 01/45641 | 6/2001 |
| WO | WO 01/66099 | 9/2001 |
| WO | WO 01/76586 | 10/2001 |
| WO | WO 01/77085 | 10/2001 |
| WO | WO 01/94341 | 12/2001 |
| WO | WO 01/98277 | 12/2001 |
| WO | WO 02/16352 | 2/2002 |
| WO | WO 02/18351 | 3/2002 |
| WO | WO 02/18370 | 3/2002 |
| WO | WO 02/18372 | 3/2002 |
| WO | WO 02/18373 | 3/2002 |
| WO | WO 02/18376 | 3/2002 |
| WO | WO 02/24684 | 3/2002 |
| WO | WO 02/30924 | 4/2002 |
| WO | WO 02/34711 | 5/2002 |
| WO | WO 02/34744 | 5/2002 |
| WO | WO 02/41882 | 5/2002 |
| WO | WO 02/44166 | 6/2002 |
| WO | WO 02/48117 | 6/2002 |
| WO | WO 02/50043 | 6/2002 |
| WO | WO 02/056882 | 7/2002 |
| WO | WO 02/062767 | 8/2002 |
| WO | WO 02/066445 | 8/2002 |
| WO | WO 02/068409 | 9/2002 |
| WO | WO 02/073235 | 9/2002 |
| WO | WO 02/076976 | 10/2002 |
| WO | WO 02/092577 | 11/2002 |
| WO | WO 02/092578 | 11/2002 |
| WO | WO 02/092579 | 11/2002 |
| WO | WO 02/094760 | 11/2002 |
| WO | WO 03/000188 | 1/2003 |
| WO | WO 03/040108 | 5/2003 |
| WO | WO 03/040109 | 5/2003 |
| WO | WO 03/045364 | 6/2003 |
| WO | WO 03/045395 | 6/2003 |
| WO | WO 03/049740 | 6/2003 |

(56) References Cited

FOREIGN PATENT DOCUMENTS

| WO | WO 03/064413 | 8/2003 |
|---|---|---|
| WO | WO 03/082290 | 10/2003 |
| WO | WO 03/082831 | 10/2003 |
| WO | WO 2004/064718 | 8/2004 |
| WO | WO 2004/093880 | 11/2004 |
| WO | WO 2004/096226 | 11/2004 |
| WO | WO 2005/012290 | 2/2005 |
| WO | WO 2005/026150 | 3/2005 |
| WO | WO 2005/026151 | 3/2005 |
| WO | WO 2005/026152 | 3/2005 |
| WO | WO 2005/026156 | 3/2005 |
| WO | WO 2005/026157 | 3/2005 |
| WO | WO 2005/028469 | 3/2005 |
| WO | WO 2005/028470 | 3/2005 |
| WO | WO 2005/030757 | 4/2005 |
| WO | WO 2005/030765 | 4/2005 |
| WO | WO 2005/041973 | 5/2005 |
| WO | WO 2005/051923 | 6/2005 |
| WO | WO 2005/075439 | 8/2005 |
| WO | WO 2005/118572 | 12/2005 |
| WO | WO 2006/064196 | 6/2006 |
| WO | WO 2006/090163 | 8/2006 |
| WO | WO 2006/092573 | 9/2006 |
| WO | WO 2006/092574 | 9/2006 |
| WO | WO 2006/117521 | 11/2006 |
| WO | WO 2006/117523 | 11/2006 |
| WO | WO 2007/034143 | 3/2007 |
| WO | WO 2007/034144 | 3/2007 |
| WO | WO 2007/063291 | 6/2007 |
| WO | WO 2007/063293 | 6/2007 |

OTHER PUBLICATIONS

Ballard, Peter et al, "Inhibitors of epidermal growth factor receptor tyrosine kinase: Optimization of potency and in vivo pharmacokinetics," *Bioorganic & Medicinal Chemistry Letters* 16(18):4908-4912 (2006).

Ballard, Peter et al, "5-Substituted 4-anilinoquinazolines as potent, selective and orally active inhibitors of erbB2 receptor tyrosine kinase," *Bioorganic & Medicinal Chemistry Letters* 15(19):4226-4229 (2005).

Barker et al., Studies Leading to the Identification of ZD1839 (Iressa™): An Orally Active, Selective Epidermal Growth Factor Receptor Tyrosine Kinase Inhibitor Targeted to the Treatment of Cancer, Bioorg. Med. Chem. Lett. 11(14): 1911-1914 (2001).

Bridges et al., "Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor," J. Med. Chem. 39: 267-276 (1996).

Chevalier et al., "Induction of DNA replication by peroxisome proliferators is independent of both tumour necrosis factor (alpha) priming and EGF-receptor tyrosine kinase activity," J. Cell Sci. 112(24): 4785-4791 (1999).

Denny et al., "Structure-Activity Relationships for 4-Anilinoquinazolines as Potent Inhibitors at the ATP Binding Site for the Epidermal Growth Factor Receptor in vitro," Clinical and Experimental Pharmacology and Physiology 23:424-427 (1996).

Gazit et al., "Tyrophostins IV-Highly Potent Inhibitors . . . Relationship Study of 4-Anilidoquinazolines," Bioorganic & Medicinal Chemistry 48(8): 1203-1207 (1996).

Ghosh et al., "Structure-based design of potent inhibitors of EGF-receptor tyrosine kinease as anti-cancer agents," Anti-Cancer Drug Design 14, 403-410 (1999).

Harris, Craig et al, "Selective alkylation of a 6,7-dihydroxyquinazoline," *Tetrahedron Letters* 46(45):7715-7719 (2005).

Harris, Craig et al, "Facile synthesis of 7-amino anilinoquinazolines via direct amination of the quinazoline core," *Tetrahedron Letters* 46(43):7381-7384 (2005).

Hennequin et al., "Novel 4-Anilinoquinazolines with C-7 Basic Side Chains: Designs and Structure Activity Relationship of a Series of Potent, Orally Active VEGF Receptor Tyrosine Kinase Inhibitors," J. Med. Chem., ACS, 45:1300-1312.

Hennequin, Laurent et al, "Novel 4-anilinoquinazolines with C-6 carbon-linked side chains: Synthesis and structure-activity relationship of a series of potent, orally active, EGF receptor tyrosine kinase inhibitors," *Bioorganic & Medicinal Chemistry Letters* 16(10):2672-2676 (2006).

Hennequin et al., "Design and structure-activity relationship of a new class of potent VEGF receptor tyrosine kinase inhibitors," J. Med. Chem. 42: 5369-5389 (1999).

March, J., Advanced Organic Chemistry—Reactions, Mechanisms, and Structure, $4^{th}$ Ed., © 1992, John Wiley & Sons, New York, NY, pp. 357-362.

Mendelsohn et al., "Status of Epidermal Growth Factor Receptor Antagonists in the Biology and Treatment of Cancer," J. Clinical Oncology 21(14): 2787-2799 (2003).

Mendelsohn, "Targeting the Epidermal Growth Factor Receptor for Cancer Therapy," Journal of Clinical Oncology 20(18s):2s-13s (2002).

Myers et al., "The preparation and SAR of 4-(anilion), 4-(phenoxy), and 4-(thiophenoxy)-quinzolines: inhibitors of p56lck and EGF-R tyrosine kinase activity," Biorg. Med. Chem. Lett. 7(4): 417-420 (1997).

Pao et al., "Epidermal Growth Factor Receptor Mutations, Small-Molecule Kinase Inhibitors, and Non-Small-Cell Lung Cancer: Current Knowledge and Future Directions," Journal of Clinical Oncology 23(11):1-13 (2005).

Rewcastle et al., "Tyrosine Kinase Inhibitors. 5 . . . 4-(Phenylamino)quinazolines as Potent . . . Inhibitors of the Tyrosine Kinase Domain of the Epidermal Growth Factor Receptor," J. Med. Chem. 38:3482-3487 (1995).

Singh et al., "Inhibitors of the epidermal growth factor receptor protein tyrosine kinase: A quantitative structure-activity relationship analysis," J. Enzyme Inhibition 13:125-134 (1998).

Smaill et al., "Tyrosine kinase inhibitors. 17. Irreversible inhibitors of the epidermal growth factor receptor: 4-(Phenylamino)quinazoline- and 4-(Phe-nylamino)pyrido," J. Med. Chem. 43(16):3199 (2000).

Stamos et al., "Structure of the Epidermal Growth Factor Receptor Kinase Domain Alone and in Complex with a 4-Anilinoquinazoline Inhibitor," J. Bio. Chem. 277(48):46265-46272 (2002).

Traxler, "Oncologic, Endocrine & Metabolic: Protein tyrosine kinase inhibitors in cancer treatment," Expert Opinion on Therapeutic Patents 7:571-588 (1997).

Traxler, "Monthly Focus: Oncologic, Endocrine & Metabolic: Tyrosine kinase inhibitors in cancer treatment (Part II)," Expert Opinion on Therapeutic Patents 8:1599-1625 (1998).

Tsou et al., "6-Substituted-4-(3-bromophenylamino)quinazolines as Putative Irreversible Inhibitors of the Epidermal Growth Factor Receptor (Egfr) and Human Epidermal Growth Factor Receptor (Her-2) Tyrosine Kinases with Enhanced Antitumor Activity," J. Med. Chem. 44:2719-2734 (2001).

Vema et al., "Design of EGFR Kinase Inhibitors: A Ligand-Based Approach and its Confirmation with Structure-Based Studies," Bioorg. Med. Chem. 11:4643-4653(2003).

Wright et al., "Allosteric inhibition of fructose-1,6-bisphosphatase by anilinoquinazolines," Bioorg. Med. Chem. Lett. 11(1):17-21 (2001).

Decision in Patent Interferences 105,595 McK and 105,596 McK dated Jun. 17, 2008.

English Translation of Office Action in Japanese Patent Appln. No. 2003-580299, the Japanese counterpart of the present application, dated May 11, 2006.

Response to Office Action in Japanese Patent Appln. No. 2003-580299, the Japanese counterpart of the present application, dated Jul. 28, 2006.

English translation of Response to Office Action in Japanese Patent Appln. No. 2003-580299, the Japanese counterpart of the present application, dated Jul. 28, 2006.

English translation of Response to Office Action in Japanese Patent Appln. No. 2003-580299, the Japanese counterpart of U.S. Appl. No. 10/508,675, dated Oct. 26, 2006.

(56) References Cited

OTHER PUBLICATIONS

Office Action in Indian Patent Appln. No. 2630/DELNP/2004, the Indian counterpart of the present application, dated Apr. 20, 2006.
Response to Office Action in Indian Patent Appln. No. 2630/DELNP/2004, the Indian counterpart of the present application, dated Jul. 24, 2006.
English translation of Office Action in Chinese Patent Appln. No. 03811739.8, the Chinese counterpart of the present application, dated Jul. 21, 2006.
Response to Office Action in Chinese Patent Appln. No. 03811739.8, the Chinese counterpart of U.S. Appl. No. 10/508,675, dated Dec. 5, 2006.
English translation of Response to Office Action in Chinese Patent Appln. No. 03811739.8 of U.S. Appl. No. 10/508,675, dated Dec. 5, 2006.
Communication from European Patent Office in EP Appln. No. 03 710 015.3, the European counterpart of the present application, dated Sep. 22, 2006.
Communication from EPO dated Mar. 9, 2006, in EP Appln. No. 03 710 015.3, the European counterpart of U.S. Appl. No. 10/508,675.
Communication from European Patent Office ("EPO") dated May 27, 2005, in EP Appln. No. 03 710 015.3, the European counterpart of U.S. Appl. No. 10/508,675.
Reply to May 27, 2005 Communication from EPO dated Sep. 20, 2005, in EP Appln. No. 03 710 015.3, the European counterpart of U.S. Appl. No. 10/508,675.
Office Action in copending U.S. Appl. No. 10/571,991 mailed Aug. 19, 2008.
G.A. Patani et al., "Bioisosterism: A Rational Approach in Drug Design," *Chem. Rev.* 96:3147-3176 (1996).

* cited by examiner

XRPD pattern of (2R,4R)-4-({4-[(3-chloro-2-fluorophenyl)amino]-7-methoxyquinazolin-6-yl}oxy)-N,1-dimethylpiperidine-2-carboxamide dimaleate salt DSC trace of (2R,4R)-4-({4-[(3-chloro-2-fluorophenyl)amino]-7-methoxyquinazolin-6-yl}oxy)-N,1-dimethylpiperidine-2-carboxamide dimaleate salt

QUINAZOLINE DERIVATIVES AS TYROSINE KINASE INHIBITORS

This application is a national stage filing under 35 U.S.C. §371 of International Application No. PCT/GB2006/000656, filed on Feb. 24, 2006. This application claims priority of GB 0504018.3, filed Feb. 26, 2005, GB 0506657.6, filed Mar. 31, 2005, and GB 0524001.5, filed Nov. 25, 2005.

The invention concerns certain novel quinazoline derivatives, or pharmaceutically acceptable salts thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors as well as paracrine and endocrine factors. By binding to specific transmembrane receptors, these ligands integrate the extracellular signal to the intracellular signalling pathways, therefore transducing the signal across the plasma membrane and allowing the individual cell to respond to its extracellular signals. Many of these signal transduction processes utilise the reversible process of the phosphorylation of proteins that are involved in the promotion of these diverse cellular responses. The phosphorylation status of target proteins is regulated by specific kinases and phosphatases that are responsible for the regulation of about one third of all proteins encoded by the mammalian genome. As phosphorylation is such an important regulatory mechanism in the signal transduction process, it is therefore not surprising that aberrations in these intracellular pathways result in abnormal cell growth and differentiation and so promote cellular transformation (reviewed in Cohen et al, *Curr Opin Chem Biol,* 1999, 3, 459-465).

It has been widely shown that a number of these tyrosine kinases are mutated to constitutively active forms and/or when over-expressed result in the transformation of a variety of human cells. These mutated and over-expressed forms of the kinase are present in a large proportion of human tumours (reviewed in Kolibaba et al, Biochimica et Biophysica Acta, 1997, 133, F217-F248). As tyrosine kinases play fundamental roles in the proliferation and differentiation of a variety of tissues, much focus has centred on these enzymes in the development of novel anti-cancer therapies. This family of enzymes is divided into two groups—receptor and non-receptor tyrosine kinases e.g. EGF Receptors and the SRC family respectively. From the results of a large number of studies including the Human Genome Project, about 90 tyrosine kinase have been identified in the human genome, of this 58 are of the receptor type and 32 are of the non-receptor type. These can be compartmentalised in to 20 receptor tyrosine kinase and 10 non-receptor tyrosine kinase sub-families (Robinson et al, *Oncogene,* 2000, 19, 5548-5557).

The receptor tyrosine kinases are of particular importance in the transmission of mitogenic signals that initiate cellular replication. These large glycoproteins, which span the plasma membrane of the cell possess an extracellular binding domain for their specific ligands (such as Epidermal Growth Factor (EGF) for the EGF Receptor). Binding of ligand results, in the activation of the receptor's kinase enzymatic activity that is encoded by the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., *EMBO J.,* 2000, 19, 3159). One mechanism in which this can be accomplished is by overexpression of the receptor at the protein level, generally as a result of gene amplification. This has been observed in many common human cancers (reviewed in Klapper et al., *Adv. Cancer Res.,* 2000, 77, 25) such as breast cancer (Sainsbury et al., *Brit. J. Cancer,* 1988, 58, 458; Guerin et al., *Oncogene Res.,* 1988, 3, 21; Slamon et al., *Science,* 1989, 244, 707; Klijn et al., *Breast Cancer Res. Treat.,* 1994, 29, 73 and reviewed in Salomon et al., *Crit. Rev. Oncol. Hematol.,* 1995, 19, 183), non-small cell lung cancers (NSCLCs) including adenocarcinomas (Cerny et al., *Brit. J. Cancer,* 1986, 54, 265; Reubi et al., *Int. J. Cancer,* 1990, 45, 269; Rusch et al., *Cancer Research,* 1993, 53, 2379; Brabender et al, *Clin. Cancer Res.,* 2001, 7, 1850) as well as other cancers of the lung (Hendler et al., *Cancer Cells,* 1989, 7, 347; Ohsaki et al., *Oncol. Rep.,* 2000, 7, 603), bladder cancer (Neal et al., *Lancet,* 1985, 366; Chow et al., *Clin. Cancer Res.,* 2001, 7, 1957, Zhau et al., *Mol. Carcinog.,* 3, 254), oesophageal cancer (Mukaida et al., *Cancer,* 1991, 68, 142), gastrointestinal cancer such as colon, rectal or stomach cancer (Bolen et al., *Oncogene Res.,* 1987, 1, 149; Kapitanovic et al., *Gastroenterology,* 2000, 112, 1103; Ross et al., *Cancer Invest.,* 2001, 19, 554), cancer of the prostate (Visakorpi et al., *Histochem. J.,* 1992, 24, 481; Kumar et al., 2000, 32, 73; Scher et al., *J. Natl. Cancer Inst.,* 2000, 92, 1866), leukaemia (Konaka et al., *Cell,* 1984, 37, 1035, Martin-Subero et al., *Cancer Genet Cytogenet.,* 2001, 127, 174), ovarian (Hellstrom et al., *Cancer Res.,* 2001, 61, 2420), head and neck (Shiga et al., *Head Neck,* 2000, 22, 599) or pancreatic cancer (Ovotny et al., *Neoplasma,* 2001, 48, 188). As more human tumour tissues are tested for expression of the erbB family of receptor tyrosine kinases it is expected that their widespread prevalence and importance will be further enhanced in the future.

As a consequence of the mis-regulation of one or more of these receptors, it is widely believed that many tumours become clinically more aggressive and so correlate with a poorer prognosis for the patient (Brabender et al, *Clin. Cancer Res.,* 2001, 7, 1850; Ross et al, *Cancer Investigation,* 2001, 19, 554, Yu et al., *Bioessays,* 2000, 22.7, 673).

In addition, to these clinical findings, a wealth of pre-clinical information suggests that the erbB family of receptor tyrosine kinases are involved in cellular transformation. This includes the observations that many tumour cell lines over-express one or more of the erbB receptors and that EGFR or erbB2 when transfected into non-tumour cells have the ability to transform these cells. This tumorigenic potential has been further verified as transgenic mice that overexpress erbB2 spontaneously develop tumours in the mammary gland. In addition to this, a number of pre-clinical studies have demonstrated that anti-proliferative effects can be induced by knocking out one or more erbB activities by small molecule inhibitors, dominant negatives or inhibitory antibodies (reviewed in Mendelsohn et al., *Oncogene,* 2000, 19, 6550). Thus it has been recognised that inhibitors of these receptor tyrosine kinases should be of value as a selective inhibitor of the proliferation of mammalian cancer cells (Yaish et al. *Science,* 1988, 242, 933, Kolibaba et al, Biochimica et Biophysica Acta, 1997, 133, F217-F248; Al-Obeidi et al, 2000, *Oncogene*, 19, 5690-5701; Mendelsohn et al, 2000, *Oncogene*, 19, 6550-6565).

The small molecule EGFR tyrosine kinase inhibitors, Iressa (also known as gefitinib, and ZD1834) and Tarceva (also known as erlotinib) have been approved for use in the treatment of advanced non-small cell lung cancer. Furthermore, findings using inhibitory antibodies against EGFR and erbB2 (c-225 and trastuzumab respectively) have proven to be beneficial in the clinic for the treatment of selected solid tumours (reviewed in Mendelsohn et al, 2000, *Oncogene*, 19, 6550-6565).

Recently mutations in the ATP binding pocket of the intracellular catalytic domain of the EGF receptor have been discovered in certain sub-sets of non-small cell lung cancers (NSCLCs). The presence of mutations in the receptor appear to correlate with response to EGFR tyrosine kinase inhibitors such as gefitinib (Lynch et al, N Engl J Med 2004; 350: 2129-2139; Paez et al, Science 2004; 304: 1497-1500), although it is becoming evident that the clinical benefits of compounds such as gefitinib and erlotinib are not likely to be mediated by EGFR mutations alone. It has been demonstrated that ligand stimulation results in a different phosphorylation pattern in mutated receptors compared with that seen in wild-type receptors and it is thought that mutant EGF receptors selectively transduce survival signals on which NSCLCs become dependent. Inhibition of those signals by compounds such as gefitinib may contribute to the efficacy of such drugs (Sordella et al. Science 2004; 305: 1163-1167). Accordingly the inhibition of the EGF tyrosine kinase in both wild-type and mutated receptors is an important target that would be expected to provide an anti-cancer effect.

Amplification and/or activity of members of the erbB receptor tyrosine kinases have been detected and so have been implicated to play a role in a number of non-malignant proliferative disorders such as psoriasis (Ben-Bassat, *Curr. Pharm. Des.*, 2000, 6, 933; Elder et al., Science, 1989, 243, 811), benign prostatic hyperplasia (BPH) (Kumar et al., *Int. Urol. Nephrol.*, 2000, 32,73), atherosclerosis and restenosis (Bokemeyer et al., *Kidney Int.*, 2000, 58, 549). It is therefore expected that inhibitors of erbB type receptor tyrosine kinases will be useful in the treatment of these and other non-malignant disorders of excessive cellular proliferation.

In addition, inhibition of the erbB type receptor tyrosine kinases, such as the EGFR tyrosine kinase, may be useful in the treatment of diseases or conditions of the respiratory tract, including, for example, inflammatory disease and Chronic Obstructive Pulmonary Disease (COPD) (J.-H. Kim et al. Chest 2004, 126, 888, K. Takeyama et al. Proc. Natl. Acad. Sci. U S A 1999, 96, 3081 and P.-R. Burgel et al., Thorax 2004, 59).

Patent application publication numbers WO 96/33977, WO 96/33978, WO 96/33979, WO 96/33980, WO 96/33981, WO 97/30034, WO 97/30035, WO 97/38994, WO 98/13354, WO 00/55141, WO 00/56720, WO 02/41882, WO 03/82290, EP 566 226 and EP 837 063 disclose that certain quinazoline derivatives which bear an anilino substituent at the 4-position and a substituent at the 6- and/or 7-position possess receptor tyrosine kinase inhibitory activity.

Patent application publication number WO 03/082831 discloses 4-(2,3-dihalogenoanilino)quinazoline compounds substituted at the 6-position by a heterocyclyloxy or heterocyclylalkoxy group which are erbB, particularly EGFR tyrosine kinase inhibitors. WO 03/082831 discloses as Example 25 the compound:

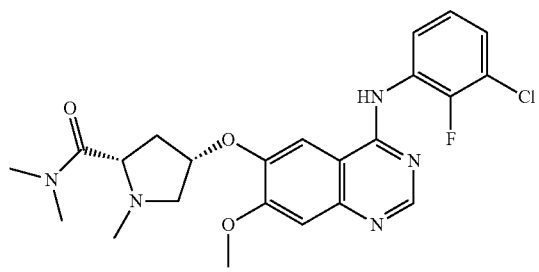 [SMILES: COc1cc2ncnc(Nc3cccc(Cl)c3F)c2cc1O[C@H]1C[C@@H](C(=O)N(C)C)N(C)C1]

and certain stereoisomers thereof in Example 46.

WO 03/082831 also discloses, as Examples 24 and 47, the compounds:

Example 24

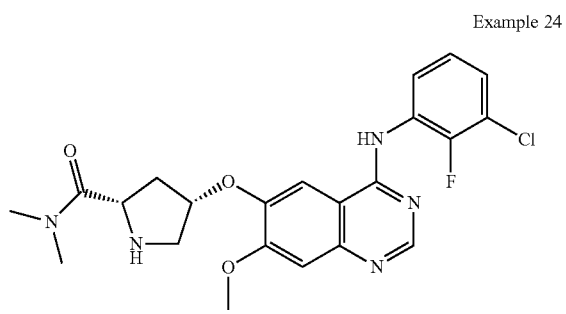

Example 47

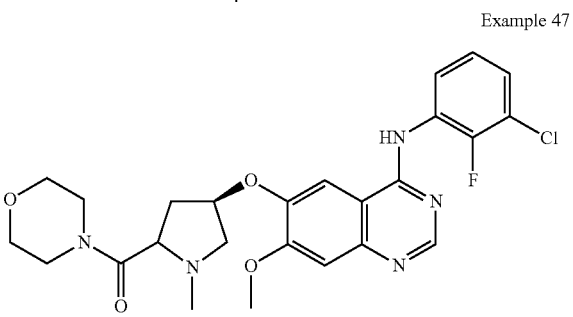

There remains, however, a need to find further compounds with good in-vivo activity together with improved pharmacological characteristics compared with known erbB tyrosine kinase inhibitors, particularly compounds that are selective EGFR tyrosine kinase inhibitors. For example, there is a need for novel compounds with advantageous and/or improved characteristics in, but not limited to for example, (i) physical properties; (ii) favourable DMPK properties, such as high bioavailability and/or advantageous half life and/or advantageous volume of distribution and/or high absorption; (iii) factors that decrease the liability for clinical drug-drug interactions (e.g., cytochrome P450 enzyme inhibition or induction); and (iv) compounds with a reduced liability for QT interval prolongation in patients, for example compounds which are inactive or weakly active in a HERG assay.

We have now surprisingly found that certain 4-halogenoanilinoquinazoline compounds which carry certain carbon substituted piperidin-4-yloxy groups at C6 on the quinazoline ring, exhibit a combination of favourable properties, such as those described hereinbefore, for example a high in-vivo activity together with good DMPK properties, including high bioavailability and good absorption.

Without wishing to imply that the compounds disclosed in the present invention possess pharmacological activity only by virtue of an effect on a single biological process, it is believed that the compounds provide an anti-tumour effect by way of inhibition of one or more of the erbB family of receptor tyrosine kinases that are involved in the signal transduction steps which lead to the proliferation of tumour cells. In particular, it is believed that the compounds of the present invention provide an anti-tumour effect by way of the selective inhibition of EGFR tyrosine kinase.

References to erbB receptors, particularly EGFR, used herein are intended to include both wild-type and mutated receptors unless specifically stated otherwise. The term "mutation" includes, but is not limited to nucleotide in-frame deletions or substitutions in one or more of the exons that encode receptors such as EGFR.

Generally the compounds of the present invention possess potent inhibitory activity against the erbB receptor tyrosine kinase family, particularly by inhibition of EGFR tyrosine kinases, whilst possessing less potent inhibitory activity against other kinases. The compounds of the present invention possess substantially better potency against the EGFR tyrosine kinase over that of the erbB2 tyrosine kinase. Accordingly, it may be possible to administer a compound according to the present invention at a dose that is sufficient to inhibit EGFR tyrosine kinase whilst having no significant effect upon erbB2 or other tyrosine kinases. The selective inhibition provided by the compounds according to the present invention may provide treatments for conditions mediated by EGFR tyrosine kinase, whilst, for example, reducing undesirable side effects that may be associated with the inhibition of other tyrosine kinases.

According to a first aspect of the invention there is provided a quinazoline derivative of the formula I:

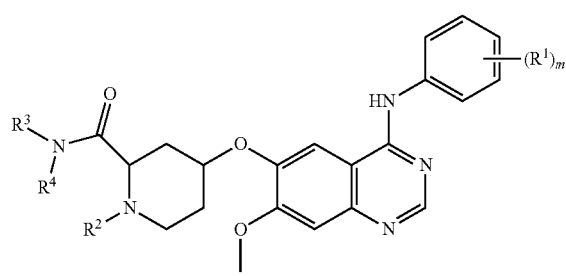

I wherein:
m is 1, 2 or 3;
each $R^1$, which may be the same or different, is halogeno;
$R^2$ is selected from hydrogen and (1-4C)alkyl;
$R^3$ is hydrogen; and
$R^4$ is selected from hydrogen and (1-4C)alkyl;
or a pharmaceutically acceptable salt thereof.

In one embodiment of the invention m is 1, 2 or 3; each $R^1$, which may be the same or different, is halogeno; $R^2$ is (1-4C) alkyl; $R^3$ is hydrogen; and
$R^4$ is selected from hydrogen and (1-4C)alkyl; or a pharmaceutically acceptable salt thereof.

In an embodiment m is 1, 2 or 3 and each $R^1$, which may be the same or different, is selected from fluoro, chloro and bromo.

In another embodiment m is 2 or 3, one $R^1$ is fluoro and the other $R^1$ is selected from fluoro, chloro and bromo.

In another embodiment the anilino group at the 4-position on the quinazoline ring in formula I is selected from 3-chloro-2-fluoroanilino, 3-chloro-5-fluoroanilino, 3-chloro-4-fluoroanilino, 3-bromo-2-fluoroanilino, 3-chloro-2,6-difluoroanilino and 3-chloro-2,4-difluoroanilino.

In a further embodiment the anilino group at the 4-position on the quinazoline ring in formula I is 3-chloro-2-fluoroanilino.

In a further embodiment the anilino group at the 4-position on the quinazoline ring in formula I is 3-bromo-2-fluoroanilino.

In a further embodiment the anilino group at the 4-position on the quinazoline ring in formula I is 3-chloro-4-fluoroanilino.

In a further embodiment $R^2$ is (1-4C)alkyl.
In a further embodiment $R^2$ is hydrogen.
In a further embodiment $R^2$ is (1-3C)alkyl.
In a further embodiment $R^2$ is selected from methyl, ethyl and isopropyl.
In a further embodiment $R^2$ is selected from hydrogen and methyl.
In a further embodiment $R^2$ is methyl.
In a further embodiment at least one of $R^2$ and $R^4$ is (1-4C) alkyl, for example $R^2$ is hydrogen and $R^4$ is methyl, or $R^2$ is methyl and $R^4$ is hydrogen.
In a further embodiment $R^4$ is selected from hydrogen and (1-3C)alkyl, for example $R^4$ is selected from hydrogen, methyl, ethyl and isopropyl, more particularly, $R^4$ is methyl or $R^4$ is hydrogen.
In a further embodiment $R^4$ is (1-3C)alkyl, for example $R^4$ is selected from methyl, ethyl and isopropyl.
In a further embodiment $R^3$ and $R^4$ are both hydrogen.
In a further embodiment $R^2$ is methyl and $R^4$ is selected from hydrogen and (1-3C)alkyl, for example $R^2$ is methyl and $R^4$ is selected from hydrogen, methyl and ethyl. In a further embodiment $R^2$ and $R^4$ are both methyl. In a still further embodiment $R^2$ is methyl and $R^4$ is hydrogen.
In a further embodiment $R^2$ is methyl or hydrogen and $R^4$ is methyl.

In a further embodiment there is provided a quinazoline derivative of the formula I wherein:
m is 1 or 2;
is $R^1$ is selected from fluoro, chloro and bromo;
$R^2$ is selected from methyl, ethyl and isopropyl;
$R^3$ is hydrogen; and
$R^4$ is selected from hydrogen, methyl, ethyl and isopropyl (particularly $R^4$ is hydrogen or methyl);
or a pharmaceutically acceptable salt thereof.

In a further embodiment there is provided a quinazoline derivative of the formula I wherein:
$R^2$ is methyl;
$R^3$ is hydrogen;
$R^4$ is selected from hydrogen and methyl; and
the anilino group at the 4-position on the quinazoline ring in formula I is selected from 3-chloro-2-fluoroanilino, 3-chloro-4-fluoroanilino and 3-bromo-2-fluoroanilino (particularly the anilino group is 3-chloro-2-fluoroanilino);
or a pharmaceutically acceptable salt thereof.

In a further embodiment there is provided a quinazoline derivative of the formula I wherein:
$R^2$ is methyl;
$R^3$ is hydrogen;
$R^4$ is methyl; and
wherein the anilino group at the 4-position on the quinazoline ring in formula I is selected from 3-chloro-2-fluoroanilino, 3-chloro-4-fluoroanilino and 3-bromo-2-fluoroanilino (particularly the anilino group is 3-chloro-2-fluoroanilino);
or a pharmaceutically acceptable salt thereof.

In a further embodiment there is provided a quinazoline derivative of the formula I wherein:
$R^2$ is methyl;
$R^3$ and $R^4$ are both hydrogen; and
wherein the anilino group at the 4-position on the quinazoline ring in formula I is selected from 3-chloro-2-fluoroanilino, 3-chloro-4-fluoroanilino and 3-bromo-2-fluoroanilino (particularly the anilino group is 3-chloro-2-fluoroanilino);
or a pharmaceutically acceptable salt thereof.

In a further embodiment there is provided a quinazoline derivative of the formula I wherein:
$R^4$ is methyl and $R^2$ is hydrogen, or
$R^4$ is hydrogen and $R^2$ is methyl;
$R^3$ is hydrogen; and
the anilino group at the 4-position on the quinazoline ring in formula I is selected from 3-chloro-2-fluoroanilino, 3-chloro-4-fluoroanilino and 3-bromo-2-fluoroanilino (particularly the anilino group is 3-chloro-2-fluoroanilino);
or a pharmaceutically acceptable salt thereof.

A particular quinazoline derivative of the formula I is a compound of the formula Ia:

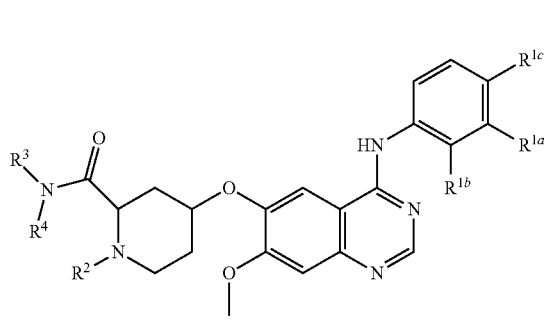

Ia wherein
$R^{1a}$ is chloro or bromo;
$R^{1b}$ is hydrogen and $R^{1c}$ is fluoro; or
$R^{1c}$ is hydrogen and $R^{1b}$ is fluoro; and
$R^2$, $R^3$ and $R^4$ have any of the values mentioned hereinbefore in relation to the compound of formula I;
or a pharmaceutically acceptable salt thereof.

A further embodiment is a compound of the formula Ia wherein:
$R^{1a}$ is chloro or bromo;
$R^{1b}$ is hydrogen and $R^{1c}$ is fluoro; or
$R^{1c}$ is hydrogen and $R^{1b}$ is fluoro;
$R^2$ is selected from hydrogen and (1-3C)alkyl (for example $R^2$ is (1-3C)alkyl, particularly methyl or $R^2$ is hydrogen); and
$R^3$ is hydrogen;
$R^4$ is selected from hydrogen, methyl, ethyl and isopropyl (particularly $R^4$ is hydrogen or methyl);
or a pharmaceutically acceptable salt thereof.

A further embodiment is a compound of the formula Ia wherein:
$R^2$ is methyl;
$R^3$ is hydrogen;
$R^4$ is methyl; and
wherein the anilino group at the 4-position on the quinazoline ring in formula Ia is selected from 3-chloro-2-fluoroanilino and 3-bromo-2-fluoroanilino (particularly the anilino group is 3-chloro-2-fluoroanilino);
or a pharmaceutically acceptable salt thereof.

A further embodiment is a compound of the formula Ia wherein:
$R^2$ is methyl;
$R^3$ and $R^4$ are both hydrogen; and
wherein the anilino group at the 4-position on the quinazoline ring in formula Ia is selected from 3-chloro-2-fluoroanilino and 3-bromo-2-fluoroanilino (particularly the anilino group is 3-chloro-2-fluoroanilino);
or a pharmaceutically acceptable salt thereof.

A further embodiment is a compound of the formula Ia wherein:
$R^2$ is hydrogen;
$R^3$ is hydrogen;
$R^4$ is methyl; and
wherein the anilino group at the 4-position on the quinazoline ring in formula Ia is selected from 3-chloro-2-fluoroanilino and 3-bromo-2-fluoroanilino (particularly the anilino group is 3-chloro-2-fluoroanilino);
or a pharmaceutically acceptable salt thereof.

Another particular quinazoline derivative of the formula I is a compound of the formula Ib:

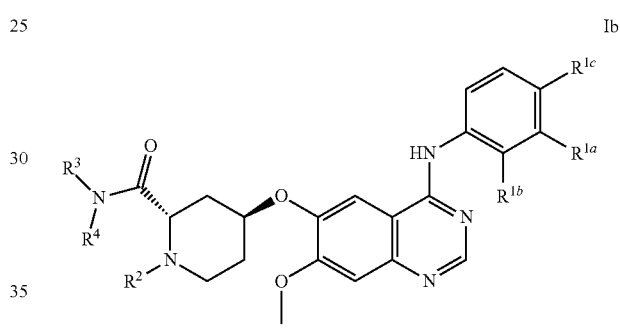

Ib wherein:
$R^{1a}$ is chloro or bromo;
$R^{1b}$ is hydrogen and $R^{1c}$ is fluoro; or
$R^{1c}$ is hydrogen and $R^{1b}$ is fluoro;
$R^2$ is hydrogen or (1-3C)alkyl (for example $R^2$ is (1-3C)alkyl, particularly methyl, or alternatively $R^2$ is hydrogen);
$R^3$ is hydrogen; and
$R^4$ is hydrogen or methyl;
or a pharmaceutically acceptable salt thereof.

In this embodiment a suitably $R^2$ and $R^4$ are not both hydrogen. For example $R^2$ is hydrogen and $R^4$ is methyl, or $R^2$ is methyl and $R^4$ is hydrogen.

A particular compound of the formula Ib is wherein:
$R^{1a}$ is chloro or bromo (particularly $R^{1a}$ is chloro);
$R^{1b}$ is fluoro;
$R^{1c}$ is hydrogen;
$R^2$ is methyl;
$R^3$ is hydrogen; and
$R^4$ is hydrogen or methyl;
or a pharmaceutically acceptable salt thereof.

Another particular compound of the formula Ib is wherein:
$R^{1a}$ is chloro or bromo (particularly $R^{1a}$ is chloro);
$R^{1b}$ is fluoro;
$R^{1c}$ is hydrogen;
$R^2$ is methyl; and
$R^3$ and $R^4$ are both hydrogen;
or a pharmaceutically acceptable salt thereof.

Another particular compound of the formula Ib is wherein:
$R^{1a}$ is chloro or bromo (particularly $R^{1a}$ is chloro);
$R^{1b}$ is fluoro;
$R^{1c}$ is hydrogen;
$R^2$ is hydrogen;
$R^3$ is hydrogen; and
$R^4$ is methyl;
or a pharmaceutically acceptable salt thereof.

Another particular quinazoline derivative of the formula I is a compound of the formula Ic:

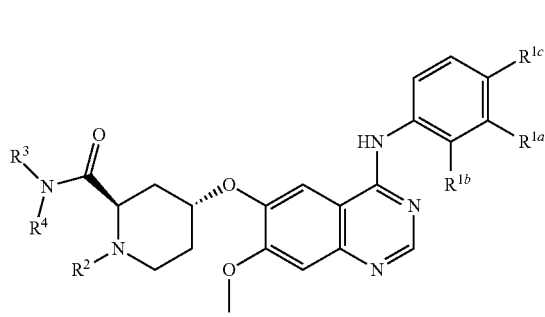

Ic wherein:
$R^{1a}$ is chloro or bromo;
$R^{1b}$ is hydrogen and $R^{1c}$ is fluoro; or
$R^{1c}$ is hydrogen and $R^{1b}$ is fluoro;
$R^2$ is hydrogen or (1-3C)alkyl (for example $R^2$ is (1-3C)alkyl, particularly methyl, or alternatively $R^2$ is hydrogen);
$R^3$ is hydrogen;
$R^4$ is hydrogen or methyl;
or a pharmaceutically acceptable salt thereof.

In this embodiment a suitably $R^2$ and $R^4$ are not both hydrogen. For example $R^2$ is hydrogen and $R^4$ is methyl, or $R^2$ is methyl and $R^4$ is hydrogen.

A particular compound of the formula Ic is wherein:
$R^{1a}$ is chloro or bromo (particularly $R^{1a}$ is chloro);
$R^{1b}$ is fluoro;
$R^{1c}$ is hydrogen;
$R^2$ is methyl;
$R^3$ is hydrogen; and
$R^4$ is hydrogen or methyl;
or a pharmaceutically acceptable salt thereof.

Another particular compound of the formula Ic is wherein:
$R^{1a}$ is chloro or bromo (particularly $R^{1a}$ is chloro);
$R^{1b}$ is fluoro;
$R^{1c}$ is hydrogen;
$R^2$ is methyl;
$R^3$ is hydrogen; and
$R^4$ is methyl;
or a pharmaceutically acceptable salt thereof.

Another particular compound of the formula Ic is wherein:
$R^{1a}$ is chloro or bromo (particularly $R^{1a}$ is chloro);
$R^{1b}$ is fluoro;
$R^{1c}$ is hydrogen;
$R^2$ is methyl; and
$R^3$ and $R^4$ are both hydrogen;
or a pharmaceutically acceptable salt thereof.

Another particular compound of the formula Ic is wherein:
$R^{1a}$ is chloro or bromo (particularly $R^{1a}$ is chloro);
$R^{1b}$ is fluoro;
$R^{1c}$ is hydrogen;
$R^2$ is hydrogen;
$R^3$ is hydrogen; and
$R^4$ is methyl;
or a pharmaceutically acceptable salt thereof.

Compounds of the formula Ic exhibit favourable properties including high in-vivo potency together with good DMPK properties such as high absorption and/or low efflux.

Another particular quinazoline derivative of the formula I is a compound of the formula Id:

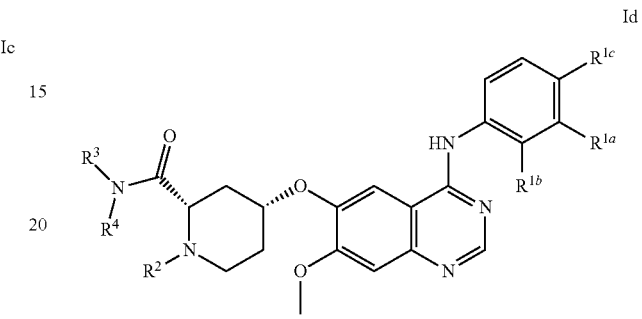

Id wherein:
$R^{1a}$ is chloro or bromo;
$R^{1b}$ is hydrogen and $R^{1c}$ is fluoro; or
$R^{1c}$ is hydrogen and $R^{1b}$ is fluoro;
$R^2$ is hydrogen or (1-3C)alkyl (for example $R^2$ is (1-3C)alkyl, particularly methyl, or alternatively $R^2$ is hydrogen);
$R^3$ is hydrogen;
$R^4$ is hydrogen or methyl;
or a pharmaceutically acceptable salt thereof.

In this embodiment a suitably $R^2$ and $R^4$ are not both hydrogen. For example $R^2$ is hydrogen and $R^4$ is methyl, or $R^2$ is methyl and $R^4$ is hydrogen.

A particular compound of the formula Id is wherein:
$R^{1a}$ is chloro or bromo (particularly $R^{1a}$ is chloro);
$R^{1b}$ is fluoro;
$R^{1c}$ is hydrogen;
$R^2$ is methyl;
$R^3$ is hydrogen; and
$R^4$ is hydrogen or methyl;
or a pharmaceutically acceptable salt thereof.

Another particular compound of the formula Id is wherein:
$R^{1a}$ is chloro or bromo (particularly $R^{1a}$ is chloro);
$R^{1b}$ is fluoro;
$R^{1c}$ is hydrogen;
$R^2$ is methyl;
$R^3$ is hydrogen; and
$R^4$ is methyl;
or a pharmaceutically acceptable salt thereof.

Another particular compound of the formula Id is wherein:
$R^{1a}$ is chloro or bromo (particularly $R^{1a}$ is chloro);
$R^{1b}$ is fluoro;
$R^{1c}$ is hydrogen;
$R^2$ is methyl; and
$R^3$ and $R^4$ are both hydrogen;
or a pharmaceutically acceptable salt thereof.

Another particular compound of the formula Id is wherein:
$R^{1a}$ is chloro or bromo (particularly $R^{1a}$ is chloro);
$R^{1b}$ is fluoro;
$R^{1c}$ is hydrogen;
$R^2$ is hydrogen;

R³ is hydrogen; and
R⁴ is methyl;
or a pharmaceutically acceptable salt thereof.

Another particular quinazoline derivative of the formula I is a compound of the formula Ie:

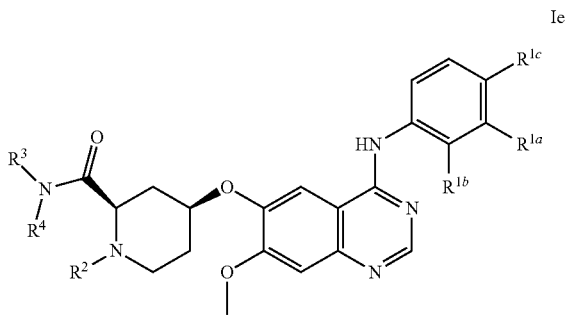

Ie wherein:
R¹ᵃ is chloro or bromo;
R¹ᵇ is hydrogen and R¹ᶜ is fluoro; or
R¹ᶜ is hydrogen and R¹ᵇ is fluoro;
R² is hydrogen or (1-3C)alkyl (for example R² is (1-3C)alkyl, particularly methyl, or alternatively R² is hydrogen);
R³ is hydrogen;
R⁴ is hydrogen or methyl;
or a pharmaceutically acceptable salt thereof.

In this embodiment a suitably R² and R⁴ are not both hydrogen. For example R² is hydrogen and R⁴ is methyl, or R² is methyl and R⁴ is hydrogen.

A particular compound of the formula Ie is wherein:
R¹ᵃ is chloro or bromo (particularly R¹ᵃ is chloro);
R¹ᵇ is fluoro;
R¹ᶜ is hydrogen;
R² is methyl;
R³ is hydrogen; and
R⁴ is hydrogen or methyl;
or a pharmaceutically acceptable salt thereof.

Another particular compound of the formula Ie is wherein:
R¹ᵃ is chloro or bromo (particularly R¹ᵃ is chloro);
R¹ᵇ is fluoro;
R¹ᶜ is hydrogen;
R² is methyl;
R³ is hydrogen; and
R⁴ is methyl;
or a pharmaceutically acceptable salt thereof.

Another particular compound of the formula Ie is wherein:
R¹ᵃ is chloro or bromo (particularly R¹ᵃ is chloro);
R¹ᵇ is fluoro;
R¹ᶜ is hydrogen;
R² is methyl; and
R³ and R⁴ are both hydrogen;
or a pharmaceutically acceptable salt thereof.

Another particular compound of the formula Ie is wherein:
R¹ᵃ is chloro or bromo (particularly R¹ᵃ is chloro);
R¹ᵇ is fluoro;
R¹ᶜ is hydrogen;
R² is hydrogen;
is R³ is hydrogen; and
R⁴ is methyl;
or a pharmaceutically acceptable salt thereof.

A particular compound of the invention is the quinazoline derivative of the formula I selected from:
(2S,4S)-4-({4-[(3-chloro-2-fluorophenyl)amino]-7-methoxyquinazolin-6-yl}oxy)-N,1-dimethylpiperidine-2-carboxamide;
(2R,4R)-4-({4-[(3-chloro-2-fluorophenyl)amino]-7-methoxyquinazolin-6-yl}oxy)-N,1-dimethylpiperidine-2-carboxamide;
(2S,4S)-4-({4-[(3-chloro-2-fluorophenyl)amino]-7-methoxyquinazolin-6-yl}oxy)-1-methylpiperidine-2-carboxamide;
(2R,4R)-4-({4-[(3-chloro-2-fluorophenyl)amino]-7-methoxyquinazolin-6-yl}oxy)-1-methylpiperidine-2-carboxamide;
(2R,4R)-4-({4-[(3-chloro-2-fluorophenyl)amino]-7-methoxyquinazolin-6-yl}oxy)-N-methylpiperidine-2-carboxamide;
(2S,4R)-4-({4-[(3-chloro-2-fluorophenyl)amino]-7-methoxyquinazolin-6-yl}oxy)-N,1-dimethylpiperidine-2-carboxamide; and
(2R,4S)-4-({4-[(3-chloro-2-fluorophenyl)amino]-7-methoxyquinazolin-6-yl}oxy)-N,1-dimethylpiperidine-2-carboxamide;
or a pharmaceutically acceptable salt thereof.

It is to be understood that certain compounds of the formula I may exist in solvated as well as unsolvated forms such as, for example, hydrated forms. It is to be understood that the invention encompasses all such solvated forms which possess an inhibitory effect on an erbB receptor tyrosine kinase, such as antiproliferative activity.

It is also to be understood that certain compounds of the formula I may exhibit polymorphism, and that the invention encompasses all such forms which possess an inhibitory effect on an erbB receptor tyrosine kinase, such as antiproliferative activity.

It is also to be understood that the invention relates to all tautomeric forms of the compounds of the formula I which exhibit an inhibitory effect on an erbB receptor tyrosine kinase, such as antiproliferative activity.

A suitable pharmaceutically acceptable salt of a compound of the formula I is, for example, an acid-addition salt of a compound of the formula I, for example an acid-addition salt with an inorganic or organic acid. Suitable inorganic acids include, for example, hydrochloric, hydrobromic or sulfuric acid. Suitable organic acids include, for example, trifluoroacetic, citric, maleic, tartaric, fumaric, methanesulfonic or 4-toluenesulfonic acid. A particular salt of a compound of formula I is a salt formed with maleic acid (cis-butenedioic acid). In a particular embodiment there is provided a dimaleate salt of a compound of formula I. More particularly a salt of 4-({4-[(3-chloro-2-fluorophenyl)amino]-7-methoxyquinazolin-6-yl}oxy)-N,1-dimethylpiperidine-2-carboxamide (and stereoisomers thereof such as the (2R,4R), (2S,4S), (2S,4R) and (2R,4S) isomers) with maleic acid (particularly the dimaleate salt, for example the (2R,4R) 4-({4-[(3-chloro-2-fluorophenyl)amino]-7-methoxyquinazolin-6-yl}oxy)-N,1-dimethylpiperidine-2-carboxamide dimaleate) exhibit favourable properties in comparison to the free base form of the compound, for example one or more of:
(i) improved dissolution characteristics such as a high intrinsic dissolution rate;
(ii) high bioavailability; and/or
(iii) reduced variability in exposure following oral administration.

The salt may be amorphous, semi-crystalline or crystalline. In a particular embodiment the salt is crystalline. The term "crystalline" used herein refers to a quinazoline derivative of the formula I which is highly crystalline, such as greater than about 60%, conveniently greater than about 80%, for example greater than about 90%, more particularly greater than about 95% crystalline, and still more particularly greater than about 98% crystalline. The degree of crystallinity may be determined using standard methods, for example X-ray diffraction methods.

References herein to "semi-crystalline" refer to quinazoline derivatives of the invention that contain both crystalline and non-crystalline (such as amorphous) compound. For example, compounds that are less than about 60% crystalline, such as less than about 50%, 30%, 20%, 10% or 5% crystalline.

When the salt is a dimaleate salt of a quinazoline derivative of formula I, the molar ratio the quinazoline derivative of formula I to maleate counter ion is about 1:2, for example from 1:1.5 to 1:2.5. Particularly the dimaleate salt has a molar ratio of the quinazoline of formula I:maleate counter ion of 1:2.

The identity of a particular salt of the present invention, such as a dimaleate salt can be confirmed by conventional methods, for example proton nuclear magnetic resonance (NMR) analysis.

A particular salt is (2R,4R) 4-({4-[(3-chloro-2-fluorophenyl)amino]-7-methoxyquinazolin-6-yl}oxy)-N,1-dimethylpiperidine-2-carboxamide dimaleate. As mentioned hereinbefore the dimaleate may be amorphous, semi-crystalline or crystalline. In a particular embodiment there is provided crystalline (2R,4R) 4-({4-[(3-chloro-2-fluorophenyl)amino]-7-methoxyquinazolin-6-yl}oxy)-N,1-dimethylpiperidine-2-carboxamide dimaleate.

In a further embodiment of the invention there is provided a crystalline form of (2R,4R) 4-({4-[(3-chloro-2-fluorophenyl)amino]-7-methoxyquinazolin-6-yl}oxy)-N,1-dimethylpiperidine-2-carboxamide dimaleate with an X-ray powder diffraction pattern with at least one peak at a 2θ value of about 5.2.

In a further embodiment of the invention there is provided crystalline (2R,4R) 4-({4-[(3-chloro-2-fluorophenyl)amino]-7-methoxyquinazolin-6-yl}oxy)-N,1-dimethylpiperidine-2-carboxamide dimaleate with an X-ray powder diffraction pattern with specific peaks at 2θ values of about 5.2 and 8.2.

In a further embodiment of the invention there is provided crystalline (2R,4R) 4-({4-[(3-chloro-2-fluorophenyl)amino]-7-methoxyquinazolin-6-yl}oxy)-N,1-dimethylpiperidine-2-carboxamide dimaleate with an X-ray powder diffraction pattern with specific peaks at 2θ values of about 5.2, 8.2 and 10.3.

In a further embodiment of the invention there is provided crystalline (2R,4R) 4-({4-[(3-chloro-2-fluorophenyl)amino]-7-methoxyquinazolin-6-yl}oxy)-N,1-dimethylpiperidine-2-carboxamide dimaleate with an X-ray powder diffraction pattern with specific peaks at 2θ values of about 5.2, 8.2, 10.3 and 10.6.

In a further embodiment of the invention there is provided crystalline (2R,4R) 4-({4-[(3-chloro-2-fluorophenyl)amino]-7-methoxyquinazolin-6-yl}oxy)-N,1-dimethylpiperidine-2-carboxamide dimaleate with an X-ray powder diffraction pattern with specific peaks at 2θ values of about those shown in Table 1:

TABLE 1

| Angle 2-Theta (2θ)° | Relative Intensity % |
|---|---|
| 5.2 | 48.2 |
| 8.2 | 30.9 |
| 10.3 | 12.9 |
| 10.6 | 39.8 |
| 12.5 | 11.7 |
| 12.8 | 16 |
| 13.1 | 90.7 |
| 15.6 | 25.7 |
| 15.9 | 48.4 |
| 17.4 | 30.2 |
| 17.9 | 15 |
| 19.8 | 26 |
| 20.0 | 19.2 |
| 20.2 | 11.1 |
| 20.8 | 17.2 |
| 21.0 | 23.4 |
| 21.5 | 60.7 |
| 22.6 | 21 |
| 23.1 | 60.2 |
| 23.4 | 46.3 |
| 24.0 | 14.4 |
| 24.2 | 13.8 |
| 24.8 | 23.2 |
| 26.7 | 14.4 |
| 27.7 | 15.4 |
| 28.2 | 16 |
| 29.2 | 23.3 |
| 29.7 | 13.1 |

In a further embodiment of the invention there is provided crystalline (2R,4R) 4-({4-[(3-chloro-2-fluorophenyl)amino]-7-methoxyquinazolin-6-yl}oxy)-N,1-dimethylpiperidine-2-carboxamide dimaleate with an X-ray powder diffraction pattern substantially the same as the X-ray powder diffraction pattern shown in FIG. 1.

In the preceding paragraphs defining the X-ray powder diffraction peaks for the crystalline form of the quinazoline derivative of Formula I described herein, the term "at about" is used in the expression "... at about 2-theta=..." to indicate that the precise position of peaks (i.e. the recited 2-theta angle values) should not be construed as being absolute values because, as will be appreciated by those skilled in the art, the precise position of the peaks may vary slightly between one machine and another, from one sample to another, or as a result of slight variations in measurement conditions utilised. It is also stated in the preceding paragraphs that the crystalline form of (2R,4R) 4-({4-[(3-chloro-2-fluorophenyl)amino]-7-methoxyquinazolin-6-yl}oxy)-N,1-dimethylpiperidine-2-carboxamide dimaleate provides the X-ray powder diffraction pattern 'substantially' the same as the X-ray powder diffraction pattern shown in FIG. 1, and have substantially the most prominent peaks (2-theta angle values) shown in Table 1. It shall be appreciated that the use of the term 'substantially' in this context is also intended to indicate that the 2-theta angle values of the X-ray powder diffraction patterns may vary slightly from one machine to another, from one sample to another, or as a result of slight variations in measurement conditions utilised, so the peak positions shown in FIG. 1 or quoted in Table 1 or elsewhere herein are again not to be construed as absolute values.

In this regard, it is known in the art that an X-ray powder diffraction pattern may be obtained which has one or more measurement errors depending on measurement conditions (such as equipment or machine used). In particular, it is generally known that intensities in an X-ray powder diffraction pattern may vary depending on measurement conditions and sample preparation. For example, persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996). Therefore, it shall be understood that the crystalline form of the (2R,4R) 4-({4-[(3-chloro-2-fluorophenyl)amino]-7-methoxyquinazolin-6-yl}oxy)-N,1-dimethylpiperidine-2-carboxamide dimaleate described herein is not limited to crystals that provide X-ray powder diffraction patterns identical to the X-ray powder diffraction patterns shown in FIG. 1, and any crystals of (2R,4R) 4-({4-[(3-chloro-2-fluorophenyl)amino]-7-methoxyquinazolin-6-yl}oxy)-N,1-dimethylpiperidine-2-carboxamide dimaleate which provide X-ray powder diffraction patterns substantially the same as those shown in FIG. 1 fall within the scope of the present invention. A person skilled in the art of X-ray powder diffraction is able to judge the substantial identity of X-ray powder diffraction patterns.

Generally, a measurement error of a diffraction angle in an X-ray powder diffractogram is about 2-theta=0.5° or less, and such degree of a measurement error should be taken into account when considering the X-ray powder diffraction patterns in FIG. 1, and when interpreting the peak positions referred to in the text above and in Table 1.

The crystalline (2R,4R) 4-({4-[(3-chloro-2-fluorophenyl)amino]-7-methoxyquinazolin-6-yl}oxy)-N,1-dimethylpiperidine-2-carboxamide dimaleate has a melting endotherm with an onset temperature in the range of about 175 to 182° C., as determined by differential scanning calorimetry (DSC) analysis. The peak of the melting endotherm is typically in the range of about 180 to 187° C., as determined by DSC analysis.

According to a further aspect of the invention there is provided crystalline (2R,4R) 4-({4-[(3-chloro-2-fluorophenyl)amino]-7-methoxyquinazolin-6-yl}oxy)-N,1-dimethylpiperidine-2-carboxamide dimaleate with a melting endotherm with an onset temperature in the range of about 175° C. to 182° C., as determined by DSC analysis.

According to a further aspect of the invention there is provided crystalline (2R,4R) 4-({4-[(3-chloro-2-fluorophenyl)amino]-7-methoxyquinazolin-6-yl}oxy)-N,1-dimethylpiperidine-2-carboxamide dimaleate with a melting endotherm with a peak temperature in the range of about 180° C. to 187° C. as determined by DSC analysis.

It will be understood that the onset and/or peak temperature values determined by DSC analysis may vary slightly from one machine to another, one method to another or from one sample to another, and so the values quoted are not to be construed as absolute. Generally measurement error of characteristic temperatures in DSC analysis is dependent upon the heating rate used. However, at a heating rate of about 10° C./minute a measurement error of about ±5° C. or less is typical.

It is to be understood that, insofar as certain of the quinazoline derivatives of formula I defined above may exist in optically active or racemic forms by virtue of one or more asymmetric carbon atoms. The invention includes in its definition any such optically active or racemic form which possesses the above-mentioned activity of the compounds of the invention.

In particular, the quinazoline derivative of formula I has 2 chiral centers on the piperidinyl ring (the oxygen linker at the 4-position and the $R^3R^4NC(O)$— group at the 2-position). The present invention encompasses all such stereoisomers having activity as herein described, for example the (2R,4R), (2S,4S), (2S,4R) and (2R,4S) isomers. It is further to be understood that in the names of chiral compounds (R,S) denotes any scalemic or racemic mixture while (R) and (S) denote the specific enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ratio 50:50. The synthesis of optically active forms may be carried out by standard techniques of organic chemistry well known in the art, for example by synthesis from optically active starting materials or by resolution of a racemic form.

In this specification the generic term "alkyl" includes both straight-chain and branched-chain alkyl groups such as propyl, isopropyl and tert-butyl. However references to individual alkyl groups such as "propyl" are specific for the straight-chain version only, references to individual branched-chain alkyl groups such as "isopropyl" are specific for the branched-chain version only.

Suitable values for any of various groups defined hereinbefore or hereafter in this specification include:—
for halogeno fluoro, chloro, bromo and iodo;
for (1-4C)alkyl: methyl, ethyl, propyl, isopropyl, n-butyl, tert-butyl and iso-butyl.

As will be understood, references herein to the anilino group in the quinazoline of formula I refer to the group located at the 4-position of the quinazoline ring of the formula:

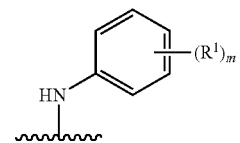

Synthesis of Quinazoline Derivatives of the Formula I

A further aspect the present invention provides a process for preparing a quinazoline derivative of formula I or a pharmaceutically-acceptable salt thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, hydroxy or carboxy it may be desirable to protect the group in some of the reactions mentioned herein. Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl).

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl (for example α-methylbenzyl), 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); lower alkanoyloxyalkyl groups (for example pivaloyloxymethyl); trialkylsilyl (for example trimethylsilyl and tert-butyldimethylsilyl); alkylidene (for example methylidene) and benzylidene and substituted benzylidene groups.

The protecting groups may be removed at any convenient stage in the synthesis using conventional techniques well known in the chemical art. Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl. For example an acyl protecting group such as an alkanoyl or alkoxycarbonyl group or an aroyl group may, for example, be removed by hydrolysis with a suitable base such as an alkali metal hydroxide, for example lithium or sodium hydroxide. Alternatively an acyl protecting group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris (trifluoroacetate). Methods particularly appropriate for the removal of carboxyl protecting groups include for example acid-, base-, metal- or enzymically-catalysed cleavage.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

A quinazoline derivative of the formula I, or a pharmaceutically acceptable salt thereof, may be prepared by any process known to be applicable to the preparation of chemically-related compounds, for example using analogous processes to those described in WO 03/082831. Such processes, when used to prepare a quinazoline derivative of the formula I, or a pharmaceutically-acceptable salt thereof, are provided as a further feature of the invention and are illustrated by the following representative process variants. Necessary starting materials may be obtained by standard procedures of organic chemistry (see, for example, Advanced Organic Chemistry (Wiley-Interscience), Jerry March). The preparation of such starting materials is described within the accompanying non-limiting Examples. Alternatively, necessary starting materials are obtainable by analogous procedures to those illustrated which are within the ordinary skill of an organic chemist.

In the following processes for the preparation of quinazoline derivatives of the formula I, or pharmaceutically acceptable salts thereof, the variables are as defined above unless stated otherwise.

Process (a):

the reaction of a compound of the formula II or reactive derivative thereof:

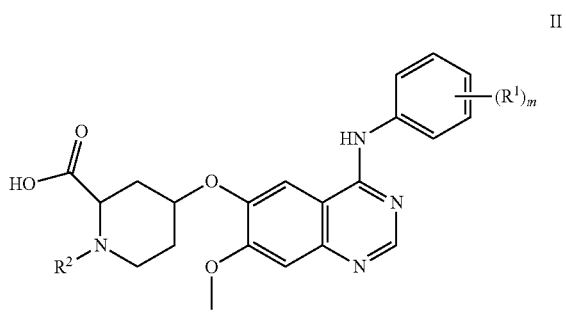

II wherein $R^1$, $R^2$ and m have any of the meanings defined hereinbefore, and wherein any functional group in the compound of formula II is protected if necessary, with a compound of the formula $NH_2R^4$, or a suitable salt thereof, wherein $R^4$ is as hereinbefore defined; or Process (b)
the alkylation of a compound of the formula I':

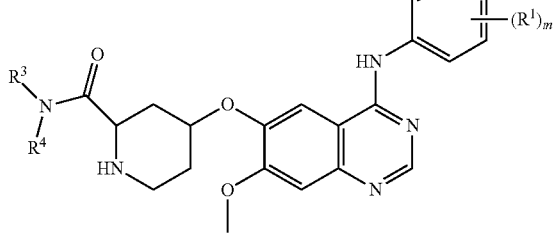

I' wherein $R^1$, $R^3$, $R^4$ and m have any of the meanings defined hereinbefore, and wherein any functional group in the compound of formula I' is protected if necessary; or Process (c)
by reacting a compound of the formula III:

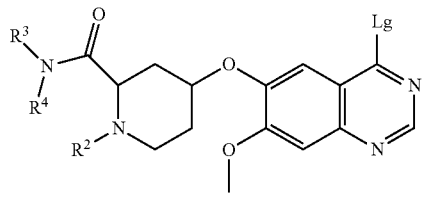

III wherein Lg is a suitable displaceable group; and $R^2$, $R^3$ and $R^4$ are as hereinbefore defined, and wherein any functional group in the compound of formula III is protected if necessary,
with a compound of the formula IV:

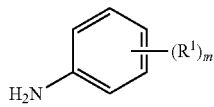

IV wherein $R^1$ and m are as hereinbefore defined; or
Process (d)
by reacting a compound of the formula V:

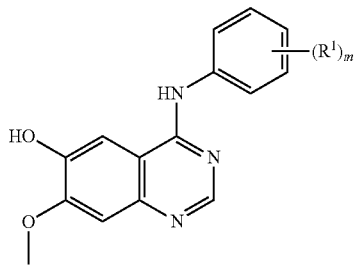

V wherein $R^1$ and m are as hereinbefore defined, and wherein any functional group in the compound of formula V is protected if necessary, with a compound of the formula VI:

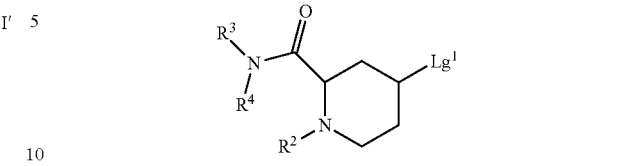

VI wherein $Lg^1$ is a displaceable group and $R^2$, $R^3$ and $R^4$ are as hereinbefore defined, and wherein any functional group in the compound of formula VI is protected if necessary; and thereafter, if necessary (in any order):
(i) removing any protecting groups; and
(ii) forming a pharmaceutically acceptable salt of the quinazoline derivative of formula I.

Specific conditions for the above reactions are as follows.
Reaction Conditions for Process (a)

The reaction is conveniently carried out in the presence of a suitable coupling agent, such as a carbodiimide, or a suitable peptide coupling agent, for example O-(7-azabenzotriazol-1-yl)-N,N,N',N'-tetramethyluronium hexafluoro-phosphate (HATU) or a carbodiimide such as dicyclohexylcarbodiimide, optionally in the presence of a catalyst such as dimethylaminopyridine or 4-pyrrolidinopyridine.

The coupling reaction is conveniently carried out in the presence of a suitable base. A suitable base is, for example, an organic amine base such as, for example, pyridine, 2,6-lutidine, collidine, 4-dimethylaminopyridine, triethylamine, di-isopropylethylamine, N-methylmorpholine or diazabicyclo[5.4.0]undec-7-ene, or, for example, an alkali or alkaline earth metal carbonate, for example sodium carbonate, potassium carbonate, cesium carbonate or calcium carbonate.

The reaction is conveniently carried out in the presence of a suitable inert solvent or diluent, for example an ester such as ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethyl acetamide, N-methylpyrrolidin-2-one or dimethylsulfoxide. The reaction is conveniently carried out at a temperature in the range, for example, from 0 to 120° C., conveniently at or near ambient temperature.

A "reactive derivative" of the acid of the formula II is a carboxylic acid derivative that will react with the amine of the formula $NH_2R^4$ to give the corresponding amide. A suitable reactive derivative of a carboxylic acid of the formula II is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; or an acyl azide, for example an azide formed by the reaction of the acid and azide such as diphenylphosphoryl azide; an acyl cyanide, for example a cyanide formed by the reaction of an acid and a cyanide such as diethylphosphoryl cyanide. The reaction of such reactive derivatives of carboxylic acid with amines is well known in the art, for example they may be reacted in the presence of a base, such as those described above, and in a suitable solvent, such as those described above. The reaction may conveniently be performed at a temperature as described above.

Preparation of Starting Materials for Process (a)

Compounds of formula II may be prepared using conventional techniques or analogous processes to those described in the prior art for the preparation of similar compounds, for example the methods described in WO 03/082831. For example, the compounds of formula II may be prepared in accordance with Reaction Scheme 1:

zodicarboxylate in an organic solvent such as THF or suitably dichloromethane and in the temperature range −15° C. to 60° C., but suitably at or near ambient temperature. A suitable tertiary phosphine includes for example tri-n-butylphosphine or particularly tri-phenylphosphine. A suitable di-alkylazodicarboxylate includes for example diethyl azodicarboxylate (DEAD) or di-tert-butyl azodicarboxylate (DTAD). Details of Mitsunobu reactions are contained in Tet. Letts., 31, 699, (1990); The Mitsunobu Reac-

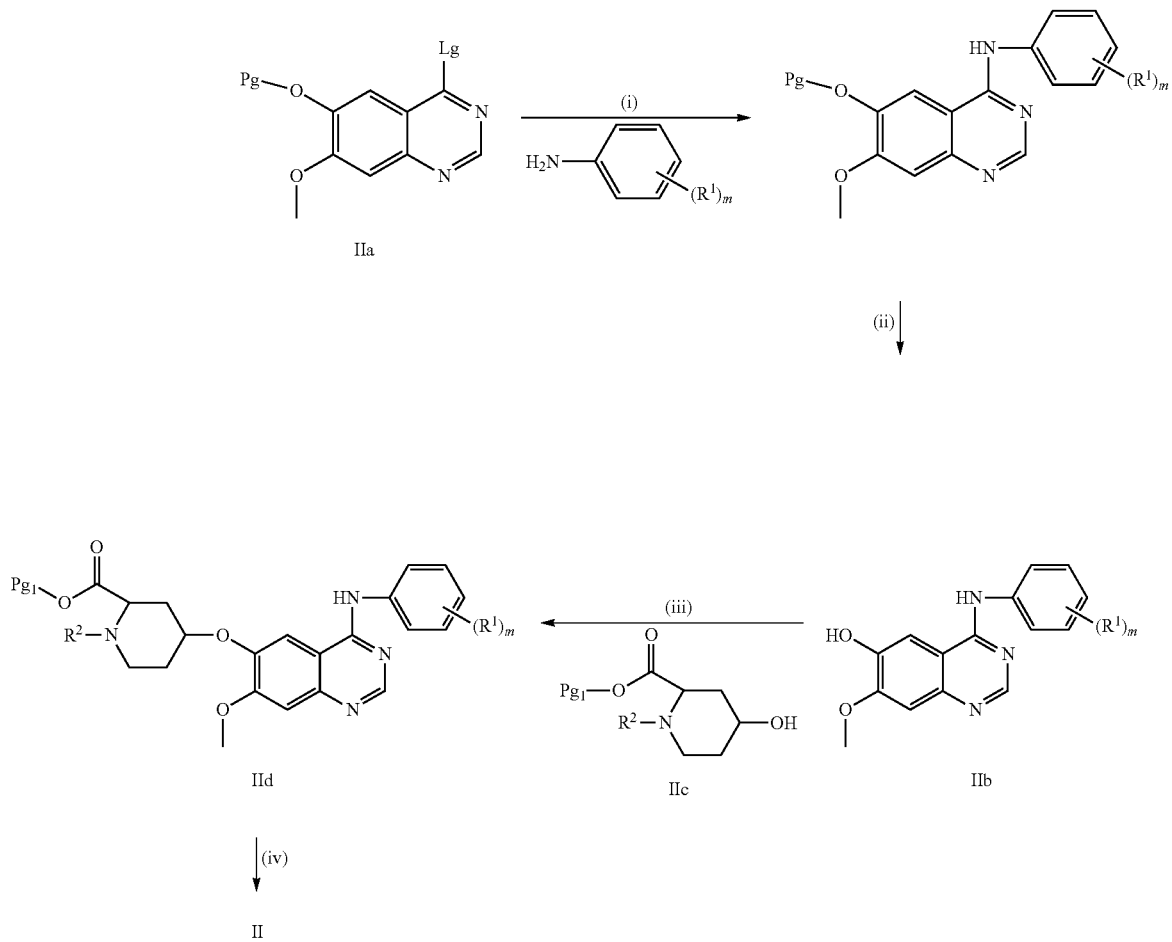

Reaction Scheme 1 wherein $R^1$, $R^2$ and m are as hereinbefore defined; Lg is a suitable displaceable group, such as halogeno (for example chloro), Pg is a suitable hydroxy protecting group, such as an alkanoyl group; and $Pg^1$ is a suitable carboxy protecting group such as (1-4C)alkyl, and wherein any functional group in the compounds shown in Reaction Scheme 1 is protected if necessary.

Notes for Reaction Scheme 1

Step (i): Reaction suitably carried out under analogous conditions to those described herein in relation to Process (c).

Step (ii): Cleavage of Pg may be performed under standard conditions for such reactions. For example when Pg is an alkanoyl group such as acetyl, it may be cleaved by heating in the presence of a methanolic ammonia solution.

Step (iii): Coupling using the Mitsunobu reaction. Suitable Mitsunobu conditions include, for example, reaction in the presence of a suitable tertiary phosphine and a di-alkylation, D. L. Hughes, Organic Reactions, 1992, Vol. 42, 335-656 and Progress in the Mitsunobu Reaction, D. L. Hughes, Organic Preparations and Procedures International, 1996, Vol. 28, 127-164. If desired, particular stereoisomers of compounds of formula IIc may be employed, to produce particular stereoisomers of compounds of formula I.

Step (iv) Removal of the carboxy protecting group $Pg^1$ using conventional methods. For example when $Pg^1$ is (1-4C) alkyl, by hydrolysis of the ester of formula IId using well known techniques, for example alkaline hydrolysis in the presence of a suitable base such as lithium hydroxide.

Compounds of formulae IIa and IIc are known or can be prepared using known processes for the preparation of analogous compounds. For example compounds of the formula IIa wherein Lg is chloro and Pg is acetyl may be prepared using the process illustrated in Reaction Scheme 2:

Reaction scheme 2
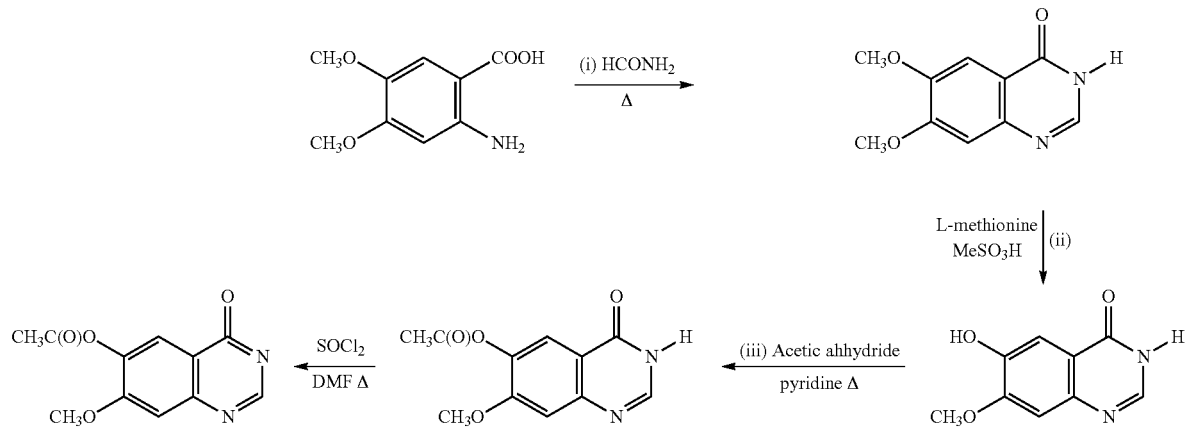
Optical isomers of the formula IIc, may for example, be prepared using conventional methods such as that shown in Reaction Scheme 2a:
Reaction Scheme 2a
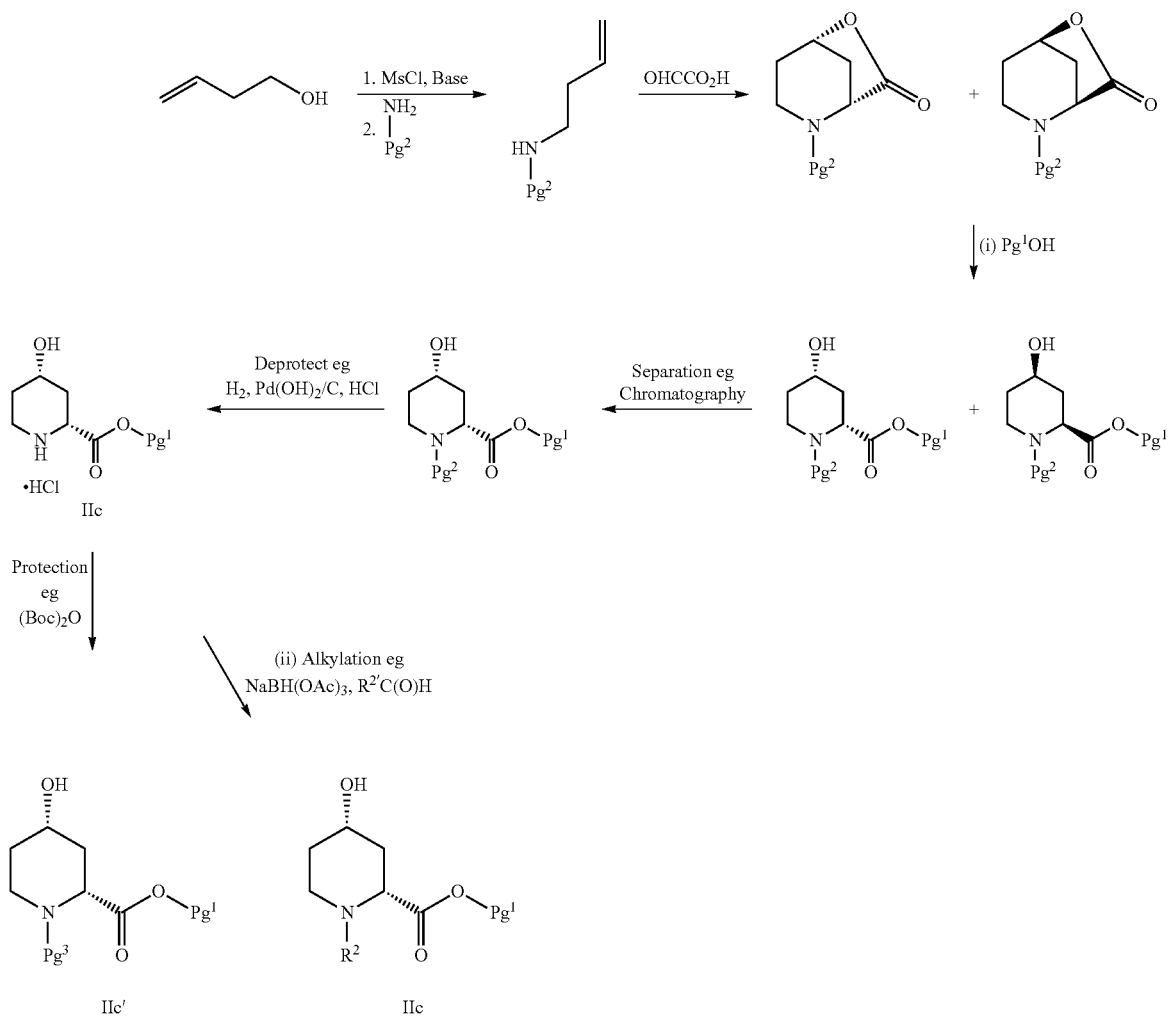

wherein $Pg^1$ is alkyl such as methyl; $NaBH(OAc)_3$ is sodium triacetoxyborohydride; MsCl is mesyl chloride; $Pg^2$ is a suitable amino protecting group such as benzyl or α-methylbenzyl, for example (S)-α-methylbenzyl or (R)-α-methylbenzyl; $Pg^3$ is a suitable nitrogen protecting group such as tert-butoxycarbonyl (BOC); $R^2$ is as hereinbefore defined and $R^{2'}$ represents hydrogen or (1-3C)alkyl, and wherein any functional group in the compounds shown in Reaction Scheme 2a is protected if necessary.

Notes for Reaction Scheme 2a (i) The lactone may be reacted with a suitable alcohol of the formula $Pg^1OH$ such as an alkyl alcohol (for example methanol) in the presence of an acid, for example HCl in a suitable solvent such as dioxane. Suitably the reaction is performed at elevated temperature, for example under reflux.

(ii) As will be realised, in Reaction Scheme 2a when the alkylation of the piperidine is via a reductive amination, reaction of the piperidine using the appropriate aldehyde of the formula $R^{2'}C(O)H$ gives a compound of the formula IIc in which $R^2$ is (1-4C)alkyl. Suitable conditions for the reductive amination are as described in relation to Process (b).

As will be realised the method in Reaction Scheme 2a showing the preparation of the (2R,4S) piperidine isomers can also be used to prepare the (2S,4R) isomer by isolating the alternative isomer following ring opening of the lactone shown in Reaction Scheme 2a.

Removal of the amino protecting group $Pg^2$ may be achieved using conventional methods. For example when $Pg^2$ is benzyl or α-methylbenzyl the protecting group may be removed by hydrogenation in the presence of a suitable catalyst, as illustrated above in Reaction Scheme 2a.

Conveniently, compounds of the formula IIc wherein $R^2$ is (1-4C)alkyl may also be prepared using Reaction Scheme 2b:

Reaction Scheme 2b

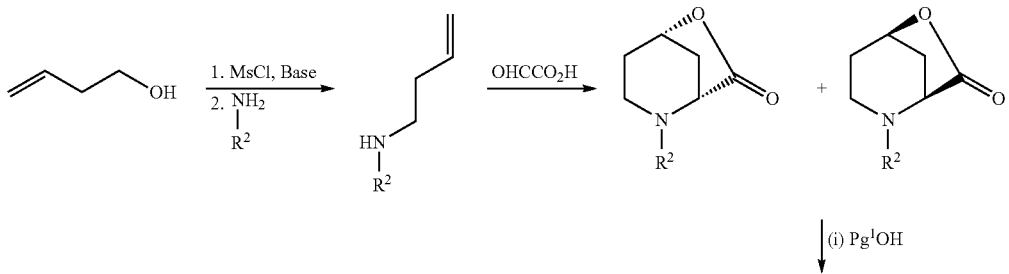

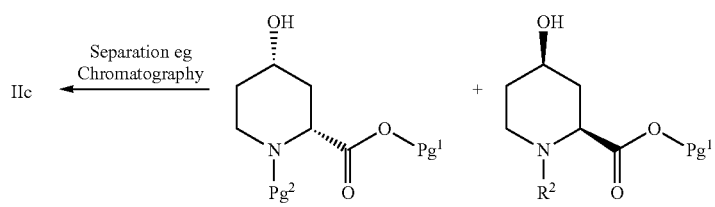

wherein Pg¹ is a carboxy protecting group such alkyl (for example methyl); MsCl is mesyl chloride; and R² represents (1-4C)alkyl, and wherein any functional group in the compounds shown in Reaction Scheme 2a is protected if necessary.

The lactones prepared in Reaction Schemes 2a and 2b may be synthesised using known methods, for example as described in Skiles et al. Bioorganic & Medicinal Chemistry Letters (1996), 6(8), 963-966; and Gillard et al. Journal of Organic Chemistry (1996), 61(6), 2226-31.

Compounds of the formula IIc wherein Pg¹ is alkyl may also be prepared by esterification of the corresponding commercially available 4-hydroxypiperidine-2-carboxylic acid.

Alternatively compounds of the formula II may be prepared according to Reaction Scheme 1a:

Reaction Scheme Ia:

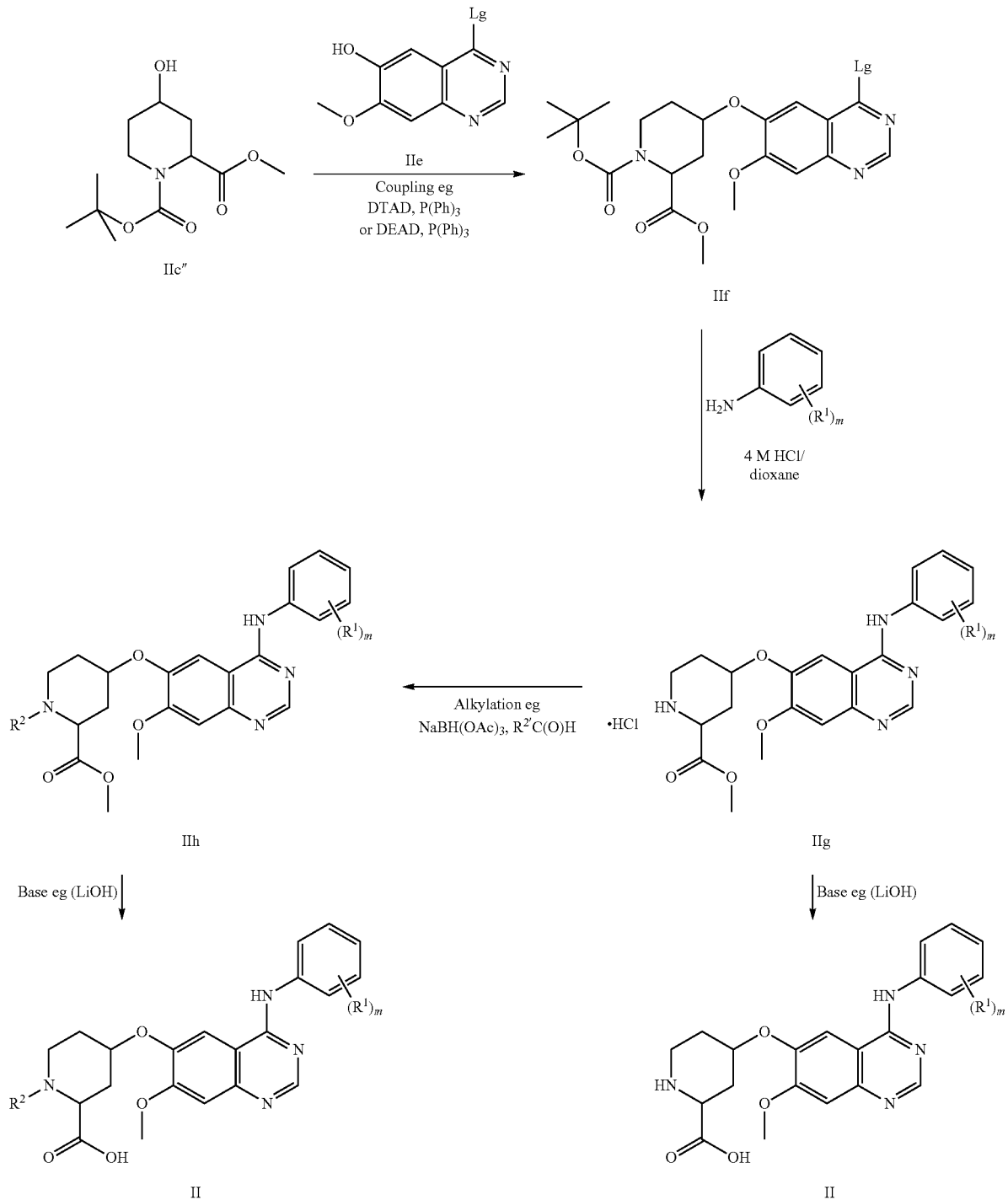

wherein Lg is a displaceable group as hereinbefore defined in relation to Reaction Scheme 1 (for example halogeno such as chloro); $R^{2'}$ is hydrogen or (1-3C)alkyl; and $R^1$, $R^2$ and $R^4$ are as hereinbefore defined, and wherein any functional group in the compounds shown in Reaction Scheme 1a is protected if necessary.

The compound of formula IIc" shown in Reaction Scheme 1a is a compound of the formula IIc' described in Reaction Scheme 2a wherein $Pg^1$ is methyl and $Pg^3$ is a tert-butyloxycarbonyl (BOC) group. If required, other suitable protecting groups may be used in place of the methyl and BOC group shown in Reaction Scheme 1a.

As will be realised, Reaction Scheme 1a may be used to prepare particular stereoisomers of compounds of the formula II by using the appropriate chiral starting material of the compound of formula IIc". For example using the (2R,4S) piperidine of the formula IIc" shown in Reaction Scheme 2a would give the (2R,4R) piperidine isomer of the compound of formula II shown in Reaction Scheme 1a.

The compound of formula IIe shown in Reaction Scheme 1a may be prepared using known methods, for example by removal of the protecting group Pg from the compound of formula IIa shown in Reaction Scheme 1 using conventional methods.

Reaction Conditions for Process (b)

A suitable alkylating agent is, for example, any agent known in the art for the alkylation of amino to alkylamino, such as an alkyl halide, for example a (1-6C)alkyl chloride, bromide or iodide, conveniently in the presence of a suitable base as defined hereinbefore, in a suitable inert solvent or diluent and at a temperature in the range, for example, 10 to 140° C., conveniently at or near ambient temperature.

Alternatively compounds of the formula I' may be alkylated via a reductive amination reaction using a suitable aldehyde, for example formaldehyde (or paraformaldehyde), or a (2-3C)alkanoylaldehyde (for example acetaldehyde or propionaldehyde) in the presence of a suitable reducing agent. For example, for the production of those compounds of the formula I wherein $R^2$ is methyl, the corresponding compound for formula I' may be reacted with formaldehyde in the presence of a suitable reducing agent. A suitable reducing agent for use in the reductive amination reaction is, for example, a hydride reducing agent, for example formic acid, an alkali metal aluminium hydride such as lithium aluminium hydride, or suitably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is suitably performed under acidic conditions in the presence of a suitable acid such as hydrogen chloride or acetic acid, a buffer may also be used to maintain pH at the desired level during the reaction. The reaction is performed at a temperature in the range, for example, 10 to 100° C., such as 70 to 90° C. or, conveniently, at or near ambient temperature. Alternatively, following reaction with the aldehyde, the reduction of the resulting compound may be effected by hydrogenation, for example hydrogenation in the presence of a suitable catalyst such as a palladium on carbon catalyst.

Preparation of Starting Materials for Process (b)

Compounds of the formula I' may be prepared using an analogous process to that described in Reaction Scheme 1 except $R^2$ in the compound of formula IIc is replaced by a suitable amine protecting group, for example a tert-butoxycarbonyl (BOC) group. The resulting carboxylic acid may then be converted to the required amide using Process (a) described above. The amine protecting group may be removed following conversion of the acid to the amide by conventional means. For example when the amine protecting group is a BOC group by treating the compound with a suitable acid such as trifluoroacetic acid.

Reaction Conditions for Process (c)

Lg is a suitable displaceable group for example halogeno, such as chloro.

The reaction is conveniently carried out in the presence of a suitable inert solvent or diluent, for example an alcohol or ester such as, isopropanol or ethyl acetate, a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one acetonitrile or dimethylsulfoxide; acetonitrile is favoured. The reaction is conveniently carried out at a temperature in the range, for example, 10 to 250° C., conveniently in the range 40 to 120° C. or where a solvent or diluent is used at the reflux temperature. Conveniently, the compound of formula III may be reacted with a compound of the formula IV in the presence of a protic solvent such as isopropanol, conveniently in the presence of an acid, for example hydrogen chloride gas in diethyl ether or dioxane, or hydrochloric acid, for example a 4M solution of hydrogen chloride in dioxane, under the conditions described above. Alternatively, this reaction may be conveniently carried out in an aprotic solvent, such as dioxane or a dipolar aprotic solvent such as N,N-dimethylacetamide or acetonitrile in the presence of an acid, for example hydrogen chloride gas in diethyl ether or dioxane, or hydrochloric acid. The compound of the formula III, wherein Lg is halogeno, may be reacted with a compound of the formula IV in the absence of an acid. In this reaction displacement of the halogeno leaving group Lg results in the formation of the acid HLg in-situ and auto-catalysis of the reaction. Conveniently the reaction is carried out in a suitable inert organic solvent, for example isopropanol, dioxane or N,N-dimethylacetamide. Suitable conditions for this reaction are as described above.

Alternatively, the compound of formula III may be reacted with a compound of the formula IV in the presence of a suitable base. Suitable bases for this reaction are as hereinbefore defined under Process (a). This reaction is conveniently performed in an inert solvent or diluent, for example those mentioned above in relation to this process (a).

Preparation of Starting Materials for Process (c)

Compounds of formula III are may be prepared using conventional techniques or analogous processes to those described in the prior art for the preparation of similar is compounds. For example, the compounds of formula III may be prepared in accordance with Reaction Scheme 3:

Reaction Scheme 3
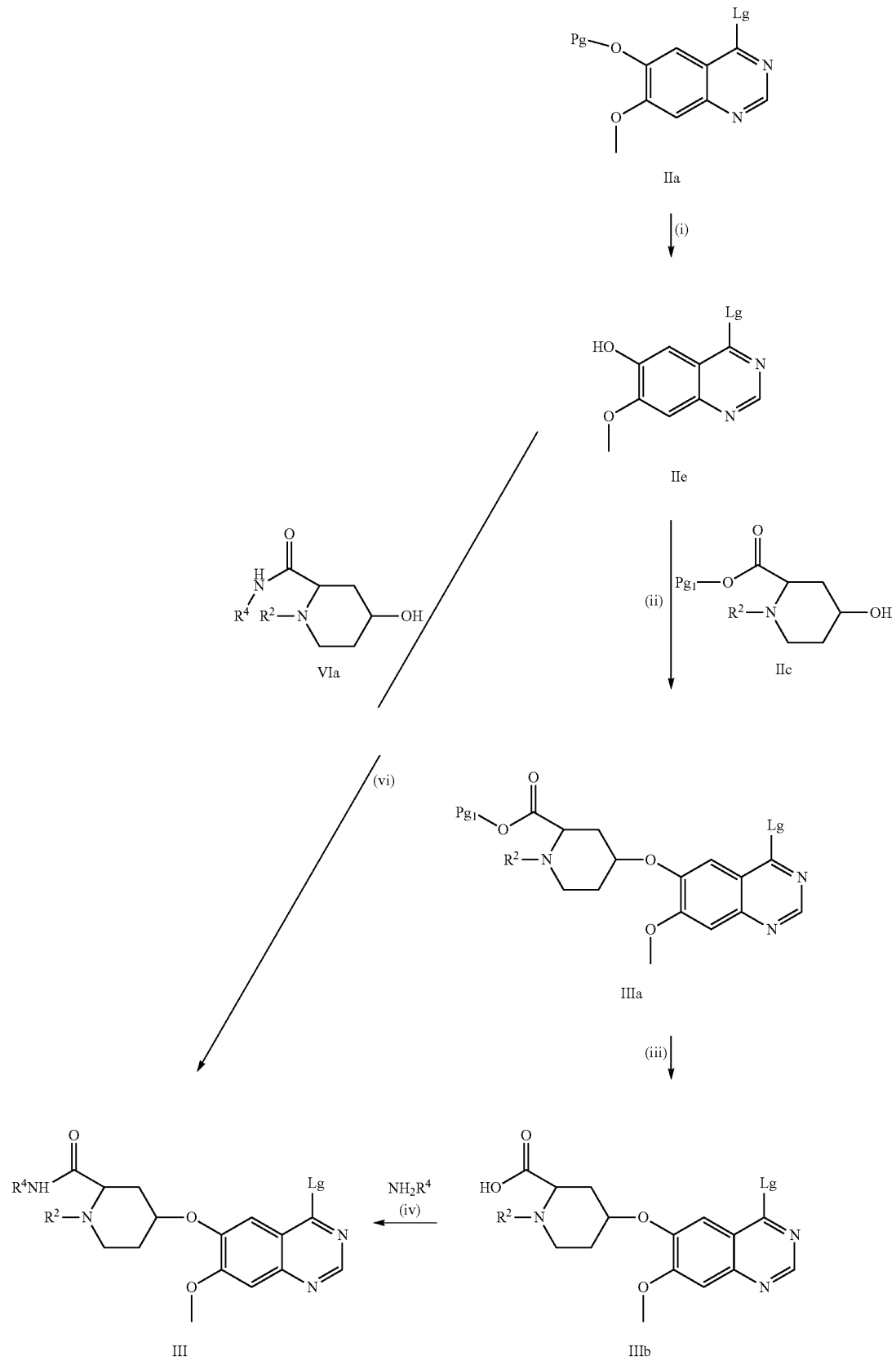

wherein $R^2$ and $R^4$ as hereinbefore defined; Lg is a suitable displaceable group, such as halogeno, for example chloro; Pg is a suitable hydroxy protecting group, such as acetyl; and $Pg^1$ is a suitable carboxy protecting group such as (1-4C)alkyl.

Notes for Reaction Scheme 3

Step (i): Removal of Pg under analogous conditions to those described for Step (ii) of Reaction Scheme 1.

Step (ii): Mitsunobu coupling under analogous conditions to Step (iii) of Reaction Scheme 1.

Step (iii): Removal of carboxy protecting group under analogous conditions to Step (iv) of Reaction Scheme 1.

Step (iv): Amide formation using analogous conditions to those described above for Process (a).

Step (vi): Coupling for example using Mitsunobu conditions as described in relation to step (iii) of Reaction Scheme 1. Alternatively, the piperidine compound of formula VIa may be first converted to a compound of formula VI as described below in Reaction Scheme 4 below to give a displaceable group on the piperidine ring which is then reacted with the compound of formula IIe using analogous conditions to those describe for process (d).

Compounds of the formula VIa may be prepared using, for example, the method described in Reaction Scheme 4 below.

Reaction Conditions for Process (d)

A convenient displaceable group Lg is, for example, a halogeno, alkanesulfonyloxy or arylsulfonyloxy group, for example a chloro, bromo, methanesulfonyloxy, 4-nitrobenzenesulfonyloxy or toluene-4-sulfonyloxy group, particularly a methanesulfonyloxy, 4-nitrobenzenesulfonyloxy or toluene-4-sulfonyloxy group.

The reaction is advantageously carried out in the presence of base. A suitable base is, for example, an organic amine base such as, for example, pyridine, 2,6-lutidine, collidine, 4-dimethylaminopyridine, triethylamine, N-methylmorpholine or diazabicyclo[5.4.0]undec-7-ene, or for example, an alkali metal or alkaline earth metal carbonate or hydroxide, for example sodium carbonate, potassium carbonate, cesium carbonate, calcium carbonate, sodium hydroxide or potassium hydroxide. Alternatively such a base is, for example, an alkali metal hydride, for example sodium hydride, an alkali metal or alkaline earth metal amide, for example sodium amide or sodium bis(trimethylsilyl)amide, or a sufficiently basic alkali metal halide, for example cesium fluoride or sodium iodide. The reaction is suitably effected in the presence of an inert solvent or diluent, for example an alkanol or ester such as methanol, ethanol, 2-propanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or (suitably) a dipolar aprotic solvent such as N,N-dimethylformamide, N,N-dimethylacetamide, N-methylpyrrolidin-2-one or dimethylsulfoxide. The reaction is conveniently effected at a temperature in the range, for example, 10 to 150° C. (or the boiling point of the solvent), suitably in the range 20 to 90° C.

Preparation of Starting Materials for Process (d)

Compounds of the formula V may be prepared using analogous processes to those described in WO 03/082831, for example as described in Reference Example 2.

Compounds of the formula VI may be prepared by conventional methods, for example a compound of the formula VI wherein $R^4$ is hydrogen and $Lg^1$ is a mesylate group, may be prepared using the process illustrated in Reaction Scheme 4:

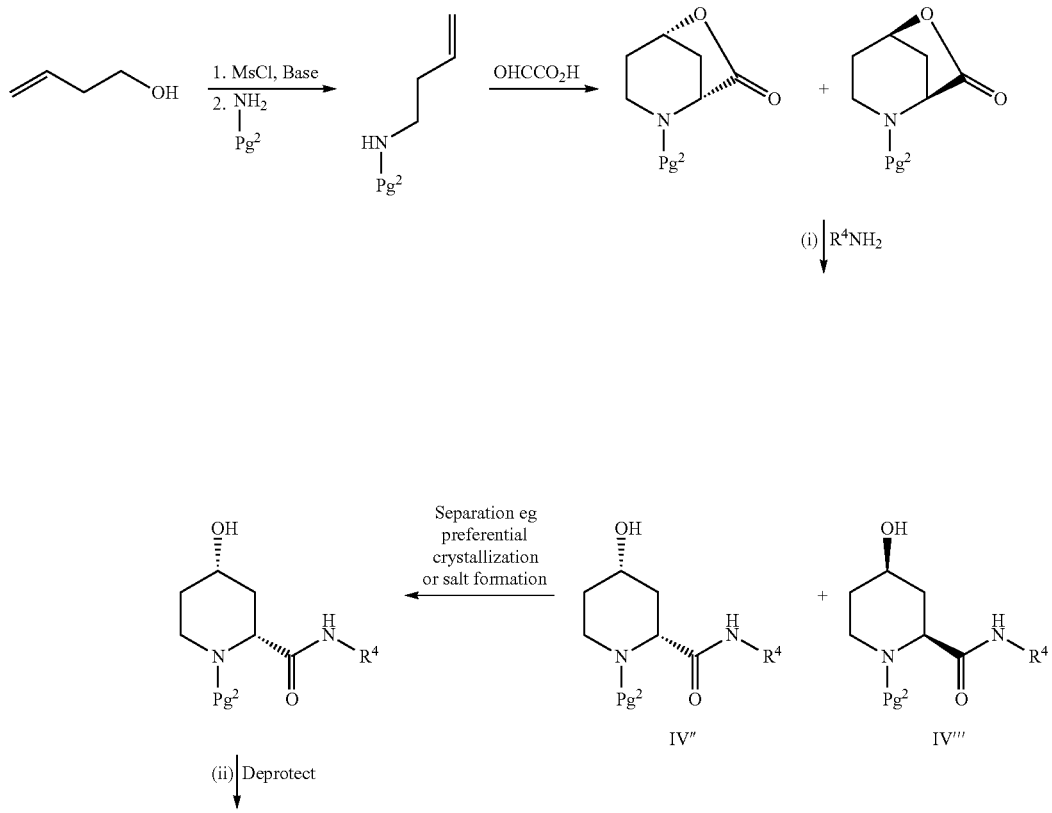

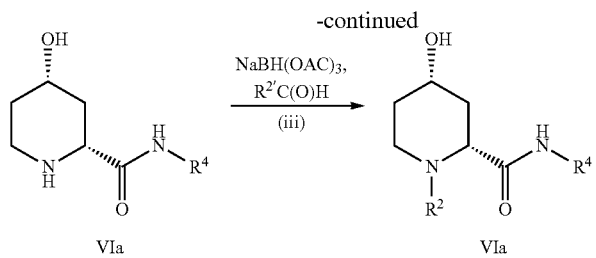

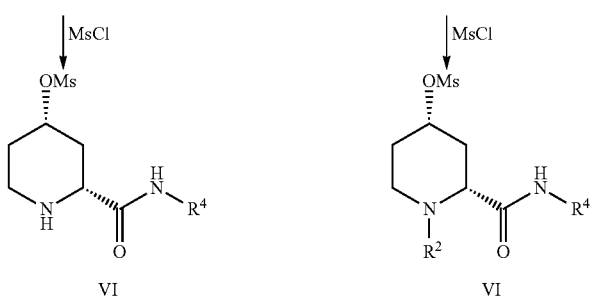

wherein $Pg^2$ is a suitable amino protecting group as defined hereinbefore in relation to Reaction Scheme 2a; $R^{2'}$ is hydrogen or (1-3C)alkyl; MSCl is mesyl; and $R^1$, $R^2$ and $R^4$ are as hereinbefore defined, and wherein any functional group in the compounds shown in Reaction Scheme 4 is protected if necessary.

Notes for Reaction Scheme 4

(i) reaction with amine of the formula $R^4NH_2$ a suitable solvent, for example an ether such as tetrahydrofuran. Alternatively, the amine can be reacted with a Grignard reagent such as isopropylmagnesium chloride in a suitable solvent such as tetrahydrofuran then reacted with the lactones as described in J. Org. Chem., 1997, vol 62, p3440.

(ii) Deprotection under standard conditions. For example when $Pg^2$ is benzyl or α-methylbenzyl by catalytic hydrogenation.

(iii) Alkylation, such as reductive amination under standard conditions, for example as described in relation to Process (b).

Alternatively compounds of the formula VIa wherein $R^2$ is (1-4C)alkyl may be prepared using Reaction Scheme 4a:

Reaction Scheme 4a

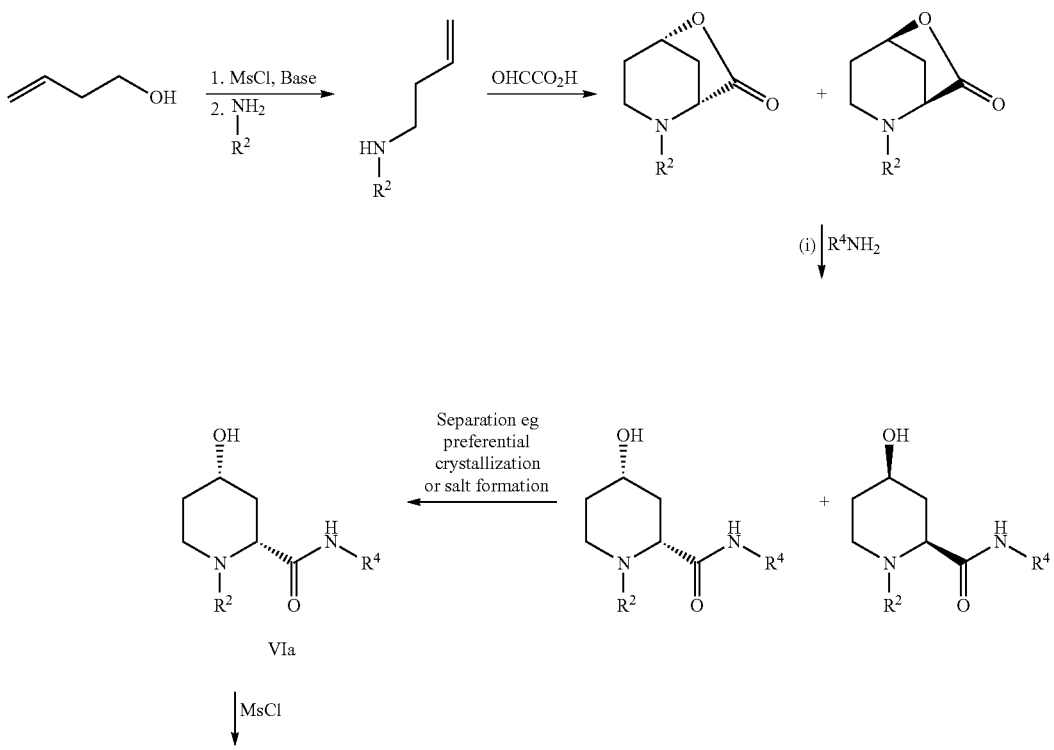

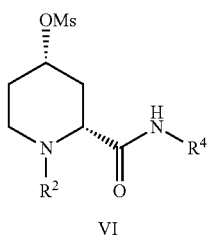

VI wherein $R^2$ is (1-4C)alkyl; MsCl is mesyl chloride; and $R^4$ is as hereinbefore defined, and wherein any functional group in the compounds shown in Reaction Scheme 4a is protected if necessary.

Notes for Reaction Scheme 9a (i) As for note (i) in Reaction Scheme 4.

The lactones shown is Reaction Schemes 4 and 4a may be prepared as described herein in relation to Reaction Scheme 2a.

As will be realised the methods in Reaction Schemes 4 and 4a show the preparation of one specific stereoisomer. The same method may also be used to alternative piperidine isomer by isolating the alternative isomer following ring opening of the lactone.

Conveniently, the compound of formula VI used as the starting material in Process (d) may be generated in-situ in Process (d) starting from a compound of the formula VIa by reacting a compound of the formula VIa with, for example, a suitable sulfonyl halide such as mesyl chloride or tosyl chloride. The resulting compound of formula VI is then reacted with a compound of formula V as described above for Process (d).

When a pharmaceutically-acceptable salt of a quinazoline derivative of the formula I is required, for example an acid-addition salt, it may be obtained by, for example, reaction of said quinazoline derivative with a suitable acid using a conventional procedure. Methods for the preparation of pharmaceutically acceptable salts are well known in the art and are illustrated in the examples of the present application. For example, following reaction of a quinazoline derivative of the formula I with an acid, the required acid addition salt may be precipitated from solution by supersaturating the solution containing the quinazoline derivative of the formula I. Super saturation may be achieved using well-known techniques, for example by cooling the solution, by removing solvent by evaporation or by the addition of a suitable anti-solvent to precipitate the salt.

To facilitate isolation of a quinazoline derivative of the formula I during its preparation, the compound may be prepared in the form of a salt that is not a pharmaceutically acceptable salt. The resulting salt can then be modified by conventional techniques to give a pharmaceutically acceptable salt of the compound. Such salt modification techniques are well known and include, for example ion exchange techniques or re-precipitation of the compound from solution in the presence of a pharmaceutically acceptable counter ion as described above, for example by re-precipitation in the presence of a suitable pharmaceutically acceptable acid to give the required pharmaceutically acceptable acid addition salt of a quinazoline derivative of the formula I.

In a particular embodiment a maleate salt of a quinazoline derivative of the formula I (for example (2R,4R)-4-({4-[(3-chloro-2-fluorophenyl)amino]-7-methoxyquinazolin-6-yl}oxy)-N,1-dimethylpiperidine-2-carboxamide dimaleate) may be prepared by contacting the free base form of the quinazoline derivative with maleic acid. Conveniently, the free base is first dissolved in a suitable solvent such as acetonitrile and is contacted with the required quantity of maleic acid to give the desired salt (for example a molar ratio of maleic acid:quinazoline derivative of formula I of about 2:1, or a slightly higher molar excess of maleic acid, would give the dimaleate salt). The salt may be precipitated from the solution by supersaturating the solution as described herein for example by evaporating solvent and/or cooling the solution. When a crystalline salt is required for example crystalline (2R,4R)-4-({4-[(3-chloro-2-fluorophenyl)amino]-7-methoxyquinazolin-6-yl}oxy)-N,1-dimethylpiperidine-2-carboxamide dimaleate, re-crystallisation of the dimaleate salt from a suitable organic solvent may be required. For example, the dimaleate salt may be slurried in an organic solvent to promote crystallisation. A suitable organic solvent for the slurrying is, for example an organic ester solvent, such as ethyl acetate. The slurrying is conveniently carried out at elevated temperature, for example from 40 to 60° C., such as about 50° C. Suitably the slurrying is performed over a period of 1 hour to 3 days. If required, crystallisation may be promoted by supersaturating the organic solvent. Supersaturation may be carried out as hereinbefore described, for example by concentrating the mixture by removing a proportion of the solvent (for example by evaporation) and/or cooling of the mixture. Following crystallisation the crystalline dimaleate salt may be isolated using conventional methods such as filtration and drying.

Stereoisomers of quinazoline derivatives of formula I may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. When a specific stereoisomer is isolated it is suitably isolated substantially free from other stereoisomers, for example containing less than 20%, particularly less than 10% and more particularly less than 5% by weight of other stereoisomers.

In the process section above and hereafter, the expression "inert solvent" refers to a solvent which does not react with the starting materials, reagents, intermediates or products in a manner which adversely affects the yield of the desired product.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

Certain novel intermediates utilised in the above processes are provided as a further feature of the present invention together with the process for their preparation. Thus the invention further provides a compound of formulae I', II, IId, IIf, IIg, IIh, III, IIIa and IIIb as defined above. Particular intermediates of the formulae I', II, IId, IIg and IIh are those wherein the group of sub-formula (I)

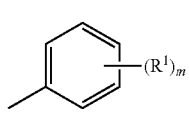
(i)

is 3-chloro-2-fluorophenyl or 3-bromo-2-fluorophenyl, more particularly 2-fluoro-3-chlorophenyl.

Further novel intermediates used in the processes described herein include a compound selected from a compound of the formula (IV'), (VIa) and (VI) and stereoisomers thereof:

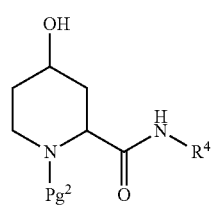
IV'

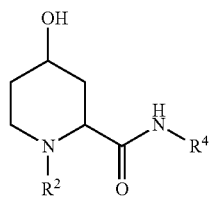
VIa

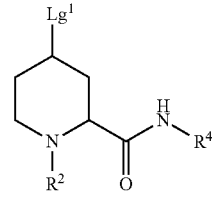
VI wherein $R^2$ and $R^4$ are as hereinbefore defined; $Pg^2$ is a suitable amine protecting group, for example benzyl or substituted benzyl, particularly α-methylbenzyl, for example (S)-α-methylbenzyl or (R)-α-methylbenzyl; and $Lg^1$ is a displaceable group as hereinbefore defined, such as a halogeno, alkanesulfonyloxy or arylsulfonyloxy group, for example a chloro, bromo, methanesulfonyloxy, 4-nitrobenzenesulfonyloxy or toluene-4-sulfonyloxy group, particularly a methanesulfonyloxy, 4-nitrobenzenesulfonyloxy or toluene-4-sulfonyloxy group. More particularly $Lg^1$ is a methanesulfonyloxy group. Suitably $R^4$ is methyl. Suitably $R^2$ is methyl or hydrogen, particularly $R^2$ is methyl. In a further embodiment $R^2$ and $R^4$ are both methyl.

Particular stereoisomers of the compounds of the formulae IV', VIa, and VI include:

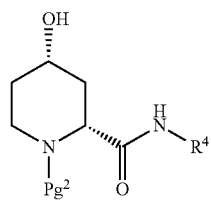
IV''

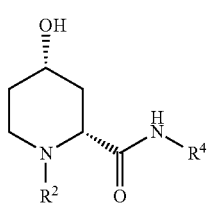
VIa'

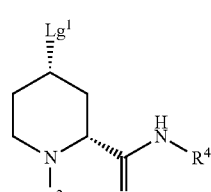
VI'

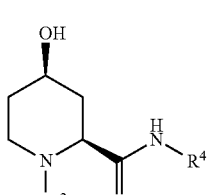
IV'''

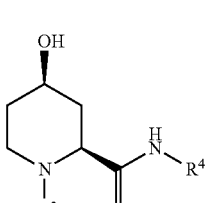
VIa''

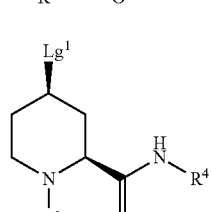
VI'' wherein $R^2$, $R^4$, $Pg^2$ and $Lg^1$ are as hereinbefore defined in relation to the compounds above of the formulae IV', VIa, and VI.

Biological Assays

The following assays may be used to measure the effects of the compounds of the present invention as inhibitors of the erbB tyrosine kinases, as inhibitors in-vitro of the proliferation of KB cells (human tumour cell line) and as inhibitors in vivo on the growth in nude mice of xenografts of LoVo tumour cells (colorectal adenocarcinoma).

a) Protein Tyrosine Kinase phosphorylation Assays

This test measures the ability of a test compound to inhibit the phosphorylation of a tyrosine containing polypeptide substrate by an erbB tyrosine kinase enzyme.

Recombinant intracellular fragments of EGFR, and erbB2 (accession numbers X00588 and X03363 respectively) were cloned and expressed in the baculovirus/Sf21 system. ErbB4, active (recombinant protein expressed in Sf21 insect cells) was commercially available from Upstate Catalogue number 14-569, Lot number PP023 reference JT09030402Dnd. Lysates were prepared from these cells by treatment with ice-cold lysis buffer (20 mM N-2-hydroxyethylpiperizine-N'-2-ethanesulfonic acid (HEPES) pH7.5, 150 mM NaCl, 10% glycerol, 1% Triton X-100, 1.5 mM $MgCl_2$, 1 mM ethylene glycol-bis($\beta$-aminoethyl ether) N',N',N',N'-tetraacetic acid (EGTA), plus protease inhibitors and then cleared by centrifugation.

Constitutive kinase activity of the recombinant protein was determined by its ability to phosphorylate a synthetic peptide (made up of a random co-polymer of Glutamic Acid, Alanine and Tyrosine in the ratio of 6:3:1). Specifically, Maxisorb™ 96-well immunoplates were coated with synthetic peptide (0.2 μg of peptide in a 100 μl phosphate buffered saline (PBS) solution and incubated at 4° C. overnight). Plates were washed in PBS-T (phosphate buffered saline with 0.05% Polysorbate 20) then in 50 mM HEPES pH 7.4 at room temperature to remove any excess unbound synthetic peptide. EGFR, ErbB2 or ErbB4 tyrosine kinase activity was assessed by incubation in peptide coated plates for 20 minutes at 22° C. in 100 mM HEPES pH 7.4, adenosine trisphosphate (ATP) at Km concentration for the respective enzyme, 2.5 mM $MnCl_2$, 0.05 mM $Na_3VO_4$, 0.1 mM DL-dithiothreitol (DTT), 0.1% Triton X-100 with test compound in DMSO (final concentration of 2.5%). Reactions were terminated by the removal of the liquid components of the assay followed by washing of the plates with PBS-T.

The immobilised phospho-peptide product of the reaction was detected by immunological methods. Firstly, plates were incubated for 90 minutes at room temperature with anti-phosphotyrosine primary antibodies that were raised in the mouse (4G10 from Upstate Biotechnology). Following extensive washing, plates were treated with Horseradish Peroxidase (HRP) conjugated sheep anti-mouse secondary antibody (NXA931 from Amersham) for 60 minutes at room temperature. After further washing, HRP activity in each well of the plate was measured colorimetrically using 22'-Azino-di-[3-ethylbenzthiazoline sulfonate (6)] diammonium salt crystals (ABTS™ from Roche) as a substrate.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b) EGFR Driven KB Cell Proliferation Assay

This assay measures the ability of a test compound to inhibit the proliferation of KB cells (human tumour cell line ATCC CCL-17).

KB cells were cultured in Dulbecco's modified Eagle's medium (DMEM) containing 10% foetal calf serum, 2 mM glutamine and 1% non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $1.25 \times 10^3$ cells per well of a 96 well plate in DMEM containing 2.5% charcoal stripped serum, 1 mM glutamine and 1% non-essential amino acids at 37° C. in 7.5% $CO_2$ and allowed to settle for 4 hours.

Following adhesion to the plate, the cells are treated with or without EGF (final concentration of 1 ng/ml) and with or without compound at a range of concentrations in dimethyl-sulfoxide (DMSO) (0.1% final) before incubation for 4 days. Following the incubation period, cell numbers were determined by addition of 50 μl of 3-(4,5-Dimethylthiazol-2-yl)-2,5-diphenyltetrazolium bromide (MTT) (stock 5 mg/ml) for 2 hours. MTT solution was then tipped off, the plate gently tapped dry and the cells dissolved upon the addition of 100 μl of DMSO.

Absorbance of the solubilised cells was read at 540 nm using a Molecular Devices ThermoMax microplate reader. Inhibition of proliferation was expressed as an $IC_{50}$ value. This was determined by calculation of the concentration of compound that was required to give 50% inhibition of EGF driven proliferation. The range of proliferation was calculated from the positive (vehicle plus EGF) and negative (vehicle minus EGF) control values. The $IC_{50}$ value obtained from basal cell growth gives a measure of selectivity.

c) Clone 24 Phospho-erbB2 Cell Assay

This immunofluorescence end point assay measures the ability of a test compound to inhibit the phosphorylation of erbB2 in a MCF7 (breast carcinoma) derived cell line which was generated by transfecting MCF7 cells with the full length erbB2 gene using standard methods to give a cell line that overexpresses full length wild type erbB2 protein (hereinafter 'Clone 24' cells).

Clone 24 cells were cultured in Growth Medium (phenol red free Dulbecco's modified Eagle's medium (DMEM) containing 10% foetal bovine serum, 2 mM glutamine and 1.2 mg/ml G418) in a 7.5% $CO_2$ air incubator at 37° C. Cells were harvested from T75 stock flasks by washing once in PBS (phosphate buffered saline, pH7.4, Gibco No. 10010-015) and harvested using 2 mls of Trypsin (1.25 mg/ml)/ethylaminediaminetetraacetic acid (EDTA) (0.8 mg/ml) solution. The cells were resuspended in Growth Medium. Cell density was measured using a haemocytometer and viability was calculated using Trypan Blue solution before being further diluted in Growth Medium and seeded at a density of $1 \times 10^5$ cells per well (in 100 μl) into clear bottomed 96 well plates (Packard, No. 6005182).

3 days later, Growth Medium was removed from the wells and replaced with 100 ul Assay Medium (phenol red free DMEM, 2 mM glutamine) either with or without erbB inhibitor compound. Plates were returned to the incubator for 4 hrs and then 20 μl of 20% fomaldehdye solution in PBS was added to each well and the plate was left at room temperature for 20 minutes. This fixative solution was removed with a multichannel pipette, 100 μl of PBS was added to each well and then removed with a multichannel pipette and then 50 μl PBS was added to each well. Plates were then sealed and stored for up to 2 weeks at 4° C.

Immunostaining was performed at room temperature. Wells were washed once with 200 μl PBS/Tween 20 (made by adding 1 sachet of PBS/Tween dry powder (Sigma, No. P3563) to 1 L of double distilled $H_2O$) using a plate washer. Then permeablised with 100 μl 0.5% Triton X-100 in PBS for 10 minutes, the plate was washed once with 200 μl PBS/Tween 20 then 100 μl Blocking Solution (5% Marvel dried skimmed milk (Nestle) in PBS/Tween 20) was added and incubated for 15 minutes. Blocking Solution was removed using a plate washer Following removal of the Blocking Solution, 30 µl of rabbit polyclonal anti-phospho ErbB2 IgG antibody (epitope phospho-Tyr 1248, Santa Cruz, No. SC-12352-R), diluted 1:250 in Blocking Solution, was added to each well and incubated for 2 hours. Then this primary antibody solution was removed from the wells using a plate washer followed by two 200 µl PBS/Tween 20 washes using a plate washer. Then 30 µl of Alexa-Fluor 488 goat anti-rabbit IgG secondary antibody (Molecular Probes, No. A-11008), diluted 1:750 in Blocking Solution, was added to each well. From now onwards, wherever possible, plates were protected from light exposure, at this stage by sealing with black backing tape. The plates were incubated for 45 minutes and then the secondary antibody solution was removed from the wells followed by three 200 µl PBS/Tween 20 washes using a plate washer. Then 50 µl of PBS was added to each well and plates were resealed with black backing tape and read immediately on the Acumen.

The Fluorescence signal is each well was measured using an Acumen Explorer Instrument (Acumen Bioscience Ltd.), a plate reader that can be used to rapidly quantitate features of images generated by laser-scanning. The instrument was set to measure the number of fluorescent objects above a pre-set threshold value and this provided a measure of the phosphorylation status of erbB2 protein. Fluorescence dose response data obtained with each compound was exported into a suitable software package (such as Origin) to perform curve fitting analysis. Inhibition of erbB2 phosphorylation was expressed as an $IC_{50}$ value. This was determined by calculation of the concentration of compound that was required to give 50% inhibition of erbB2 phosphorylation signal.

d) In Vivo Xenograft Assay

This assay measures the ability of a test compound to inhibit the growth of a LoVo tumour (colorectal adenocarcinoma obtained from the ATCC) in Female Swiss athymic mice (Alderley Park, nu/nu genotype).

Female Swiss athymic (nu/nu genotype) mice were bred and maintained in Alderley Park in negative pressure Isolators (PFI Systems Ltd.). Mice were housed in a barrier facility with 12 hr light/dark cycles and provided with sterilised food and water ad libitum. All procedures were performed on mice of at least 8 weeks of age. LoVo tumour cell (colorectal adenocarcinoma obtained from the ATCC) xenografts were established in the hind flank of donor mice by sub cutaneous injections of $1\times10^7$ freshly cultured cells in 100 µl of serum free media per animal. On day 5 post-implant, mice were randomised into groups of 7 prior to the treatment with compound or vehicle control that was administered once daily at 0.1 ml/10 g is body weight. Tumour volume was assessed twice weekly by bilateral Vernier calliper measurement, using the formula (length×width)×$\sqrt{(length\times width)}\times(\pi/6)$, where length was the longest diameter across the tumour, and width was the corresponding perpendicular. Growth inhibition from start of study dosing was calculated by comparison of the mean changes in tumour volume for the control and treated groups, and statistical significance between the two groups was evaluated using a one sided Students t test.

e) In Vivo Inhibition of Ovulation Assay

EGF and its receptor EGFR play a critical role in follicular maturation and ovulation (Park, J-Y. et al., Science, 303: 682-684, 2004). EGF/EGFR is believed to regulate growth of the granulosa cells, which line the follicle, surrounding the ova and which are responsible for production of follicular fluid. As the follicle develops, the production of follicular fluid increases, building pressure within the follicle. At the same time, an EGF/EGFR regulated tissue remodelling of the outer layer of follicular theca cells occurs. Build up of fluid pressure within the follicle combined with remodelling of the outer case of the follicle ultimately results in rupture of the follicle and release of the ova.

The ability of EGF receptor inhibitors to perturb ovulation was examined in rats. EGF-mediated maturation of follicle-enclosed oocytes has been documented previously in rat (Dekel, N. and Sherizly, I., Endocrinology, 116: 406-409, 1985). Female Alderley Park (AP) Wistar rats at pro-oestrus (cycle Day 4) were assigned to groups of 4 rats per treatment. At 4 pm on cycle day 4, rats were given a single oral dose of EGF receptor inhibitor or vehicle. The number of ova present in the fallopian tubes, in vehicle and EGF receptor inhibitor treated rats, was counted at post mortem the following morning. For each group, the total number of ova counted was divided by the number of animals examined, to generate a mean (ova per rat) value. Mean data from each EGF receptor inhibitor treated group was compared with the mean of the control (vehicle-treated) group, to determine the percentage inhibition of ovulation.

f) hERG-Encoded Potassium Channel Inhibition Assay

This assay determines the ability of a test compound to inhibit the tail current flowing through the human ether-a-go-go-related-gene (hERG)-encoded potassium channel.

Human embryonic kidney (HEK) cells expressing the hERG-encoded channel were grown in Minimum Essential Medium Eagle (EMEM; Sigma-Aldrich catalogue number M2279), supplemented with 10% Foetal Calf Serum (Labtech International; product number 4-101-500), 10% M1 serum-free supplement (Egg Technologies; product number 70916) and 0.4 mg/ml Geneticin G418 (Sigma-Aldrich; catalogue number G7034). One or two days before each experiment, the cells were detached from the tissue culture flasks with Accutase (TCS Biologicals) using standard tissue culture methods. They were then put onto glass coverslips resting in wells of a 12 well plate and covered with 2 ml of the growing media.

For each cell recorded, a glass coverslip containing the cells was placed at the bottom of a Perspex chamber containing bath solution (see below) at room temperature (~20° C.). This chamber was fixed to the stage of an inverted, phase-contrast microscope. Immediately after placing the coverslip in the chamber, bath solution was perfused into the chamber from a gravity-fed reservoir for 2 minutes at a rate of ~2 ml/min. After this time, perfusion was stopped.

A patch pipette made from borosilicate glass tubing (GC120F, Harvard Apparatus) using a P-97 micropipette puller (Sutter Instrument Co.) was filled with pipette solution (see hereinafter). The pipette was connected to the headstage of the patch clamp amplifier (Axopatch 200B, Axon Instruments) via a silver/silver chloride wire. The headstage ground was connected to the earth electrode. This consisted of a silver/silver chloride wire embedded in 3% agar made up with 0.85% sodium chloride.

The cell was recorded in the whole cell configuration of the patch clamp technique. Following "break-in", which was done at a holding potential of −80 mV (set by the amplifier), and appropriate adjustment of series resistance and capacitance controls, electrophysiology software (Clampex, Axon Instruments) was used to set a holding potential (−80 mV) and to deliver a voltage protocol. This protocol was applied every 15 seconds and consisted of a 1 s step to +40 mV followed by a 1 s step to −50 mV. The current response to each imposed voltage protocol was low pass filtered by the amplifier at 1 kHz. The filtered signal was then acquired, on line, by digitising this analogue signal from the amplifier with an analogue to digital converter. The digitised signal was then captured on a computer running Clampex software (Axon Instruments). During the holding potential and the step to +40 mV the current was sampled at 1 kHz. The sampling rate was then set to 5 kHz for the remainder of the voltage protocol.

The compositions, pH and osmolarity of the bath and pipette solution are tabulated below.

| Salt | Pipette (mM) | Bath (mM) |
|---|---|---|
| NaCl | — | 137 |
| KCl | 130 | 4 |
| $MgCl_2$ | 1 | 1 |
| $CaCl_2$ | — | 1.8 |
| HEPES | 10 | 10 |
| glucose | — | 10 |
| $Na_2ATP$ | 5 | — |
| EGTA | 5 | — |

| Parameter | Pipette | Bath |
|---|---|---|
| pH | 7.18-7.22 | 7.40 |
| pH adjustment with | 1M KOH | 1M NaOH |
| Osmolarity (mOsm) | 275-285 | 285-295 |

The amplitude of the hERG-encoded potassium channel tail current following the step from +40 mV to −50 mV was recorded on-line by Clampex software (Axon Instruments). Following stabilisation of the tail current amplitude, bath solution containing the vehicle for the test substance was applied to the cell. Providing the vehicle application had no significant effect on tail current amplitude, a cumulative concentration effect curve to the compound was then constructed.

The effect of each concentration of test compound was quantified by expressing the tail current amplitude in the presence of a given concentration of test compound as a percentage of that in the presence of vehicle.

Test compound potency ($IC_{50}$) was determined by fitting the percentage inhibition values making up the concentration-effect to a four parameter Hill equation using a standard data-fitting package. If the level of inhibition seen at the highest test concentration did not exceed 50%, no potency value was produced and a percentage inhibition value at that concentration was quoted.

g) Prophetic Assay for Inhibition of Mucus Production

Inhibition of mucus production by a quinazoline derivative according to the present invention could be studied in an assay using NCI-H292 cells, a human mucoepidermoid pulmonary carcinoma cell-line, stimulated with TGF-α. Cells would be cultured to confluence and stimulated with various concentrations of TGF-α or vehicle control. TGF-α will stimulate the epithelial cells to proliferate and differentiate into mucin producing cells. Mucins, for example MUC5AC and MUC2 form a major component of mucous secretions, and are upregulated in several mucus hypersecretory disease states, for example COPD. The mucous inhibitory properties of a quinazoline derivative according to the invention would be measured by adding a quinazoline derivative according to the invention at increasing concentrations to the NCI-H292 cell cultures at the time of stimulation with TGF-α. At 48 hours after stimulation, cells would be harvested and stained for intracellular MUC5AC content and analysed by flowcytometry. The degree of inhibition of MUC5AC by the quinazoline derivative under test would be measured as for example an EC50 value. Inhibition of MUC5AC mucin production is thought to translate into decreased mucous secretion.

Although the pharmacological properties of the compounds of the formula I vary with structural change as expected, in general activity possessed by compounds of the formula I, may be demonstrated at the following concentrations or doses in one or more of the above tests (a), (b), (c), (d) and (e):—

Test (a):—$IC_{50}$ (EGFR) in the range, for example, 0.001-0.1 μM;

Test (b):—$IC_{50}$ in the range, for example, 0.001-0.1 μM;

Test (c):—$IC_{50}$ in the range, for example, 0.1-10 μM;

Tests (d) and (e):—activity in the range, for example, 1-200 mg/kg/day;

By way of example, using Test (b) (EGFR driven KB cell proliferation assay), the compounds described in Examples 1 to 3 herein gave the $IC_{50}$ results shown below in Table A:

TABLE A

| Compound of Example | $IC_{50}$ (nM) Test (b) (EGFR driven KB cell proliferation assay) |
|---|---|
| 1 | 56 nM (n = 6) |
| 2 | 61 nM (n = 7) |
| 3 | 23 nM (n = 10) |

In Table A, n represents the number of tests carried out on each compound and the $IC_{50}$ values shown represent the geometric mean of the measured $IC_{50}$ values for each compound.

According to a further aspect of the invention there is provided a pharmaceutical composition which comprises a quinazoline derivative of the formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a quinazoline derivative of the formula I will naturally vary according to the nature and severity of the conditions, the age and sex of the animal or patient and the route of administration, according to well known principles of medicine.

In using a quinazoline derivative of the formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

We have found that the compounds of the present invention possess anti-proliferative properties such as anti-cancer properties that are believed to arise from their erbB family receptor tyrosine kinase inhibitory activity, particularly inhibition of the EGF receptor (erbB1) tyrosine kinase. Furthermore, the compounds according to the present invention possess substantially better potency against the EGF receptor tyrosine kinase, than against other tyrosine kinase enzymes, for example erbB2. Such compounds possess sufficient potency against the EGF receptor tyrosine kinase that they may be used in an amount sufficient to inhibit EGF receptor tyrosine kinase whilst demonstrating little, or significantly lower, activity against other tyrosine kinase enzymes such as erbB2. Such compounds are likely to be useful for the selective inhibition of EGF receptor tyrosine kinase and are likely to be useful for the effective treatment of, for example EGF driven tumours.

Accordingly, the compounds of the present invention are expected to be useful in the treatment of diseases or medical conditions mediated alone or in part by erbB receptor tyrosine kinases (especially EGF receptor tyrosine kinase), i.e. the compounds may be used to produce an erbB receptor tyrosine kinase inhibitory effect in a warm-blooded animal in need of such treatment. Thus the compounds of the present invention provide a method for the treatment of malignant cells characterised by inhibition of one or more of the erbB family of receptor tyrosine kinases. Particularly the compounds of the invention may be used to produce an anti-proliferative and/or pro-apoptotic and/or anti-invasive effect mediated alone or in part by the inhibition of erbB receptor tyrosine kinases. Particularly, the compounds of the present invention are expected to be useful in the prevention or treatment of those tumours that are sensitive to inhibition of one or more of the erbB receptor tyrosine kinases, such as EGF and/or erbB2 and/or erbB4 receptor tyrosine kinases (especially EGF receptor tyrosine kinase) that are involved in the signal transduction steps which drive proliferation and survival of these tumour cells. Accordingly the compounds of the present invention are expected to be useful in the treatment of hyperproliferative disorders, including psoriasis, benign prostatic hyperplasia (BPH), atherosclerosis and restenosis and/or cancer by providing an anti-proliferative effect, particularly in the treatment of erbB receptor tyrosine kinase sensitive cancers. Such benign or malignant tumours may affect any tissue and include non-solid tumours such as leukaemia, multiple myeloma or lymphoma, and also solid tumours, for example bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancers.

In addition the compounds of the invention may be useful in the treatment of other diseases and conditions of the respiratory tract including, for example: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus. Particularly the compounds of the invention may be useful in the treatment of Chronic Obstructive Pulmonary Disease (COPD).

According to this aspect of the invention there is provided a quinazoline derivative of the formula I, or a pharmaceutically acceptable salt thereof, for use as a medicament.

According to a further aspect of the invention there is provided a compound of the formula I, or a pharmaceutically acceptable salt thereof, for use in the production of an anti-proliferative effect in a warm-blooded animal such as man.

Thus according to this aspect of the invention there is provided the use of a quinazoline derivative of the formula I, or a pharmaceutically-acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline derivative of the formula I, or a pharmaceutically acceptable salt thereof, as hereinbefore defined.

According to a further aspect of the invention there is provided the use of a quinazoline derivative of the formula I, or a pharmaceutically-acceptable salt thereof, as defined hereinbefore in the manufacture of a medicament for use in the prevention or treatment of those tumours which are sensitive to inhibition of erbB receptor tyrosine kinases, such as EGFR and/or erbB2 and/or erbB4 (especially EGFR), that are involved in the signal transduction steps which lead to the proliferation of tumour cells.

According to a further feature of this aspect of the invention there is provided a method for the prevention or treatment of those tumours which are sensitive to inhibition of one or more of the erbB family of receptor tyrosine kinases, such as EGFR and/or erbB2 and/or erbB4 (especially EGFR), that are involved in the signal transduction steps which lead to the proliferation and/or survival of tumour cells, in a warm-blooded animal, such as man, in need of such treatment which comprises administering to said animal an effective amount of a quinazoline derivative of the formula I, or a pharmaceutically acceptable, salt thereof, as defined hereinbefore.

According to a further feature of this aspect of the invention there is provided a compound of the formula I, or a pharmaceutically acceptable salt thereof, for use in the prevention or treatment of those tumours which are sensitive to inhibition of erbB receptor tyrosine kinases, such as EGFR and/or erbB2 and/or erbB4 (especially EGFR), that are involved in the signal transduction steps which lead to the proliferation of tumour cells.

According to a further aspect of the invention there is provided the use of a quinazoline derivative of the formula I, or a pharmaceutically-acceptable salt thereof, as defined hereinbefore in the manufacture of a medicament for use in providing a EGFR and/or erbB2 and/or erbB4 (especially a EGFR) tyrosine kinase inhibitory effect.

According to a further feature of this aspect of the invention there is provided a method for providing a EGFR and/or an erbB2 and or an erbB4 (especially a EGFR) tyrosine kinase inhibitory effect in a warm-blooded animal, such as man, in need thereof, which comprises administering to said animal an effective amount of a quinazoline derivative of the formula I, or a pharmaceutically-acceptable salt thereof, as defined hereinbefore.

According to a further feature of this aspect of the invention there is provided a compound of the formula I, or a pharmaceutically acceptable salt thereof, for use in providing a EGFR and/or erbB2 and/or erbB4 (especially a EGFR) tyrosine kinase inhibitory effect.

According to a further feature of the present invention there is provided the use of a quinazoline derivative of the formula I, or a pharmaceutically-acceptable salt thereof, as defined hereinbefore in the manufacture of a medicament for use in providing a selective EGFR tyrosine kinase inhibitory effect.

According to a further feature of this aspect of the invention there is provided a method for providing a selective EGFR tyrosine kinase inhibitory effect in a warm-blooded animal, such as man, in need thereof which comprises administering to said animal an effective amount of a quinazoline derivative of the formula I, or a pharmaceutically-acceptable salt thereof, as defined hereinbefore.

According to a further feature of this aspect of the invention there is provided a compound of the formula I, or a pharmaceutically acceptable salt thereof, for use in providing a selective EGFR tyrosine kinase inhibitory effect.

By "a selective EGFR kinase inhibitory effect" is meant that the quinazoline derivative of formula I is more potent against EGF receptor tyrosine kinase than it is against other kinases. In particular some of the compounds according to the invention are more potent against EGF receptor kinase than against other tyrosine kinases such as other erbB receptor tyrosine kinases, particularly erbB2. For example a selective EGFR kinase inhibitor according to the invention is at least 5 times, preferably at least 10 times more potent against EGF receptor tyrosine kinase than it is against erbB2 tyrosine kinase, as determined from the relative $IC_{50}$ values in suitable assays (for example the by comparing the $IC_{50}$ value from the KB cell assay with the $IC_{50}$ value from the Clone 24 phospho-erbB2 cell assay for a given test compound as described above).

According to a further aspect of the present invention there is provided the use of a quinazoline derivative of the formula I, or a pharmaceutically acceptable salt thereof, as defined hereinbefore in the manufacture of a medicament for use in the treatment of a hyperproliferative disorder, for example a cancer (such as a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

According to a further feature of this aspect of the invention there is provided a method for treating a hyperproliferative disorder, for example a cancer (such as a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer) in a warm-blooded animal, such as man, in need of such treatment, which comprises administering to said animal an effective amount of a quinazoline derivative of the formula I, or a pharmaceutically-acceptable salt thereof, as defined hereinbefore.

According to a further aspect of the invention there is provided a quinazoline derivative of the formula I, or a pharmaceutically acceptable salt thereof, for use in the treatment of a hyperproliferative disorder, for example a cancer (such as a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

According to a further aspect of the invention there is provided the use of a quinazoline derivative of the formula I, or a pharmaceutically-acceptable salt thereof, as defined hereinbefore in the manufacture of a medicament for use in the treatment of a respiratory disease or condition as hereinbefore described, for example COPD.

According to a further feature of this aspect of the invention there is provided a method for treating a respiratory disease or condition as hereinbefore described, for example COPD, in a warm-blooded animal, such as man, in need of such treatment, which comprises administering to said animal an effective amount of a quinazoline derivative of the formula I, or a pharmaceutically-acceptable salt thereof, as defined hereinbefore.

According to a further aspect of the invention there is a quinazoline derivative of the formula I, or a pharmaceutically acceptable salt thereof, for use in the treatment of a respiratory disease or condition as hereinbefore described, for example COPD.

As mentioned above the size of the dose required for the therapeutic or prophlyactic treatment of a particular disease will necessarily be varied depending upon, amongst other things, the host treated, the route of administration and the severity of the illness being treated.

Combination Therapies for Use in the Treatment of Hyperproliferative Conditions

The anti-proliferative treatment defined hereinbefore may be applied as a sole therapy or may involve, in addition to a quinazoline derivative of the formula I as hereinbefore defined, or a pharmaceutically acceptable salt thereof, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like-adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antiestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example other inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent is Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ quinazoline derivatives of this invention within the dosage range described hereinbefore and the other pharmaceutically active agent within its approved dosage range.

According to this aspect of the invention there is provided a pharmaceutical product comprising a quinazoline derivative of the formula I as defined hereinbefore and an additional anti-tumour agent as defined hereinbefore for the conjoint treatment of cancer.

Combination Therapies for Use in the Treatment of Diseases or Conditions of the Respiratory Tract The invention further relates to combination therapies wherein a quinazoline derivative of the formula I as hereinbefore defined, or a pharmaceutically acceptable salt thereof, or a pharmaceutical composition or formulation comprising a quinazoline derivative of the formula I as hereinbefore defined, or a pharmaceutically acceptable salt thereof, is administered concurrently or sequentially or as a combined preparation with another therapeutic agent or agents, for the treatment of one or more of the diseases or conditions of the respiratory tract mentioned herein such as (but not restricted to), asthma, allergic rhinitis and chronic obstructive pulmonary disease (COPD), the compounds of the invention may be combined with agents listed below.

The present invention still further relates to the combination of a quinazoline derivative of the formula I as hereinbefore defined, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a quinazoline derivative of the formula I as hereinbefore defined, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a quinazoline derivative of the formula I as hereinbefore defined, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a quinazoline derivative of the formula I as hereinbefore defined, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention further relates to the combination of a quinazoline derivative of the formula I as hereinbefore defined, or a pharmaceutically acceptable salt thereof, and an anticholinergic agents including muscarinic receptor (M1, M2, and M3) antagonist such as atropine, hyoscine, glycopyrrolate, ipratropium bromide, tiotropium bromide, oxitropium bromide, pirenzepine or telenzepine.

The present invention still further relates to the combination of a quinazoline derivative of the formula I as hereinbefore defined, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a quinazoline derivative of the formula I as hereinbefore defined, or a pharmaceutically acceptable salt thereof, and a chromone, such as sodium cromoglycate or nedocromil sodium.

The present invention still further relates to the combination of a quinazoline derivative of the formula I as hereinbefore defined, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention still further relates to the combination of a quinazoline derivative of the formula I as hereinbefore defined, or a pharmaceutically acceptable salt thereof, together with:
(i) a serine/threonine kinase (such as an inhibitor of a MAP kinase such as p38, JNK, protein kinase A, B or C, or IKK); (ii) TNF-alpha converting enzyme inhibitor (TACE); (iii) induced nitric oxide synthase (iNOS) inhibitor; (iv) chemoattractant receptor-homologous molecule expressed on TH2 cells, (such as a CRTH2 antagonist); (iv) inhibitor of P38; or (v) agent modulating the activity of purinergic receptors such as P2X7.

Although the quinazoline derivatives of the formula I are primarily of value as therapeutic agents for use in warm-blooded animals (including man), they are also useful whenever it is required to inhibit the effects of the erbB (particularly EGF) receptor tyrosine protein kinases. Thus, they are useful as pharmacological standards for use in the development of new biological tests and in the search for new pharmacological agents.

The invention will now be illustrated by the following non-limiting examples in which, unless stated otherwise:
(i) temperatures are given in degrees Celsius (° C.); operations were carried out at room or ambient temperature, that is, at a temperature in the range of 18-25° C.;
(ii) organic solutions were dried over anhydrous magnesium sulfate; evaporation of solvent was carried out using a rotary evaporator under reduced pressure (600-4000 Pascals; 4.5-30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC and/or analytical LCMS, and reaction times are given for illustration only;
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; b, broad;
(viii) chemical symbols have their usual meanings; SI units and symbols are used;
(ix) solvent ratios are given in volume:volume (v/v) terms; and
(x) mass spectra (MS) were run with an electron energy of 70 electron volts in the chemical ionization (CI) mode using a direct exposure probe and ionization was effected by electrospray; values for m/z are given; generally, only ions which indicate the parent mass are reported; and unless otherwise stated, the mass ion quoted is (MH)$^+$;
(xi) where a synthesis is described as being analogous to that described in a previous example the amounts used are the millimolar ratio equivalents to those used in the previous example;
(xii) where a compound is described as being purified using Mass-Triggered Preparative LCMS (liquid chromatography-mass spectrometry analysis) under standard basic conditions, the following conditions were used:

Column: ThermoHypersil Keystone B-Basic 5µ 21 mm×100 mm;

Eluant: 7.5 minutes Gradient from 20% to 95% of acetonitrile in water (buffer 2 g/l of $(NH_4)_2CO_3$, pH 8.9);

Flow rate: 25 ml/min;

and (xiii) the following abbreviations have been used:

AcOH Acetic Acid

DCM Dichloromethane

DEAD Diethylazodicarboxylate

DIPEA Diisopropylethylamine

DMA N,N-dimethylacetamide

DMF N,N-dimethylformamide

DTAD Di-tert-butyl azodicarboxylate

EtOAc Ethyl acetate $Et_3N$ Triethylamine

HATU O-(7-azabenzotriazol-1-yl)-N,N,N',N'-tetramethyluronium hexafluoro-phosphate IBCF Isobutylchloroformate MeOH Methanol $MeNH_2$ Methylamine NMM N-Methyl morpholine NMP N-methylpyrrolidin-2-one SCX Strong cation exchange column TFA Trifluoroacetic acid THF Tetrahydrofuran TLC Thin-layer chromatography RP-HPLC Reverse phase high performance liquid chromatography

Figure 1:
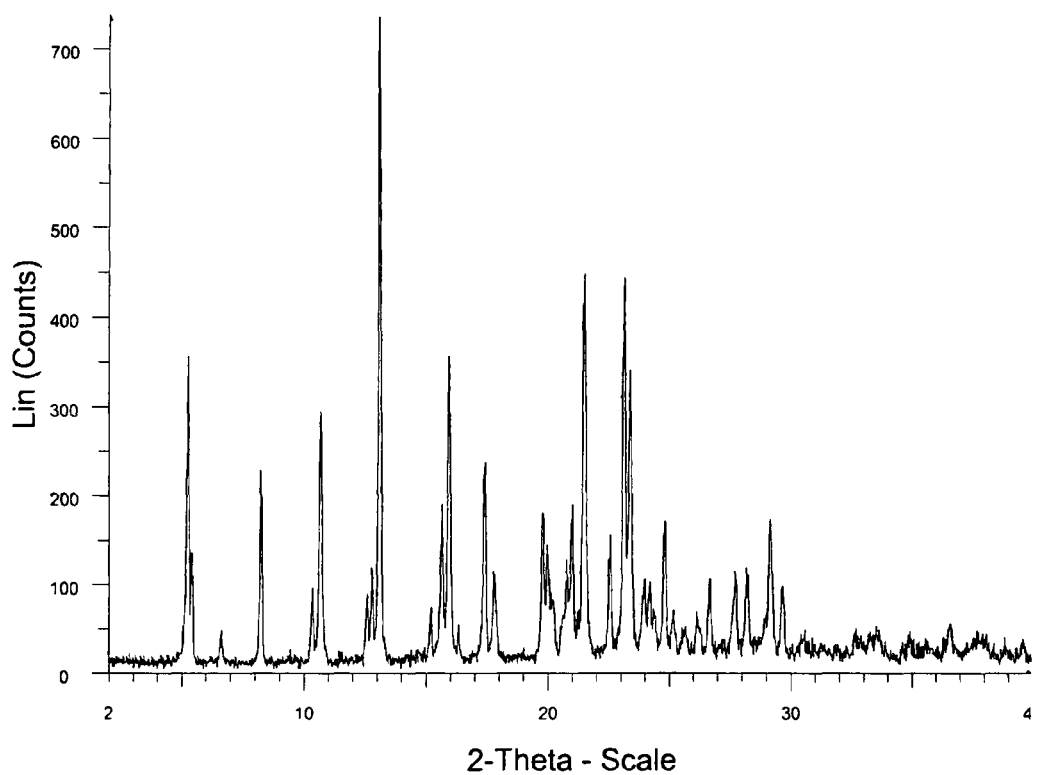
FIG. 1: The X-ray powder diffraction pattern of (2R,4R)-4-({4-[(3-chloro-2-fluorophenyl)amino]-7-methoxyquinazolin-6-yl}oxy)-N,1-dimethylpiperidine-2-carboxamide dimaleate salt described in Example 6 with the 2θ values plotted on the x-axis and the relative line intensity (counts) plotted on the y-axis.

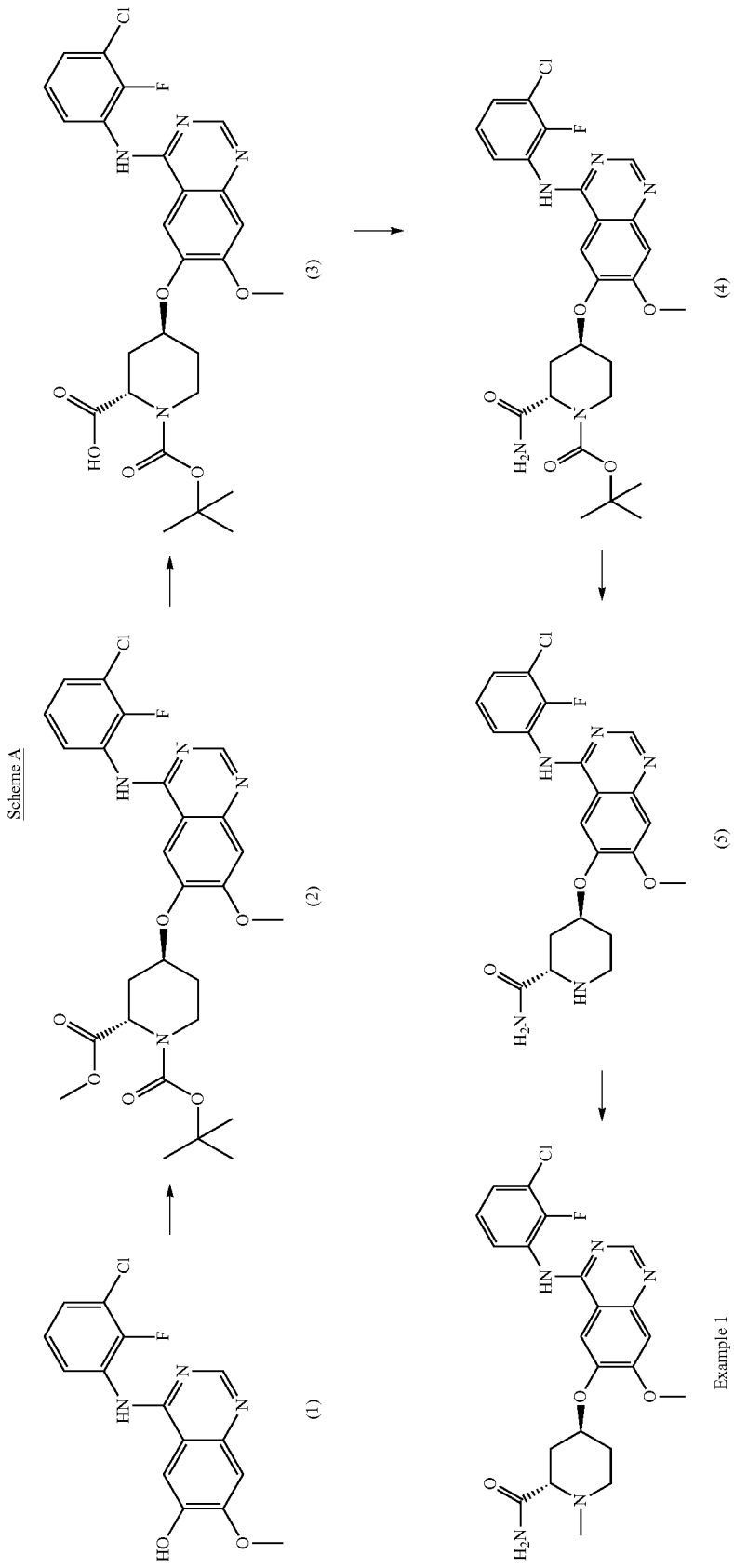
Scheme A

Molecular sieves (5 g) followed by aqueous formaldehyde (10 ml) were added to a stirred solution of (2S,4S)-4-({4-[(3-chloro-2-fluorophenyl)amino]-7-methoxyquinazolin-6-yl}oxy)piperidine-2-carboxamide (5) (3.1 g, 6.97 mmol) in DCM-AcOH (100:10 ml) at room temperature. The reaction mixture was stirred for 1-2 minutes before solid sodium triacetoxyborohydride (2.93 g, 13.9 mmol) was added portionwise over 5 minutes. The reaction was essentially complete after all the sodium triacetoxyborohydride reducing agent had been added. DCM was added (100 ml) and the reaction was carefully neutralised with saturated aqueous $NaHCO_3$ (aq). The organic extract was washed with brine, dried ($MgSO_4$) and concentrated to a yellow foam. The residue was purified by flash chromatography (silica gel, DCM-$NH_3$/MeOH 2%) to give the title product as a white solid (1.8 g, 56%): $^1$H NMR Spectrum: (DMSO $d_6$) 1.86-1.91 (m, 3H), 2.07-2.09 (m, 1H), 2.20 (s, 3H), 2.47-2.49 (m, 1H), 2.71-2.81 (m, 2H), 3.96 (s, 3H), 4.82 (m, 1H), 7.02 (s, 1H), 7.23 (s, 1H), 7.26-7.29 (m, 2H), 7.47-7.53 (m, 2H), 7.82 (s, 1H), 8.37 (s, 1H), 9.60 (s, 1H); Mass Spectrum: (M+H)$^+$ 460.1.

The starting material (2S,4S)-4-({4-[(3-chloro-2-fluorophenyl)amino]-7-methoxyquinazolin-6-yl}oxy)piperidine-2-carboxamide (5) was prepared as follows:

DTAD (13.3 g, 57.9 mmol) dissolved in 50 ml of DCM was added over a period of 10 minutes to a stirred suspension of 4-[(3-chloro-2-fluorophenyl)amino]-7-methoxyquinazolin-6-ol (1) (4.94 g, 15.5 mmol, prepared as described in WO 03/082831, Reference Example 2 therein), triphenylphosphine (18.3 g, 69.5 mmol) and (2S,4R)—N-(tert-butoxycarbonyl)-4-hydroxypiperidine-2-carboxylic acid methyl ester (ex ACROS, 6 g, 23.2 mmol) in DCM (150 ml) at −15° C. (acetone/ice). The reaction mixture was allowed to warm to room temperature and stirred for 2 hours, concentrated to approximately 50 ml and purified directly by flash chromatography (silica gel, eluting with a gradient from 100% DCM to DCM/EtOAc (80/20) to DCM/EtOAc (50/50) to give 1-tert-butyl 2-methyl (2S,4S)-4-({4-[(3-chloro-2-fluorophenyl)amino]-7-methoxyquinazolin-6-yl}oxy)piperidine-1,2-dicarboxylate (2) (6 g, 69%) as a white foam; $^1$H NMR Spectrum: (DMSO $d_6$) 1.47-1.53 (m, 11H), 1.86-1.91 (m, 1H), 2.25-2.36 (m, 1H), 2.95-3.13 (m, 1H), 3.70 (s, 3H), 3.95 (s, 3H), 3.98-4.04 (m, 1H), 4.45 (m, 1H), 4.86-4.94 (m, 1H), 7.31 (t, 1H), 7.51-7.64 (m, 3H), 7.80 (s, 1H), 8.39 (s, 1H), 9.54 (s, 1H); Mass Spectrum: (M+H)$^+$ 561.1.

A stirred solution of 1-tert-butyl 2-methyl (2S,4S)-4-({4-[(3-chloro-2-fluorophenyl)amino]-7-methoxyquinazolin-6-yl}oxy)piperidine-1,2-dicarboxylate (2) (6 g, 10.7 mmol) in THF (30 ml) and water (30 ml) was prepared at room temperature then cooled to 0° C. and solid LiOH.$H_2O$ (0.54 g, 12.9 mmol) was added. The reaction mixture was stirred at room temperature for 3 hours, acidified with acetic acid and extracted with DCM. The resulting residue was evaporated to dryness, azeotroped with toluene (3×50 ml) and dried to a constant weight to give (2S,4S)-1-(tert-butoxycarbonyl)-4-({4-[(3-chloro-2-fluorophenyl)amino]-7-methoxyquinazolin-6-yl}oxy)piperidine-2-carboxylic acid (3) (5.27 g, 90%), which was used without further purification; Mass Spectrum: (M+H)$^+$ 547.1.

A stirred solution of (2S,4S)-1-(tert-butoxycarbonyl)-4-({4-[(3-chloro-2-fluorophenyl)amino]-7-methoxyquinazolin-6-yl}oxy)piperidine-2-carboxylic acid (3) (5 g, 9.16 mmol) in THF (50 ml) was cooled to −15° C. (acetone/ice). NMM (1.5 ml, 13.7 mmol) was added to the solution followed by IBCF (1.54 ml, 11.9 mmol). The reaction mixture was held at −15° C. (the formation of the mixed anhydride was monitored by TLC (THF)). After 5-10 minutes, the reaction mixture was treated with concentrated aqueous ammonia (3 ml) at −15° C. and allowed to warm to room temperature. The reaction mixture was diluted with DCM (250 ml), washed with water (2×20 ml) and concentrated to give tert-butyl (2S,4S)-2-(aminocarbonyl)-4-({4-[(3-chloro-2-fluorophenyl)amino]-7-methoxyquinazolin-6-yl}oxy)piperidine-1-carboxylate (4) (5 g, 100%) as a pale yellow foam which was used without further purification; Mass Spectrum: (M+H)$^+$ 546.1.

TFA (15 ml) was added over a period of 5 minutes to a stirred solution of tert-butyl (2S,4S)-2-(aminocarbonyl)-4-({4-[(3-chloro-2-fluorophenyl)amino]-7-methoxyquinazolin-6-yl}oxy)piperidine-1-carboxylate (4) (5 g, 9.16 mmol) in DCM (15 ml) at 0° C. The reaction mixture was allowed to warm to room temperature and stirred for 1 hour after which time, the reaction was complete. The reaction mixture was concentrated to dryness, azeotroped twice with toluene and the residue was purified by flash chromatography (silica gel, DCM-$NH_3$/MeOH 5%) to give (2S,4S)-4-({4-[(3-chloro-2-fluorophenyl)amino]-7-methoxyquinazolin-6-yl}oxy)piperidine-2-carboxamide (5) (3.1 g, 76%) as a white solid: $^1$H NMR Spectrum: (DMSO $d_6$) 1.72-1.89 (m, 2H), 1.91 (m, 1H), 2.03 (m, 1H), 2.78 (m, 1H), 2.92 (m, 1H), 3.47 (m, 1H), 3.95 (s, 3H), 4.84 (m, 1H), 7.06 (s, 1H), 7.27 (s, 1H), 7.30 (m, 2H), 7.49-7.55 (m, 2H), 7.84 (s, 1H), 8.37 (s, 1H), 9.56 (s, 1H), Mass Spectrum: (M+H)$^+$ 446.1.

Example 2

(2S,4S)-4-({4-[(3-chloro-2-fluorophenyl)amino]-7-methoxyquinazolin-6-yl}oxy)-N,1-dimethylpiperidine-2-carboxamide

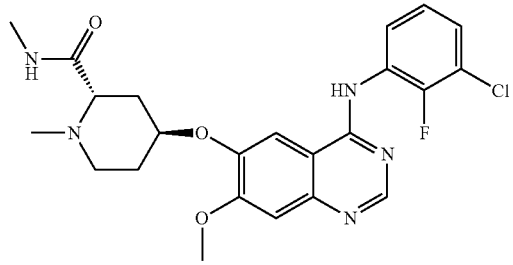 [SMILES: CNC(=O)[C@@H]1C[C@@H](Oc2cc3c(Nc4cccc(Cl)c4F)ncnc3cc2OC)CCN1C]

Molecular sieves (5 g) followed by aqueous formaldehyde (10 ml) were added to a stirred solution of (2S,4S)-4-({4-[(3-chloro-2-fluorophenyl)amino]-7-methoxyquinazolin-6-yl}oxy)-N-methylpiperidine-2-carboxamide (3.0 g, 6.52 mmol) in DCM-AcOH (100:10 ml) at room temperature. The reaction mixture was stirred for 1-2 minutes before solid sodium triacetoxyborohydride (2.77 g, 13.1 mmol) was added portionwise over 5 minutes. The reaction was essentially complete after all the sodium triacetoxyborohydride reducing agent had been added. DCM was added (100 ml) and the reaction was carefully neutralised with saturated aqueous $NaHCO_3$(aq). The organic extract was washed with brine, dried ($MgSO_4$) and concentrated to a yellow foam. The residue was purified by flash chromatography (silica gel, DCM-$NH_3$/MeOH 2%) to give the title product as a white solid (2 g, 65%): $^1$H NMR Spectrum: (DMSO $d_6$) 1.85-1.96 (m, 3H), 2.07 (m, 1H), 2.15 (s, 3H), 2.45-2.50 (m, 1H), 2.59 (d, 3H), 2.71 (m, 1H), 2.84 (m, 1H), 3.96 (s, 3H), 4.81 (m, 1H), 7.23 (s, 1H), 7.28 (t, 1H), 7.47-7.53 (m, 2H), 7.81 (s, 2H), 8.37 (s, 1H), 9.59 (s, 1H); Mass Spectrum: (M+H)$^+$ 474.1.

The starting material (2S,4S)-4-({-4-[(3-chloro-2-fluorophenyl)amino]-7-methoxyquinazolin-6-yl}oxy)-N-methylpiperidine-2-carboxamide was prepared as follows:

A stirred solution of (2S,4S)-1-(tert-butoxycarbonyl)-4-({-4-[(3-chloro-2-fluorophenyl)amino]-7-methoxyquinazolin-6-yl}oxy)piperidine-2-carboxylic acid (4 g, 7.31 mmol, prepared as described in Example 1) in THF (50 ml) was cooled to −15° C. (acetone/ice). NMM (1.21 ml, 11.0 mmol) was added to the solution followed by IBCF (1.24 ml, 9.51 mmol). The reaction mixture was held at −15° C. (the formation of the mixed anhydride was monitored by TLC (THF)). After 5-10 minutes, the reaction mixture was treated with a 2.0M solution of methylamine in THF (10 ml) at −15° C. and allowed to warm to room temperature. The reaction mixture was diluted with DCM (250 ml), washed with water (2×20 ml) and concentrated to give tert-butyl (2S,4S)-4-({4-[(3-chloro-2-fluorophenyl)amino]-7-methoxyquinazolin-6-yl}oxy)-2-[(methylamino)carbonyl]piperidine-1-carboxylate (4.1 g, 100%) as pale yellow foam which was used without further purification; Mass Spectrum: (M+H)⁺ 560.1.

TFA (15 ml) was added over a period of 5 minutes to a stirred solution of tert-butyl (2S,4S)-4-({4-[(3-chloro-2-fluorophenyl)amino]-7-methoxyquinazolin-6-yl}oxy)-2-[(methylamino)carbonyl]piperidine-1-carboxylate (4.1 g, 7.31 mmol) in DCM (15 ml) at 0° C. The reaction mixture was allowed to warm to room temperature and stirred for 1 hour after which time, the reaction was complete. The reaction mixture was concentrated to dryness, azeotroped twice with toluene to give (2S,4S)-4-({4-[(3-chloro-2-fluorophenyl)amino]-7-methoxyquinazolin-6-yl}oxy)-N-methylpiperidine-2-carboxamide (3.0 g, 89%) the crude residue was used without further purification; Mass Spectrum: (M+H)⁺ 460.1.

Example 3

(2R,4R)-4-({4-[(3-chloro-2-fluorophenyl)amino]-7-methoxyquinazolin-6-yl}oxy)-N,1-dimethylpiperidine-2-carboxamide

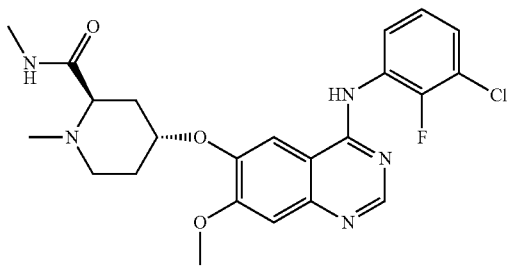 [SMILES: CNC(=O)[C@H]1C[C@H](Oc2cc3c(Nc4cccc(Cl)c4F)ncnc3cc2OC)CCN1C]

Molecular sieves (5 g) followed by aqueous formaldehyde (10 ml) were added to a stirred solution of (2R,4R)-4-({4-[(3-chloro-2-fluorophenyl)amino]-7-methoxyquinazolin-6-yl}oxy)-N-methylpiperidine-2-carboxamide (3.6 g, 7.84 mmol) in DCM-AcOH (100:10 ml) at room temperature. The reaction mixture was stirred for 1-2 minutes before solid sodium triacetoxyborohydride (3.31 g, 15.7 mmol) was added portionwise over 5 minutes. The reaction was essentially complete after all the sodium triacetoxyborohydride reducing agent had been added. DCM was added (100 ml) and the reaction was carefully neutralised with saturated aqueous NaHCO₃(aq). The organic extract was washed with brine, dried (MgSO₄) and concentrated to a yellow foam. The residue was purified by flash chromatography (silica gel, DCM-NH₃/MeOH 2%) to give the title product as a white solid (1.8 g, 49%): ¹H NMR Spectrum: (DMSO d₆) 1.85-1.96 (m, 3H), 2.07 (m, 1H), 2.15 (s, 3H), 2.45-2.50 (m, 1H), 2.59 (d, 3H), 2.71 (m, 1H), 2.84 (m, 1H), 3.96 (s, 3H), 4.81 (m, 1H), 7.23 (s, 1H), 7.28 (t, 1H), 7.47-7.53 (m, 2H), 7.81 (s, 2H), 8.37 (s, 1H), 9.59 (s, 1H); Mass Spectrum: (M+H)⁺ 474.1.

The starting material (2R,4R)-4-({4-[(3-chloro-2-fluorophenyl)amino]-7-methoxyquinazolin-6-yl}oxy)-N-methylpiperidine-2-carboxamide was prepared as follows:

DTAD (7.26 g, 31.5 mmol) dissolved in 50 ml of DCM was added over a period of 10 minutes to a stirred suspension of 4-[(3-chloro-2-fluorophenyl)amino]-7-methoxyquinazolin-6-ol (5.00 g, 15.7 mmol), triphenylphosphine (8.57 g, 62.6 mmol) and (2R,4S)—N-(tert-butoxycarbonyl)-4-hydroxypiperidine-2-carboxylic acid methyl ester (ex ACROS, 5.42 g, 20.9 mmol) in DCM (150 ml) at −15° C. (acetone/ice). The reaction mixture was allowed to warm to room temperature and stirred for 2 hours, concentrated to approximately 50 ml and purified directly by flash chromatography (silica gel, eluting with a gradient from 100% DCM to DCM/EtOAc (80/20) to DCM/EtOAc (50/50) to give 1-tert-butyl 2-methyl (2R,4R)-4-({4-[(3-chloro-2-fluorophenyl)amino]-7-methoxyquinazolin-6-yl}oxy)piperidine-1,2-dicarboxylate (5.5 g, 81%) as a white foam; ¹H NMR Spectrum: (DMSO d₆) 1.47-1.53 (m, 11H), 1.86-1.91 (m, 1H), 2.25-2.36 (m, 1H), 2.95-3.13 (m, 1H), 3.70 (s, 3H), 3.95 (s, 3H), 3.98-4.04 (m, 1H), 4.45 (m, 1H), 4.86-4.94 (m, 1H), 7.31 (t, 1H), 7.51-7.64 (m, 3H), 7.80 (s, 1H), 8.39 (s, 1H), 9.54 (s, 1H); Mass Spectrum: (M+H)⁺ 561.1.

A stirred solution of 1-tert-butyl 2-methyl (2R,4R)-4-({4-[(3-chloro-2-fluorophenyl)amino]-7-methoxyquinazolin-6-yl}oxy)piperidine-1,2-dicarboxylate (6.5 g, 11.6 mmol) in THF (35 ml) and water (35 ml) was prepared at room temperature then cooled to 0° C. and solid LiOH.H₂O (0.53 g, 12.7 mmol) was added. The reaction was allowed to stir at room temperature for 3 hours, acidified with acetic acid and extracted with DCM. The resulting residue was evaporated to dryness, azeotroped with toluene (3×50 ml) and dried to a constant weight to give (2R,4R)-1-(tert-butoxycarbonyl)-4-({4-[(3-chloro-2-fluorophenyl)amino]-7-methoxyquinazolin-6-yl}oxy)piperidine-2-carboxylic acid (5.35 g, 84%), which was used without further purification; Mass Spectrum: (M+H)⁺ 547.1.

A stirred solution of (2R,4R)-1-(tert-butoxycarbonyl)-4-({4-[(3-chloro-2-fluorophenyl)amino]-7-methoxyquinazolin-6-yl}oxy)piperidine-2-carboxylic acid (5.35 g, 9.80 mmol) in THF (50 ml) was cooled to −15° C. (acetone/ice). NMM (1.49 ml, 14.9 mmol) was added to the solution followed by IBCF (2.0 ml, 12.75 mmol). The reaction mixture was held at −15° C. (the formation of the mixed anhydride was monitored by TLC (THF)). After 5-10 minutes, the reaction mixture was treated with a 2.0M solution of methylamine in THF (10 ml) at −15° C. and allowed to warm to room temperature. The reaction mixture was diluted with DCM (250 ml), washed with water (2×20 ml) and concentrated to give tert-butyl (2R,4R)-4-({4-[(3-chloro-2-fluorophenyl)amino]-7-methoxyquinazolin-6-yl}oxy)-2-[(methylamino)carbonyl]piperidine-1-carboxylate (5.94 g, 100%) as a pale yellow foam which was used without further purification; Mass Spectrum: (M+H)⁺ 560.1.

TFA (25 ml) was added over a period of 5 minutes to a stirred solution of tert-butyl (2R,4R)-4-({4-[(3-chloro-2-fluorophenyl)amino]-7-methoxyquinazolin-6-yl}oxy)-2-[(methylamino)carbonyl]piperidine-1-carboxylate (5.94 g, 10.63 mmol) in DCM (25 ml) at 0° C., was added. The reaction mixture was allowed to warm to room temperature and stirred for 1 hour after which time, the reaction was complete. The reaction mixture was concentrated to dryness, azeotroped twice with toluene and the residue was purified by flash chromatography (silica gel, DCM-NH$_3$/MeOH 5%) to give (2R,4R)-4-({4-[(3-chloro-2-fluorophenyl)amino]-7-methoxyquinazolin-6-yl}oxy)-N-methylpiperidine-2-carboxamide (3.6 g, 74%) as a white solid: $^1$H NMR Spectrum: (DMSO d$_6$) 1.60-2.03 (m, 4H), 2.50-2.58 (m, 1H), 2.59 (d, 3H), 2.78 (m, 1H), 3.53 (m, 1H), 3.84 (s, 1H), 3.96 (s, 3H), 4.84 (m, 1H), 7.27 (s, 1H), 7.35 (t, 1H), 7.47-7.60 (m, 2H), 7.85 (m, 2H), 8.38 (s, 1H), 9.56 (s, 1H); Mass Spectrum: (M+H)$^+$ 460.1.

Example 4

(2R,4R)-4-({4-[(3-chloro-2-fluorophenyl)amino]-7-methoxyquinazolin-6-yl}oxy)-1-methylpiperidine-2-carboxamide

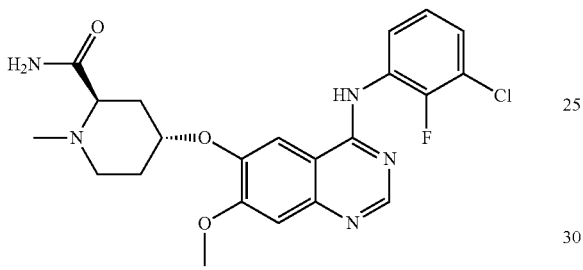

The title compound was prepared as shown in scheme B:

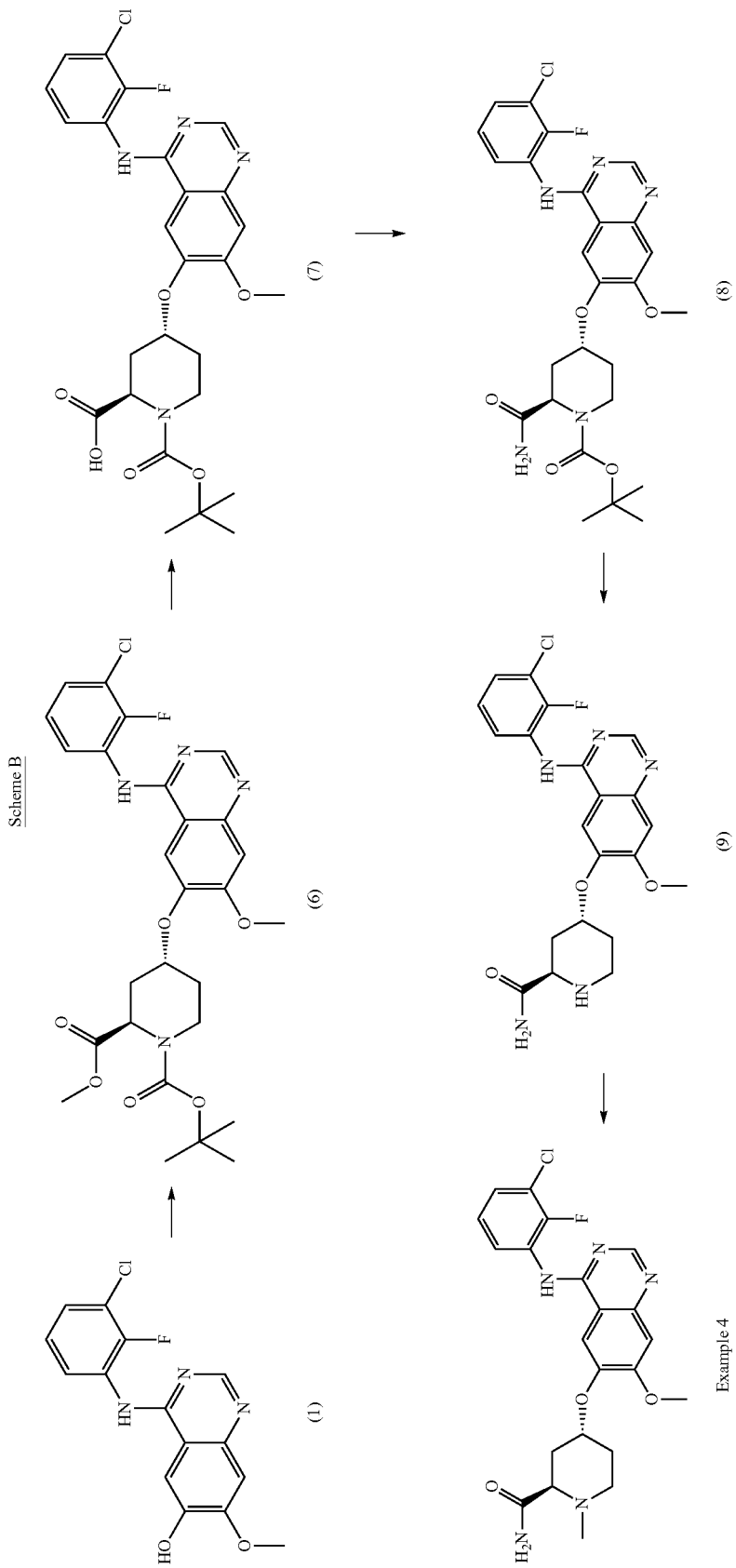

Molecular sieves (0.5 g) followed by aqueous formaldehyde (1 ml) were added to a stirred solution of (2R,4R)-4-({4-[(3-chloro-2-fluorophenyl)amino]-7-methoxyquinazolin-6-yl}oxy)piperidine-2-carboxamide (9) (0.102 g, 0.23 mmol) in DCM-AcOH (10:1 ml) at room temperature. The reaction mixture was stirred for 1-2 minutes before solid sodium triacetoxyborohydride (0.10 g, 0.463 mmol) was added portionwise over 5 minutes. The reaction was essentially complete after all the sodium triacetoxyborohydride reducing agent had been added. DCM was added (20 ml) and the reaction was carefully neutralised with saturated aqueous NaHCO$_3$(aq). The organic extract was washed with brine, dried (MgSO$_4$) and concentrated to a yellow foam. The residue was purified by preparative LCMS (standard basic conditions) to give the title product as a white solid (0.85 g, 80%): $^1$H NMR Spectrum: (DMSO d$_6$) 1.87-1.92 (m, 3H), 2.07-2.09 (m, 1H), 2.20 (s, 3H), 2.43-2.47 (m, 1H), 2.71-2.80 (m, 2H), 3.96 (s, 3H), 4.82 (m, 1H), 7.03 (s, 1H), 7.23 (s, 1H), 7.26-7.30 (m, 2H), 7.47-7.54 (m, 2H), 7.82 (s, 1H), 8.37 (s, 1H), 9.60 (s, 1H); Mass Spectrum: (M+H)$^+$ 459.9.

The starting material (2R,4R)-4-({4-[(3-chloro-2-fluorophenyl)amino]-7-methoxyquinazolin-6-yl}oxy)piperidine-2-carboxamide (9) was prepared as follows:

DTAD (7.26 g, 31.5 mmol) dissolved in 50 ml of DCM was added over a period of 10 minutes to a stirred suspension of 4-[(3-chloro-2-fluorophenyl)amino]-7-methoxyquinazolin-6-ol (5.00 g, 15.7 mmol), triphenylphosphine (8.57 g, 62.6 mmol) and (2R,4S)—N-(tert-butoxycarbonyl)-4-hydroxypiperidine-2-carboxylic acid methyl ester (ex ACROS, 5.42 g, 20.9 mmol) in DCM (150 ml) at −15° C. (acetone/ice). The reaction mixture was allowed to warm to room temperature and stirred for 2 hours, concentrated to approximately 50 ml and purified directly by flash chromatography (silica gel, eluting with a gradient from 100% DCM to DCM/EtOAc (80/20) to DCM/EtOAc (50/50) to give 1-tert-butyl 2-methyl (2R,4R)-4-({4-[(3-chloro-2-fluorophenyl)amino]-7-methoxyquinazolin-6-yl}oxy)piperidine-1,2-dicarboxylate (6) (5.5 g, 81%) as a white foam; $^1$H NMR Spectrum: (DMSO d$_6$) 1.47-1.53 (m, 11H), 1.86-1.91 (m, 1H), 2.25-2.36 (m, 1H), 2.95-3.13 (m, 1H), 3.70 (s, 3H), 3.95 (s, 3H), 3.98-4.04 (m, 1H), 4.45 (m, 1H), 4.86-4.94 (m, 1H), 7.31 (t, 1H), 7.51-7.64 (m, 3H), 7.80 (s, 1H), 8.39 (s, 1H), 9.54 (s, 1H); Mass Spectrum: (M+H)$^+$ 561.1.

A stirred solution of 1-tert-butyl 2-methyl (2R,4R)-4-({4-[(3-chloro-2-fluorophenyl)amino]-7-methoxyquinazolin-6-yl}oxy)piperidine-1,2-dicarboxylate (6) (6.5 g, 11.6 mmol) in THF (35 ml) and water (35 ml) was prepared at room temperature then cooled to 0° C. and solid LiOH.H$_2$O (0.53 g, 12.7 mmol) was added. The reaction was allowed to stir at room temperature for 3 hours, acidified with acetic acid and extracted with DCM. The resulting residue was evaporated to dryness, azeotroped with toluene (3×50 ml) and dried to a constant weight to give (2R,4R)-1-(tert-butoxycarbonyl)-4-({4-[(3-chloro-2-fluorophenyl)amino]-7-methoxyquinazolin-6-yl}oxy)piperidine-2-carboxylic acid (7) (5.35 g, 84%), which was used without further purification; Mass Spectrum: (M+H)$^+$ 547.1.

A stirred solution of (2R,4R)-1-(tert-butoxycarbonyl)-4-({4-[(3-chloro-2-fluorophenyl)amino]-7-methoxyquinazolin-6-yl}oxy)piperidine-2-carboxylic acid (7) (0.13 g, 0.232 mmol) in THF (5 ml) was cooled to −15° C. (acetone/ice). NMM (0.035 g, 0.348 mmol) was added to the solution followed by IBCF (0.041 g, 0.301 mmol). The reaction mixture was held at −15° C. (the formation of the mixed anhydride was monitored by TLC (THF)). After 5-10 minutes, the reaction mixture was treated with aqueous ammonia in THF (0.2 ml) at −15° C. and allowed to warm to room temperature. The reaction mixture was diluted with DCM (20 ml), washed with water (2×2 ml) and concentrated to give tert-butyl (2R,4R)-2-(aminocarbonyl)-4-({4-[(3-chloro-2-fluorophenyl)amino]-7-methoxyquinazolin-6-yl}oxy)piperidine-1-carboxylate (8) (0.13 g, 100%) as a pale yellow foam which was used without further purification; Mass Spectrum: (M+H)$^+$ 544.0.

TFA (2 ml) was added over a period of 5 minutes to a stirred solution of tert-butyl (2R,4R)-2-(aminocarbonyl)-4-({4-[(3-chloro-2-fluorophenyl)amino]-7-methoxyquinazolin-6-yl}oxy)piperidine-1-carboxylate (0.13 g, 0.232 mmol) in DCM (2 ml) at 0° C., was added. The reaction mixture was allowed to warm to room temperature and stirred for 1 hour after which time, the reaction was complete. The reaction mixture was concentrated to dryness, azeotroped twice with toluene and the residue was purified by flash chromatography (silica gel, DCM-NH$_3$/MeOH 5%) to give (2R,4R)-4-({4-[(3-chloro-2-fluorophenyl)amino]-7-methoxyquinazolin-6-yl}oxy)piperidine-2-carboxamide (9) (0.102 g, 100%) as a yellow solid; Mass Spectrum: (M+H)$^+$ 446.1.

Example 5

(2R,4R)-4-({4-[(3-chloro-2-fluorophenyl)amino]-7-methoxyquinazolin-6-yl}oxy)-N-methylpiperidine-2-carboxamide

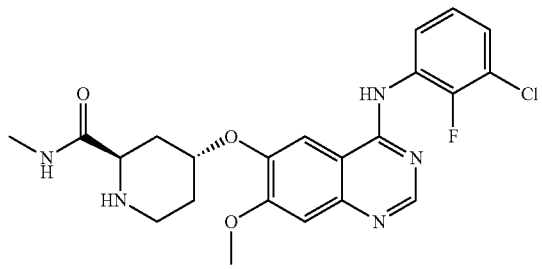 [SMILES: CNC(=O)[C@H]1C[C@H](Oc2cc3c(Nc4cccc(Cl)c4F)ncnc3cc2OC)CCN1]

The title compound was prepared as shown in scheme C:

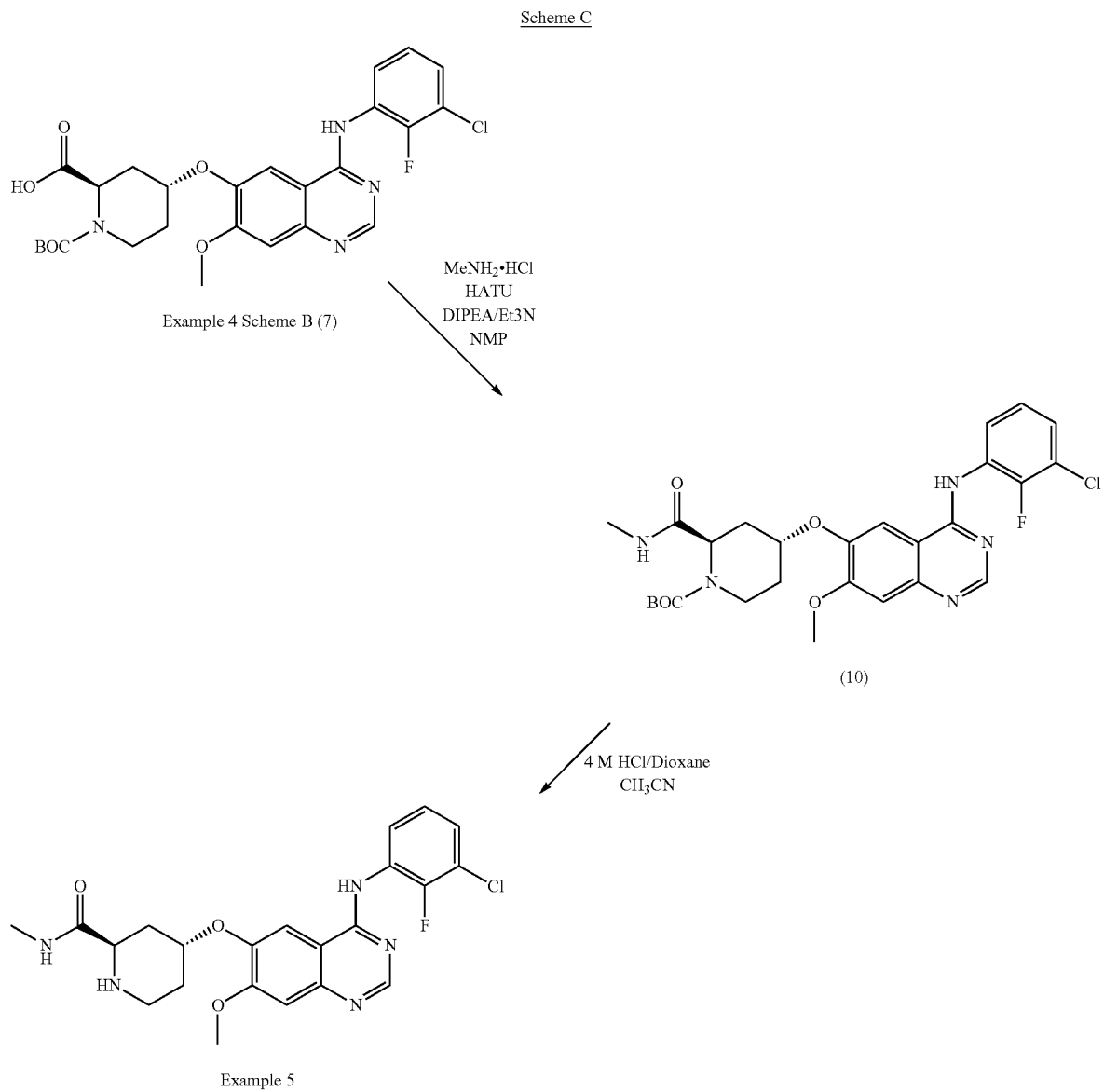

4M Hydrogen chloride (7.5 ml) in dioxane was added to a stirred solution of (1) tert-butyl (2R,4R)-4-({4-[(3-chloro-2-fluorophenyl)amino]-7-methoxyquinazolin-6-yl}oxy)-2-[(methylamino)carbonyl]piperidine-1-carboxylate (4.17 g) in acetonitrile (10 ml) and stirred for 2 hours at room temperature. A second portion of 4M Hydrogen chloride (3.75 ml) in dioxane was added and the mixture stirred a further 1½ hours. The reaction mixture was partitioned between ethyl acetate and saturated sodium bicarbonate solution. The organics were washed with brine, dried ($Na_2SO_4$), filtered and evaporated. The residues were purified by column chromatography eluting with methylene chloride/methanol (saturated with ammonia) (96/4). The fractions containing the desired product were combined and evaporated. The resulting solids were triturated with iso-hexane/methylene chloride filtered and dried under high vacuum at 50° C. to give the title product as a white solid (1.94 g, 57%); $^1$H NMR Spectrum: (DMSO $d_6$) 1.67-1.82 (m, 2H); 1.83-1.94 (m, 1H); 1.98-2.08 (m, 1H); 2.59 (d, 3H); 2.74-2.83 (m, 1H); 2.90-3.01 (m, 1H); 3.48-3.55 (m, 1H); 3.94 (s, 3H); 4.83 (br s, 1H); 7.22 (s, 1H); 7.23-7.30 (m, 1H); 7.43-7.57 (m, 2H); 7.75-7.81 (m, 1H); 7.84 (s, 1H); 8.37 (s, 1H); 9.52 (s, 1H); Mass Spectrum: $(M+H)^+$ 460.

The starting material tert-butyl (2R,4R)-4-({4-[(3-chloro-2-fluorophenyl)amino]-7-methoxyquinazolin-6-yl}oxy)-2-[methylamino)carbonyl]piperidine-1-carboxylate (10) was prepared as follows:

A solution of (2R,4R)-1-(tert-butoxycarbonyl)-4-({4-[(3-chloro-2-fluorophenyl)amino]-7-methoxyquinazolin-6-yl}oxy)piperidine-2-carboxylic acid (4.73 g) (prepared as described in Example 4 Scheme B (7)) in NMP (47 ml) was cooled to 0° C. Methylamine hydrochloride (1.75 g), triethylamine (4.8 ml) and diisopropylethylamine (1.5 ml) were then added. HATU (4.93 g) was added portion-wise such that the internal temperature remained <10° C. and the reaction mixture was left to stand over-night. Further portions of HATU (3.0 g) and diisopropylethylamine (1.5 ml) were then added. After 20 minutes the reaction mixture was quenched with saturated sodium bicarbonate solution and extracted with ethyl acetate (×2).

The combined organics were washed with brine, dried ($Na_2SO_4$), filtered and evaporated. The residues were purified by column chromatography eluting with methylene chloride/methanol (saturated with ammonia) (98.4/1.6). The fractions containing the desired product were combined and evaporated to give tert-butyl (2R,4R)-4-({4-[(3-chloro-2-fluorophenyl)amino]-7-methoxyquinazolin-6-yl}oxy)-2-[(methylamino)carbonyl]piperidine-1-carboxylate (10) as a yellow oil (4.18 g, 86.3%); $^1$H NMR Spectrum: (DMSO $d_6$) 1.52 (s, 10H); 1.91-2.16 (m, 3H); 2.33-2.41 (t, 1H); 2.90 (d, 3H); 2.95-3.16 (m, 1H); 3.33-3.41 (t, 1H); 4.02 (s, 3H); 4.28 (br s, 0.5H) 4.81 (br s, 0.5H); 5.07 (br s, 1H); 7.07-7.18 (m, 2H); 7.27 (s, 1H); 8.13-8.34 (m, 3H); 8.66 (s, 1H); Mass Spectrum: (M–H)$^-$ 558.

Example 6

(2R,4R)-4-({4-[(3-chloro-2-fluorophenyl)amino]-7-methoxyquinazolin-6-yl}oxy)-N,1-dimethylpiperidine-2-carboxamide dimaleate salt (2R,4R)-4-({4-[(3-chloro-2-fluorophenyl)amino]-7-methoxyquinazolin-6-yl}oxy)-N,1-dimethylpiperidine-2-carboxamide (10.0 g: 21.1 mmol, prepared as described in Example 3) was dissolved in acetonitrile (500 ml) at reflux. A 1M solution of maleic acid in acetone (43 ml, 43.0 mmol) was added. The mixture was concentrated to remove acetone, cooled to room temperature and the solids collected by filtration. This amorphous material was slurried in ethyl acetate (400 ml) and heated at 50° C. over the weekend (approximately 65 hours). The mixture was then concentrated to ½ volume and stirred at 50° C. overnight. The resulting suspension was then cooled, filtered, washed with cold ethyl acetate (100 ml) and dried at 50° C. overnight under high vacuum to give the dimaleate salt of (2R,4R)-4-({4-[(3-chloro-2-fluorophenyl)amino]-7-methoxyquinazolin-6-yl}oxy)-N,1-dimethylpiperidine-2-carboxamide as a white crystalline solid (12.7 g, 85.2%); $^1$H NMR Spectrum: (300 MHz DMSO-$D_6$) δ 2.01-2.19 (m, 3H); 2.41-2.46 (m, 1H); 2.66-2.70 (d, 3H); 2.78 (s, 3H); 3.23-3.35 (m, 1H); 3.36-3.45 (m, 1H); 3.91-4.00 (m, 1H); 3.99 (s, 3H); 4.88 (s, 1H); 6.12 (s, 4H); 7.24-7.33 (m, 2H); 7.46-7.55 (m, 2H); 7.90 (s, 1H); 8.43 (s, 1H); 8.67-8.74 (br q, 1H); 9.46-9.92 (br s, 1H).

X-ray powder diffraction patterns of the dimaleate salt were determined by mounting a sample of the crystalline salt on Siemens single silicon crystal (SSC) wafer mounts and spreading out the sample into a thin layer with the aid of a microscope slide. The sample, was spun at 30 revolutions per minute (to improve counting statistics) and irradiated with X-rays generated by a copper long-fine focus tube operated at 40 kV and 40 mA with a wavelength of 1.5406 angstroms on a Bruker D5000 powder X-ray diffractometer. The collimated X-ray source was passed through an automatic variable divergence slit set at V20 and the reflected radiation directed through a 2 mm antiscatter slit and a 0.2 mm detector slit. The sample was exposed for 1 second per 0.02 degree 2-theta increment (continuous scan mode) over the range 2 degrees to 40 degrees 2-theta in theta-theta mode. The running time was 31 minutes and 41 seconds. The instrument was equipped with a scintillation counter as detector. Control and data capture was by means of a Dell Optiplex 686 NT 4.0 Workstation operating with Diffract+ software. Data were collected over the range 2-theta 2-40°, in increments of 2-theta 0.02° with 4 s per increment.

The X-ray powder diffraction pattern for the dimaleate salt is shown in FIG. 1.

Differential Scanning calorimetry (DSC) analysis was conducted on the dimaleate salt using a Mettler DSC820e. Samples of typically less than 5 mg of material contained in a 40 mml aluminium pan fitted with a pierced lid was heated over the temperature range 25° C. to 325° C. at a constant heating rate of 10° C. per minute. A purge gas using nitrogen was used—flow rate 100 ml per minute.

Figure 2:
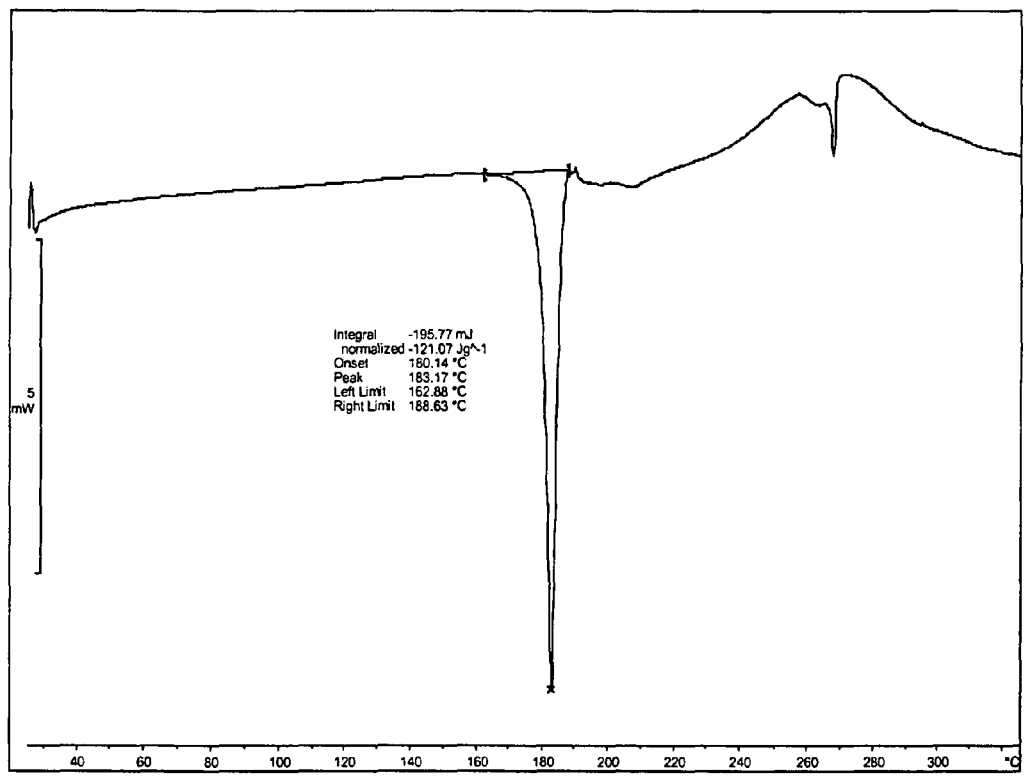
FIG. 2: The differential scanning calorimetry (DSC) trace obtained from the (2R,4R)-4-({4-[(3-chloro-2-fluorophenyl)amino]-7-methoxyquinazolin-6-yl}oxy)-N,1-dimethylpiperidine-2-carboxamide dimaleate salt described in Example 6, with the x-axis showing temperature and the y-axis showing power (mW).
Example 1
(2S,4S)-4-({4-[(3-chloro-2-fluorophenyl)amino]-7-methoxyquinazolin-6-yl}oxy)-1-methylpiperidine-2-carboxamide
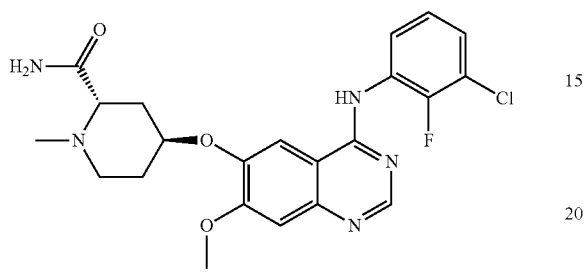
The title compound was prepared as shown in scheme A.

The DSC trace is shown in FIG. 2. The onset temperature of the melting endotherm was in the range of 175-182° C. The peak of the melting endotherm was in the range of 180-187° C.

Example 7

(2S,4R)-4-({4-[(3-chloro-2-fluorophenyl)amino]-7-methoxyquinazolin-6-yl}oxy)-N,1-dimethylpiperidine-2-carboxamide

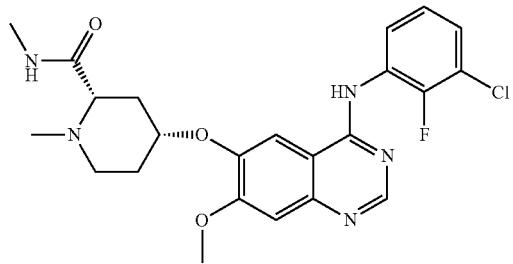 [SMILES: CNC(=O)[C@@H]1C[C@H](Oc2cc3c(Nc4cccc(Cl)c4F)ncnc3cc2OC)CCN1C]

The title compound was prepared as shown in Scheme D

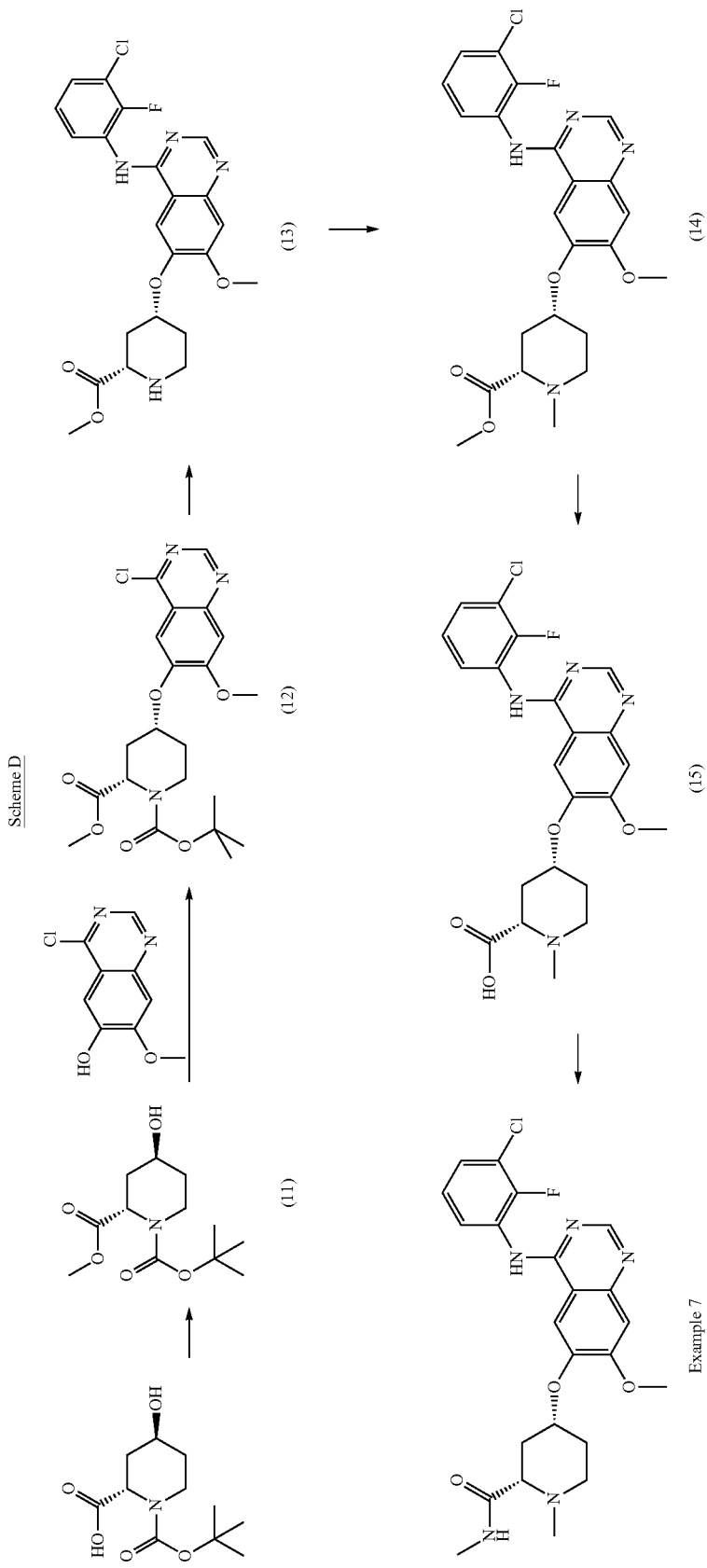

(2S,4R)-4-({4-[(3-chloro-2-fluorophenyl)amino]-7-methoxyquinazolin-6-yl}oxy)-1-methylpiperidine-2-carboxylic acid (15) (145 mg, 0.32 mmol) was dissolved in DMF (10 ml) under nitrogen. Triethylamine (0.13 ml, 0.95 mmol) was added, followed by DIPEA (0.055 ml, 0.32 mmol) and methylamine hydrochloride (0.043 g, 0.63 mmol). The mixture was cooled in an ice/water bath and HATU (180 mg, 0.47 mmol) was then added portionwise such that the temperature remained <10° C. The reaction mixture was stirred at room temperature overnight and evaporated to dryness. The residues were dissolved in EtOAc, washed with water (10 ml), brine (10 ml), dried over $MgSO_4$, filtered and evaporated. The crudes were purified by column chromatography eluting with increasingly polar mixtures of methylene chloride/methanol (100/0-90/10). Fractions containing the desired product were combined and evaporated. The resulting solids were dissolved in methanol, loaded onto an SCX column and eluted with MeOH (20 ml) followed by 7N $NH_3$ in MeOH. Appropriate fractions were combined and evaporated to give the title product as a white solid (69 mg, 40%): $^1$H NMR Spectrum: (DMSO-$d_6$) δ1.63-1.69 (2H, m), 2.15-2.21 (6H, m), 2.55-2.62 (4H, m), 2.93-2.98 (1H, m), 3.94 (3H, s), 4.43-4.51 (1H, m), 7.23 (1H, s), 7.28-7.33 (1H, m), 7.49-7.56 (2H, m), 7.68-7.72 (1H, m), 7.86 (1H, s), 8.39 (1H, s), 9.57 (1H, s); Mass Spectrum: (M+H)$^+$ 474.

The starting material (2S,4R)-4-({4-[(3-chloro-2-fluorophenyl)amino]-7-methoxyquinazolin-6-yl}oxy)-1-methylpiperidine-2-carboxylic acid (15) was prepared as follows:

(2S,4S)—N Boc-4-hydroxy piperidine-2 carboxylic acid benzylamine salt (0.5 g) was dissolved in methanol and loaded onto a SCX column. This was eluted with methanol (20 ml). The combined filtrates were evaporated in vacuo to give a gum (405 mg). This was dissolved in DMF (5 ml). Iodomethane (0.107 ml, 1.7 mmol) was added and the resulting mixture cooled to 0° C. Cesium carbonate (647 mg, 1.98 mmol) was added in one portion and the mixture stirred overnight at room temperature. The reaction mixture was partitioned between water (10 ml) and DCM (3×10 ml). The combined organics were washed with brine (10 ml), dried over $MgSO_4$, filtered and evaporated to give 1-tert-butyl 2-methyl (2S,4S)-4-hydroxypiperidine-1,2-dicarboxylate (11) as a clear gum (347 mg, 81%): $^1$H NMR Spectrum: (CDCl$_3$) δ1.39-1.50 (10H, m), 1.60-1.66 (1H, m), 1.86-1.96 (2H, m), 2.40-2.49 (1H, m), 2.96-3.10 (1H, m), 3.65 (1H, t), 3.73 (3H, s), 3.95-4.18 (1H, m), 4.82-5.06 (1H, m).

A solution of DEAD (0.329 ml, 2.08 mmol) in DCM (2 ml) was added to as stirred suspension of 4-chloro-7-methoxyquinazolin-6-ol (283 mg, 1.74 mmol prepared as described in Example 16 of WO03/082831), 1-tert-butyl 2-methyl (2S,4S)-4-hydroxypiperidine-1,2-dicarboxylate (11) (450 mg, 2.08 mmol) and triphenylphosphine (547 mg, 2.098 mmol) in DCM (10 ml), such that the internal temperature remained <30° C. The reaction mixture was stirred overnight and evaporated to dryness. The residues were purified by column chromatography on $SiO_2$ eluting with increasingly polar mixtures of DCM/methanol (100/0-95/5). The fractions containing the desired product were combined and evaporated to give 1-tert-butyl 2-methyl (2S,4R)-4-[(4-chloro-7-methoxyquinazolin-6-yl)oxy]piperidine-1,2-dicarboxylate (12) as a gum (478 mg, 79%): $^1$H NMR Spectrum: (DMSO-$d_6$) δ1.39-1.46 (10H, m), 1.73-1.84 (1H, m), 1.92-2.03 (1H, m), 2.10-2.18 (1H, m), 2.60-2.69 (1H, m), 3.15-3.40 (3H, m), 3.74-3.85 (1H, m), 4.01 (3H, s), 4.61-4.73 (1H, m), 5.06 (1H, s), 7.43 (1H, s), 7.47 (1H, s), 8.89 (1H, s), 8.97 (1H, s); Mass Spectrum: (M+H)$^+$ 452.

1-tert-butyl 2-methyl (2S,4R)-4-[(4-chloro-7-methoxyquinazolin-6-yl)oxy]piperidine-1,2-dicarboxylate (12) (0.45 g, 1.0 mmol) was dissolved in MeCN (11 ml) under nitrogen. 3-Chloro-2-fluoroaniline (153 mg, 1.05 mmol) was then added followed by 4M HCl in dioxane (1.2 ml). The resulting mixture was heated overnight at 60° C. The reaction mixture was cooled to −8° C. and the resulting solids collected by filtration and washed with diethylether. The solids were dissolved in methanol, loaded onto an SCX column and eluted with methanol followed by 7N $NH_3$ in MeOH. Appropriate fractions were combined and evaporated. The residues were purified by column chromatography on $SiO_2$ eluting with increasingly polar mixtures of DCM/methanol (100/0-95/5). The fractions containing the desired product were combined and evaporated to give methyl (2S,4R)-4-({4-[(3-chloro-2-fluorophenyl)amino]-7-methoxyquinazolin-6-yl}oxy)piperidine-2-carboxylate (13) as a clear gum (316 mg, 69%): $^1$H NMR Spectrum: (DMSO-$d_6$) δ1.45-1.58 (2H, m), 2.02-2.11 (1H, m), 2.32-2.40 (1H, m), 2.57-2.67 (1H, m), 3.08-3.13 (1H, m), 3.42-3.48 (1H, m), 3.64 (3H, s), 3.95 (3H, s), 4.54-4.64 (1H, m), 7.05-7.10 (1H, m), 7.23 (1H, s), 7.28-7.33 (1H, m), 7.48-7.57 (2H, m), 7.85 (1H, s), 8.38 (1H, s), 9.56 (1H, s); Mass Spectrum: (M+H)$^+$ 461.

Methyl (2S,4R)-4-({4-[(3-chloro-2-fluorophenyl)amino]-7-methoxyquinazolin-6-yl}oxy)piperidine-2-carboxylate (13) (0.35 g, 0.76 mmol) was dissolved in a solution of 15% Acetic acid/methylene chloride (6.1 ml). To this was then added powdered 4A° molecular sieves (0.63 g) and the resulting suspension stirred for 5 minutes. 37% formaldehyde in water (0.56 ml) was added drop-wise and the mixture stirred a further 2 minutes. Sodium triacetoxyborohydride (0.29 g) was added in one portion. The reaction mixture was stirred a further 2 hours at room temperature, filtered and evaporated. The residues were partitioned between ethyl acetate and saturated aqueous sodium hydrogen carbonate solution. The combined organics were washed with brine, dried over $MgSO_4$, filtered and evaporated. The crudes were purified by column chromatography on $SiO_2$ eluting with increasingly polar mixtures of DCM/methanol (100/0-95/5). The fractions containing the desired product were combined and evaporated to give methyl (2S,4R)-4-({4-[(3-chloro-2-fluorophenyl)amino]-7-methoxyquinazolin-6-yl}oxy)-1-methylpiperidine-2-carboxylate (14) as a foam (252 mg, 70%): $^1$H NMR Spectrum: (DMSO-$d_6$) δ1.72-1.78 (2H, m), 2.05-2.35 (6H, m), 2.95-3.04 (2H, m), 3.63 (3H, s), 3.94 (3H, s), 4.51-4.59 (1H, m), 7.23 (1H, s), 7.29-7.31 (1H, m), 7.49-7.56 (2H, m), 7.84 (1H, s), 8.39 (1H, s), 9.55 (1H, s); Mass Spectrum: (M+H)$^+$ 475.

2N NaOH (1.3 ml, 2.66 mmol) was added to a solution of methyl (2S,4R)-4-({4-[(3-chloro-2-fluorophenyl)amino]-7-methoxyquinazolin-6-yl}oxy)-1-methylpiperidine-2-carboxylate (14) (0.252 g, 0.53 mmol) in THF (5 ml) and methanol (1 ml). The reaction mixture was stirred overnight at room temperature and evaporated to dryness. The residues were dissolved in water (10 ml) and the solution acidified to pH6 with 2N HCl. The resulting solids were collected by filtration, washed with water (5 ml) followed by diethylether (5 ml) and dried under vacuum to give (2S,4R)-4-({4-[(3-chloro-2-fluorophenyl)amino]-7-methoxyquinazolin-6-yl}oxy)-1-methylpiperidine-2-carboxylic acid (15) as a cream solid (145 mg, 59%): $^1$H NMR Spectrum: (DMSO-$d_6$) δ1.72-1.90 (2H, m), 2.20-2.31 (1H, m), 2.40-2.55 (1H+DMSO, m), 2.66 (3H, s), 2.84-2.94 (1H, m), 3.10-4.10 (2H, m), 3.95 (3H, s), 4.56-4.60

(1H, m), 7.18-7.25 (2H, m), 7.48-7.55 (2H, m), 8.05 (1H, s), 8.40 (1H, s); Mass Spectrum: (M+H)+ 461.
Example 8
(2R,4S)-4-({4-[(3-chloro-2-fluorophenyl)amino]-7-methoxyquinazolin-6-yl}oxy)-N,1-dimethylpiperidine-2-carboxamide
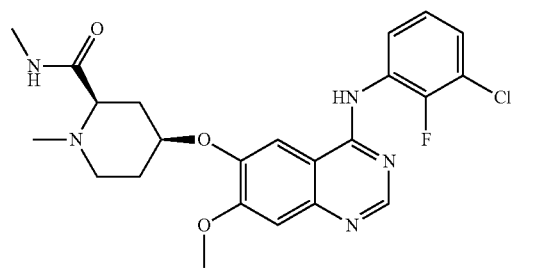 [SMILES: CNC(=O)[C@H]1C[C@@H](Oc2cc3c(Nc4cccc(Cl)c4F)ncnc3cc2OC)CCN1C]
The title compound was prepared as shown in Scheme E Scheme E
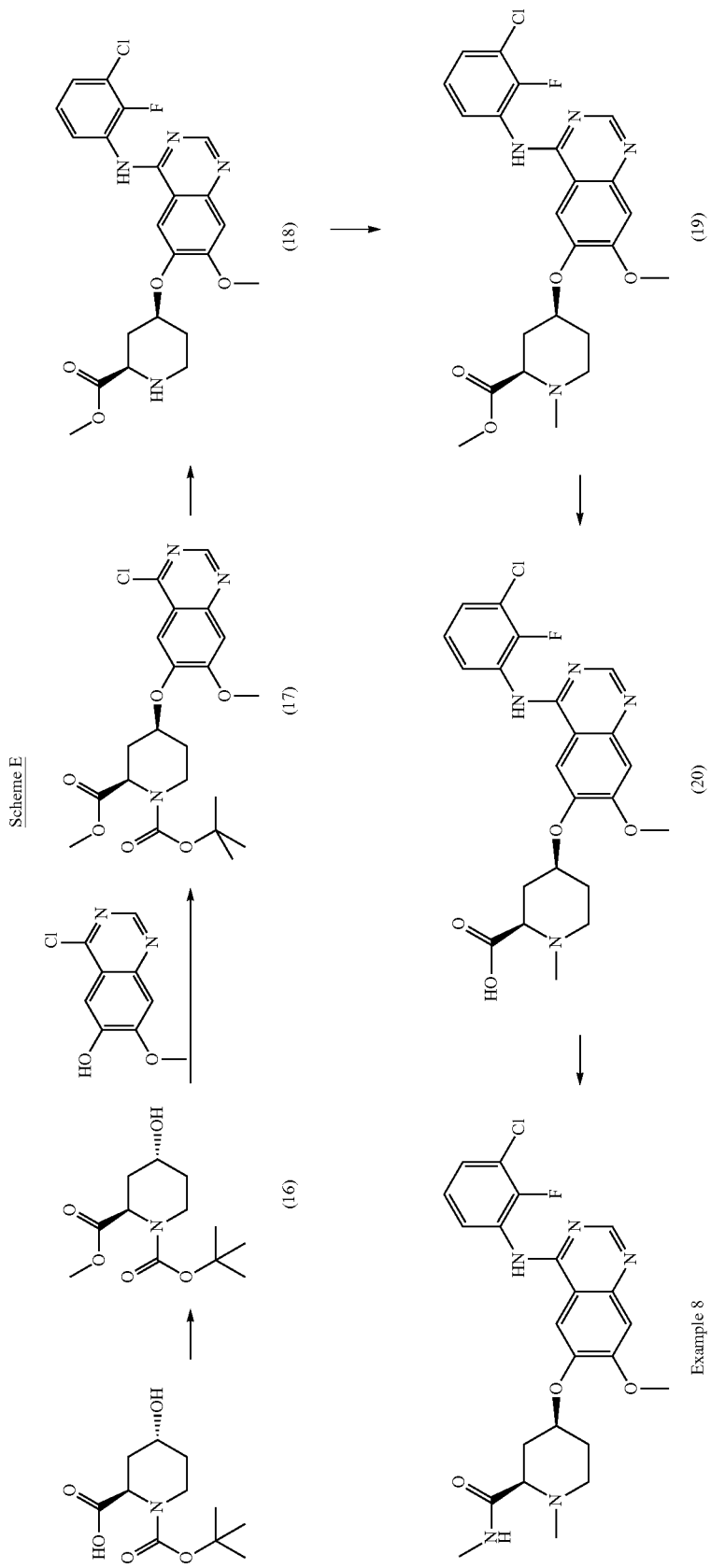

(2R,4S)-4-({4-[(3-chloro-2-fluorophenyl)amino]-7-methoxyquinazolin-6-yl}oxy)-1-methylpiperidine-2-carboxylic acid (20) was coupled with methylamine hydrochloride analogously as for the equivalent step in Example 7 to give the title compound (2R,4S)-4-({4-[(3-chloro-2-fluorophenyl)amino]-7-methoxyquinazolin-6-yl}oxy)-N,1-dimethylpiperidine-2-carboxamide: $^1$H NMR Spectrum: (DMSO-$d_6$) δ1.63-1.72 (2H, m), 2.15-2.21 (6H, m), 2.55-2.62 (4H, m), 2.93-2.98 (1H, m), 3.94 (3H, s), 4.43-4.51 (1H, m), 7.23 (1H, s), 7.28-7.33 (1H, m), 7.49-7.56 (2H, m), 7.68-7.72 (1H, m), 7.86 (1H, s), 8.39 (1H, s), 9.57 (1H, s); Mass Spectrum: (M+H)$^+$ 474.

The starting material (2R,4S)-4-({4-[(3-chloro-2-fluorophenyl)amino]-7-methoxyquinazolin-6-yl}oxy)-1-methylpiperidine-2-carboxylic acid (20) was prepared as follows:

(2R,4R)—N Boc-4-hydroxy piperidine-2 carboxylic acid benzylamine salt was reacted analogously as for the equivalent step in Example 7 to give 1-tert-butyl 2-methyl (2R,4R)-4-hydroxypiperidine-1,2-dicarboxylate (16): $^1$H NMR Spectrum: (CDCl$_3$) δ1.30-1.50 (10H, m), 1.60-1.65 (2H, m), 1.89-1.94 (1H, m), 2.40-2.49 (1H, m), 2.95-3.05 (1H, m), 3.63-3.70 (1H, m), 3.73 (3H, s), 3.96-4.18 (1H, m), 4.84-5.02 (1H, m).

1-tert-butyl 2-methyl (2R,4R)-4-hydroxypiperidine-1,2-dicarboxylate (16) was coupled to 4-chloro-7-methoxyquinazolin-6-ol analogously as for the equivalent step in Example 7 to give 1-tert-butyl 2-methyl (2R,4S)-4-[(4-chloro-7-methoxyquinazolin-6-yl)oxy]piperidine-1,2-dicarboxylate (17): $^1$H NMR Spectrum: (DMSO-$d_6$) δ1.39-1.46 (10H, m), 1.73-1.84 (1H, m), 1.92-2.03 (1H, m), 2.10-2.18 (1H, m), 2.60-2.69 (1H, m), 3.15-3.40 (3H, m), 3.74-3.85 (1H, m), 4.01 (3H, s), 4.61-4.73 (1H, m), 5.06 (1H, s), 7.43 (1H, s), 7.47 (1H, s), 8.89 (1H, s), 8.97 (1H, s); Mass Spectrum: (M+H)$^+$ 452.

1-tert-butyl 2-methyl (2R,4S)-4-[(4-chloro-7-methoxyquinazolin-6-yl)oxy]piperidine-1,2-dicarboxylate (17) was reacted with 3-Chloro-2-fluoroaniline analogously as for the equivalent step in Example 7 to give methyl (2R,4S)-4-({4-[(3-chloro-2-fluorophenyl)amino]-7-methoxyquinazolin-6-yl}oxy)piperidine-2-carboxylate (18): $^1$H NMR Spectrum: (DMSO-$d_6$) δ1.45-1.56 (2H, m), 2.03-2.12 (1H, m), 2.31-2.38 (1H, m), 2.60-2.67 (1H, m), 3.08-3.15 (1H, m), 3.44-3.48 (1H, m), 3.64 (3H, s), 3.95 (3H, s), 4.55-4.63 (1H, m), 7.23 (1H, s), 7.26-7.32 (1H, m), 7.48-7.58 (2H, m), 7.85 (1H, s), 8.38 (1H, s), 9.56 (1H, s); Mass Spectrum: (M+H)$^+$ 461.

Methyl (2R,4S)-4-({4-[(3-chloro-2-fluorophenyl)amino]-7-methoxyquinazolin-6-yl}oxy)piperidine-2-carboxylate (18) was reacted analogously as for the equivalent step in Example 7 to give methyl (2R,4S)-4-({4-[(3-chloro-2-fluorophenyl)amino]-7-methoxyquinazolin-6-yl}oxy)-1-methylpiperidine-2-carboxylate (19): $^1$H NMR Spectrum: (DMSO-$d_6$) δ1.68-1.77 (2H, m), 2.07-2.14 (1H, m), 2.17-2.21 (5H, m), 2.91-3.03 (2H, m), 3.63 (3H, s), 3.94 (3H, s), 4.50-4.59 (1H, m), 7.22 (1H, s), 7.28-7.32 (1H, m), 7.48-7.57 (2H, m), 7.83 (1H, s), 8.38 (1H, s), 9.54 (1H, s); Mass Spectrum: (M+H)$^+$ 475.

Methyl (2R,4S)-4-({4-[(3-chloro-2-fluorophenyl)amino]-7-methoxyquinazolin-6-yl}oxy)-1-methylpiperidine-2-carboxylate (19) was hydrolysed analogously as for the equivalent step in Example 6 to give (2R,4S)-4-({4-[(3-chloro-2-fluorophenyl)amino]-7-methoxyquinazolin-6-yl}oxy)-1-methylpiperidine-2-carboxylic acid (20): $^1$H NMR Spectrum: (DMSO-$d_6$) δ1.72-1.90 (2H, m), 2.20-2.31 (1H, m), 2.45-2.55 (1H+DMSO, m), 2.66 (3H, s), 2.84-2.94 (1H, m), 3.27-3.34 (1H, m), 3.48-3.49 (1H, m), 3.95 (3H, s), 4.56-4.60 (1H, m), 7.18-7.25 (2H, m), 7.48-7.55 (2H, m), 8.05 (1H, s), 8.40 (1H, s); Mass Spectrum: (M+H)$^+$ 461.

Prophetic Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100%. | |

The above formulations may be prepared by conventional procedures well known in the pharmaceutical art. For example the tablet may be prepared by blending the components together and compressing the mixture into a tablet.

The invention claimed is:
1. (2R,4R)-4-({4-[(3-chloro-2-fluorophenyl)amino]-7-methoxyquinazolin-6-yl}loxy)-N,1-dimethylpiperidine-2-carboxamide dimaleate salt.
2. (2R,4R)-4-({4-[(3-chloro-2-fluorophenyl)amino]-7-methoxyquinazolin-6-yl}loxy)-N,1-dimethylpiperidine-2-carboxamide, or a pharmaceutically acceptable salt thereof.
3. (2R,4R)-4-({4-[(3-chloro-2-fluorophenyl)amino]-7-methoxyquinazolin-6-yl}oxy)-N,1-dimethylpiperidine-2-carboxamide.

* * * * *